United States Patent
Cheng et al.

(10) Patent No.: US 7,507,757 B2
(45) Date of Patent: Mar. 24, 2009

(54) SUBSTITUTED HETEROCYCLIC DERIVATIVES USEFUL AS ANTIDIABETIC AND ANTIOBESITY AGENTS AND METHOD

(75) Inventors: Peter T. W. Cheng, Princeton, NJ (US); Sean Chen, Princeton, NJ (US); Charles Z. Ding, Plano, TX (US); Timothy F. Herpin, Princeton, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 608 days.

(21) Appl. No.: 11/016,183

(22) Filed: Dec. 17, 2004

(65) Prior Publication Data
US 2005/0119312 A1 Jun. 2, 2005

Related U.S. Application Data

(62) Division of application No. 10/616,283, filed on Jul. 8, 2003, now Pat. No. 6,875,782.

(60) Provisional application No. 60/394,553, filed on Jul. 9, 2002.

(51) Int. Cl.
*A61K 31/4164* (2006.01)
*C07D 233/56* (2006.01)
(52) U.S. Cl. .................. 514/399; 548/336.1; 548/338.1
(58) Field of Classification Search .................. 514/399; 548/336.1, 338.1
See application file for complete search history.

(56) References Cited

U.S. PATENT DOCUMENTS

| 6,506,781 B1 | 1/2003 | Cobb et al. |
| 6,653,314 B2 | 11/2003 | Cheng et al. |

FOREIGN PATENT DOCUMENTS

| FR | 2778314 | 7/1998 |
| JP | 10-67759 | 3/1998 |
| JP | 11-263775 | 9/1999 |
| WO | WO 95/18130 | 12/1994 |
| WO | WO 97/00258 | 6/1996 |
| WO | WO 99/16770 | 9/1998 |
| WO | WO 01/38325 A1 | 9/2000 |
| WO | WO01/00603 | 1/2001 |
| WO | 01/21602 | 3/2001 |

*Primary Examiner*—Charanjit S Aulakh
(74) *Attorney, Agent, or Firm*—Burton Rodney

(57) ABSTRACT

Compounds are provided which are useful as antidiabetic agents and antiobesity agents and have the structure

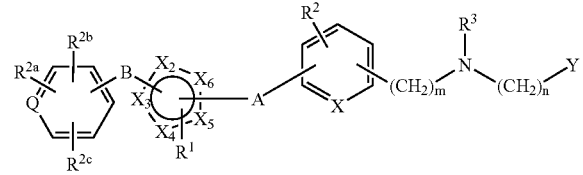

wherein m is 0, 1 or 2; n is 0, 1 or 2;
Q is C or N;
A is $(CH_2)_x$ where x is 1 to 5, or A is $(CH_2)_{x^1}$ where $x^1$ is 1 to 5 with an alkenyl bond or an alkynyl bond embedded anywhere in the chain, or A is $-(CH_2)_{x^2}-O-(CH_2)_{x^3}-$ where $x^2$ is 0 to 5 and $x^3$ is 0 to 5, provided that at least one of $x^2$ and $x^3$ is other than 0;
B is a bond or is $(CH_2)_{x^4}$ where $x^4$ is 1 to 5;
X is CH;
$X_2$ is N;
$X_3$ is C;
$X_4$ is N;
$X_5$ is C;
$X_6$ is C.

13 Claims, No Drawings

SUBSTITUTED HETEROCYCLIC DERIVATIVES USEFUL AS ANTIDIABETIC AND ANTIOBESITY AGENTS AND METHOD

This application is a Divisional of U.S. patent application Ser. No. 10/616,283, filed Jul. 8, 2003, now U.S. Pat. No. 6,875,782, that claims the benefit of U.S. Provisional Application 60/394,553, filed Jul. 9, 2002 which are incorporated herein by reference.

FIELD OF THE INVENTION

The present invention relates to novel substituted heterocyclic derivatives which modulate blood glucose levels, triglyceride levels, insulin levels and non-esterified fatty acid (NEFA) levels, and thus are particularly useful in the treatment of diabetes and obesity, and to a method for treating diabetes, especially Type 2 diabetes, as well as hyperglycemia, hyperinsulinemia, hyperlipidemia, obesity, atherosclerosis and related diseases employing such substituted heterocyclic derivatives alone or in combination with another antidiabetic agent and/or a hypolipidemic agent and/or other therapeutic agents.

DESCRIPTION OF THE INVENTION

In accordance with the present invention, substituted heterocyclic derivatives are provided which have the structure I

I

[structure]

wherein m is 0, 1 or 2; n is 0, 1 or 2;

Q is C or N;

A is $(CH_2)_x$ where x is 1 to 5, or A is $(CH_2)_x^1$ where $x^1$ is 1 to 5 with an alkenyl bond or an alkynyl bond embedded anywhere in the chain, or A is $—(CH_2)_x^2—O—(CH_2)_x^3—$ where $x^2$ is 0 to 5 and $x^3$ is 0 to 5, provided that at least one of $x^2$ and $x^3$ is other than 0;

B is a bond or is $(CH_2)_x^4$ where $x^4$ is 1 to 5;

X is CH or N;

$X_2$ is C, N, O or S;

$X_3$ is C, N, O or S;

$X_4$ is C, N, O or S;

$X_5$ is C, N, O or S;

$X_6$ is C, N, O or S;

provided that at least one of $X_2, X_3, X_4, X_5$ and $X_6$ is N; and at least one of $X_2, X_3, X_4, X_5$ and $X_6$ is C, and specifically excluding the structure(s) as shown below:

[structure]

where $X_2=N$, $X_3=C$, $X_4=O$ or S, Z=O or a bond

In each of X through $X_6$, as defined above, C may include CH.

$R^1$ is H or alkyl;

$R^2$ is H, alkyl, alkoxy, halogen, amino, substituted amino or cyano;

$R^{2a}$, $R^{2b}$ and $R^{2c}$ may be the same or different and are selected from H, alkyl, alkoxy, halogen, amino, substituted amino or cyano;

$R^3$ is selected from H, alkyl, arylalkyl, aryloxycarbonyl, alkyloxycarbonyl, alkynyloxycarbonyl, alkenyloxycarbonyl, arylcarbonyl, alkylcarbonyl, aryl, heteroaryl, cycloheteroalkyl, heteroarylcarbonyl, heteroaryl-heteroarylalkyl, alkylcarbonylamino, arylcarbonylamino, heteroarylcarbonylamino, alkoxycarbonylamino, aryloxycarbonylamino, heteroaryloxycarbonylamino, heteroaryl-heteroarylcarbonyl, alkylsulfonyl, alkenylsulfonyl, heteroaryloxycarbonyl, cycloheteroalkyloxycarbonyl, heteroarylalkyl, aminocarbonyl, substituted aminocarbonyl, alkylaminocarbonyl, arylaminocarbonyl, heteroarylalkenyl, cycloheteroalkyl-heteroarylalkyl; hydroxyalkyl, alkoxy, alkoxyaryloxycarbonyl, arylalkyloxycarbonyl, alkylaryloxycarbonyl, arylheteroarylalkyl, arylalkylarylalkyl, aryloxyarylalkyl, haloalkoxyaryloxycarbonyl, alkoxycarbonylaryloxycarbonyl, aryloxyaryloxycarbonyl, arylsulfinylarylcarbonyl, arylthioarylcarbonyl, alkoxycarbonylaryloxycarbonyl, arylalkenyloxycarbonyl, heteroaryloxyarylalkyl, aryloxyarylcarbonyl, aryloxyarylalkyloxycarbonyl, arylalkenyloxycarbonyl, arylalkylcarbonyl, aryloxyalkyloxycarbonyl, arylalkylsulfonyl, arylthiocarbonyl, arylalkenylsulfonyl, heteroarylsulfonyl, arylsulfonyl, alkoxyarylalkyl, heteroarylalkoxycarbonyl, arylheteroarylalkyl, alkoxyarylcarbonyl, aryloxyheteroarylalkyl, heteroarylalkyloxyarylalkyl, arylarylalkyl, arylalkenylarylalkyl, arylalkoxyarylalkyl, arylcarbonylarylalkyl, alkylaryloxyarylalkyl, arylalkoxycarbonylheteroarylalkyl, heteroarylarylalkyl, arylcarbonylheteroarylalkyl, heteroaryloxyarylalkyl, arylalkenylheteroarylalkyl, arylaminoarylalkyl, aminocarbonylarylarylalkyl;

Y is $CO_2R^4$ (where $R^4$ is H or alkyl, or a prodrug ester) or Y is a C-linked 1-tetrazole, a phosphonic acid of the structure $P(O)(OR^{4a})R^5$, (where $R^{4a}$ is H or a prodrug ester, $R^5$ is alkyl or aryl) or a phosphonic acid of the structure $P(O)(OR^{4a})_2$;

$(CH_2)_x$, $(CH_2)_x^1$, $(CH_2)_x^2$, $(CH_2)_x^3$, $(CH_2)_x^4$, $(CH_2)_m$, and $(CH_2)_n$ may be optionally substituted with 1, 2 or 3 substituents;

including all stereoisomers thereof, prodrug esters thereof, and pharmaceutically acceptable salts thereof.

Examples of

[structure]

which are present in the compounds of the invention include, but are not limited to,

[structures]

-continued

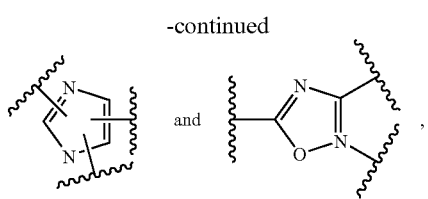

as well as the five-membered rings covered under the definition of heteroaryl set out hereinafter, preferably

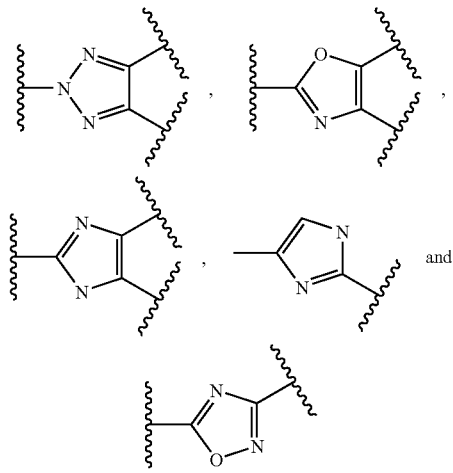

Preferred are compounds of formula I of the invention having the structure IA

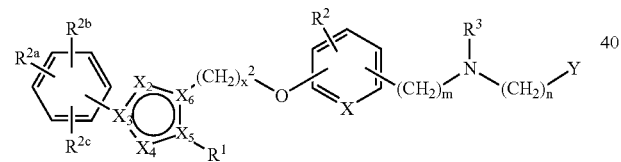

where X is CH

More preferred are compounds of formula I of the invention having the structure IB

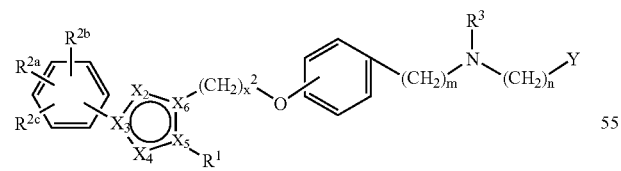

In the above compounds, it is most preferred that $R^{2a}$, $R^{2b}$ and $R^{2c}$ are each H; $R^1$ is alkyl, preferably $CH_3$; $x^2$ is 1 to 3; $R^2$ is H; m is 0 or $(CH_2)_m$ is $CH_2$ or CHOH or CH-alkyl, $X_2$, $X_3$, $X_4$, $X_5$ and $X_6$ represent a total of 1, 2 or 3 nitrogens; $(CH_2)_n$ is a bond or $CH_2$, $R^3$ is arylalkyloxycarbonyl, arylheteroarylalkyl, aryloxyarylalkyl, arylalkyl, aryloxycarbonyl, haloaryloxycarbonyl, alkoxyaryloxycarbonyl, alkylaryloxycarbonyl, aryloxyaryloxycarbonyl, heteroaryloxyarylalkyl, heteroaryloxycarbonyl, aryloxyarylcarbonyl, arylalkenyloxycarbonyl, cycloalkylaryloxycarbonyl, arylalkylarylcarbonyl, heteroaryl-heteroarylalkyl, cycloalkyloxyaryloxycarbonyl, heteroaryl-heteroarylcarbonyl, arylalkylsulfonyl, arylalkenylsulfonyl, alkoxyarylalkyl, arylthiocarbonyl, cycloheteroalkylalkyloxycarbonyl, cycloheteroalkyloxycarbonyl, or polyhaloalkylaryloxycarbonyl, which may be optionally substituted, more preferably alkoxyaryloxycarbonyl.

Preferred compounds of the invention include the following:

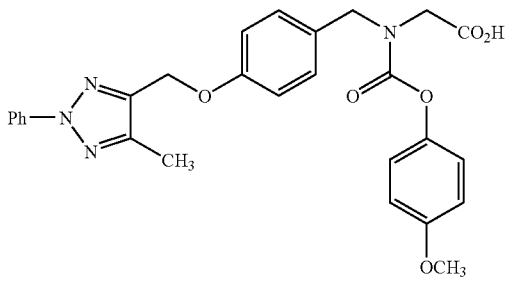

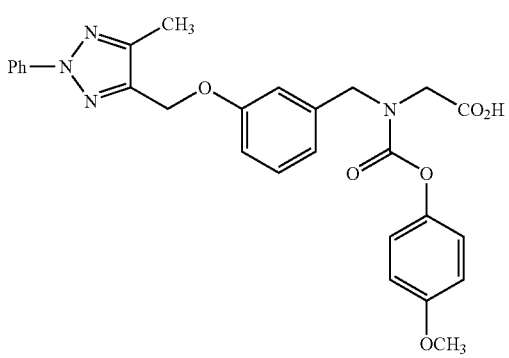

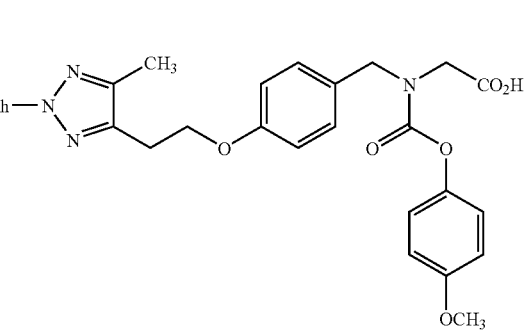

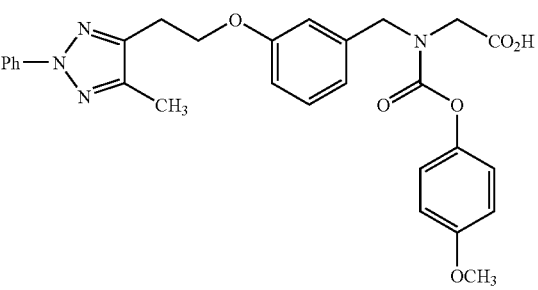

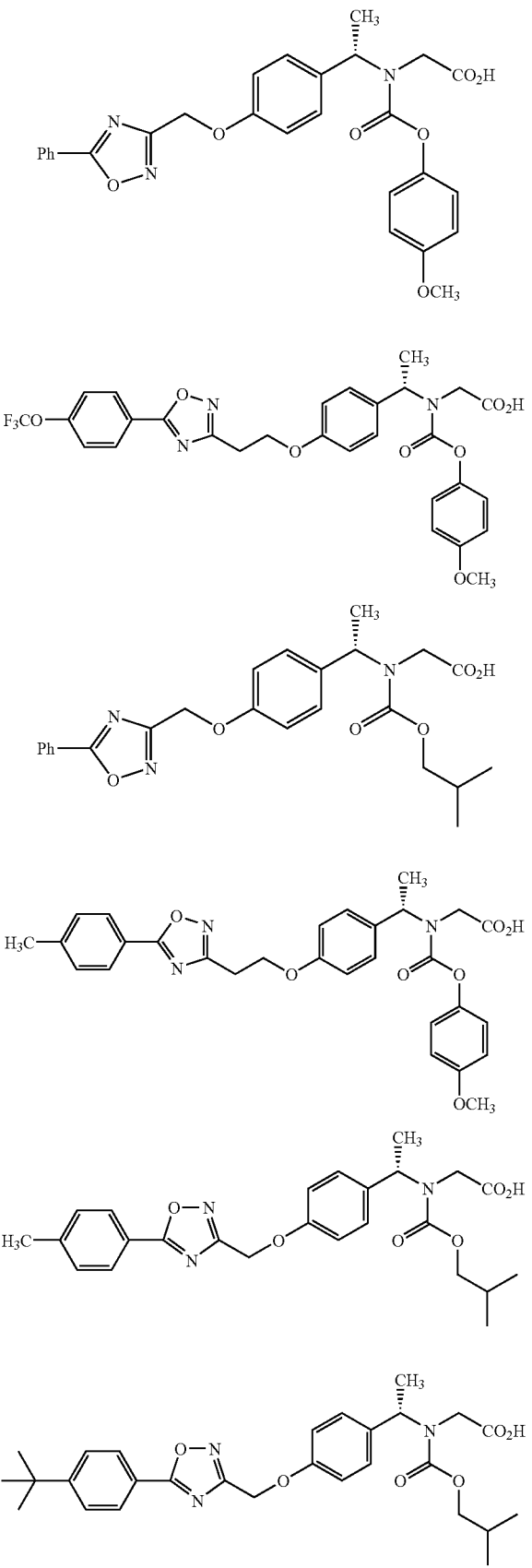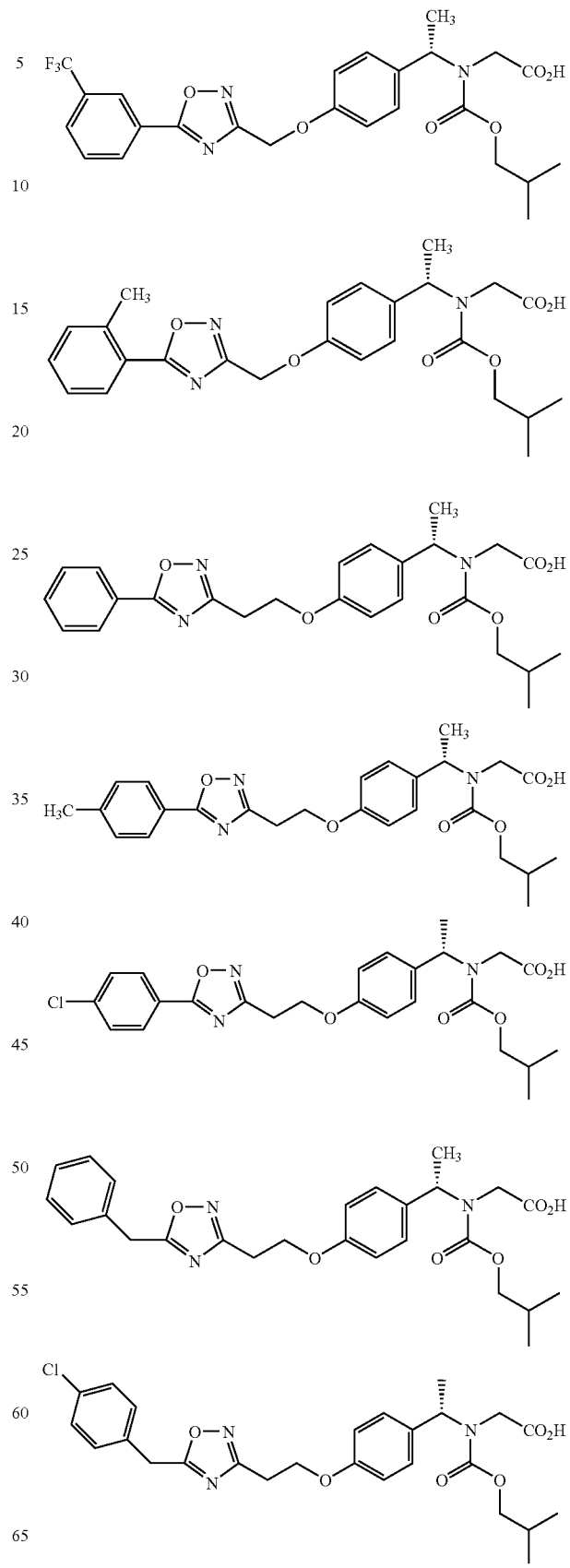

-continued

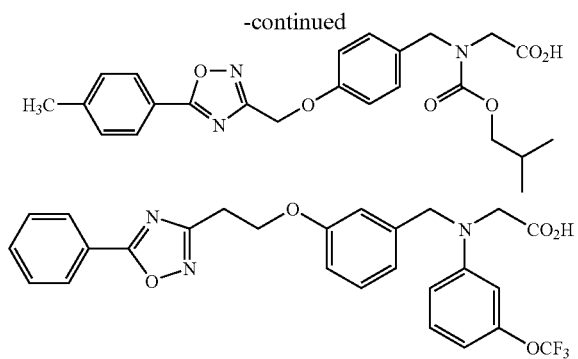

In addition, in accordance with the present invention, a method is provided for treating diabetes, especially Type 2 diabetes, and related diseases such as Type I diabetes, insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, atherosclerosis, and related diseases wherein a therapeutically effective amount of a compound of structure I is administered to a patient in need of treatment.

In addition, in accordance with the present invention, a method is provided for treating early malignant lesions (such as ductal carcinoma in situ of the breast and lobular carcinoma in situ of the breast), premalignant lesions (such as fibroadenoma of the breast and prostatic intraepithelial neoplasia (PIN), liposarcomas and various other epithelial tumors (including breast, prostate, colon, ovarian, gastric and lung), irritable bowel syndrome, Crohn's disease, gastric ulceritis, and osteoporosis and proliferative diseases such as psoriasis, wherein a therapeutically effective amount of a compound of structure I is administered to a patient in need of treatment.

In addition, in accordance with the present invention, a method is provided for treating diabetes and related diseases as defined above and hereinafter, wherein a therapeutically effective amount of a combination of a compound of structure I and another type antidiabetic agent and/or a hypolipidemic agent, and/or lipid modulating agent and/or other type of therapeutic agent, is administered to a human patient in need of treatment.

In the above method of the invention, the compound of structure I will be employed in a weight ratio to the antidiabetic agent (depending upon its mode of operation) within the range from about 0.01:1 to about 100:1, preferably from about 0.5:1 to about 10:1.

The conditions, diseases, and maladies collectively referenced to as "Syndrome X" or Dysmetabolic Syndrome (as detailed in Johanson, *J. Clin. Endocrinol. Metab.*, 1997, 82, 727-734, and other publications) include hyperglycemia and/or prediabetic insulin resistance syndrome, and is characterized by an initial insulin resistant state generating hyperinsulinemia, dyslipidemia, and impaired glucose tolerance, which can progress to Type II diabetes, characterized by hyperglycemia, which can progress to diabetic complications.

The term "diabetes and related diseases" refers to Type II diabetes, Type I diabetes, impaired glucose tolerance, obesity, hyperglycemia, Syndrome X, dysmetabolic syndrome, diabetic complications and hyperinsulinemia.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than compounds of formula I), one or more anti-obesity agents, and/or one or more lipid-lowering agents, one or more lipid modulating agents (including anti-atherosclerosis agents), and/or one or more antiplatelet agents, one or more agents for treating hypertension, one or more anti-cancer drugs, one or more agents for treating arthritis, one or more anti-osteoporosis agents, one or more anti-obesity agents, one or more agents for treating immunomodulatory diseases, and/or one or more agents for treating anorexia nervosa.

The term "lipid-modulating" agent as employed herein refers to agents which lower LDL and/or raise HDL and/or lower triglycerides and/or lower total cholesterol and/or other known mechanisms for therapeutically treating lipid disorders.

DETAILED DESCRIPTION OF THE INVENTION

The compounds of the formula I of the present invention may be prepared according to the following general synthetic schemes, as well as relevant published literature procedures that are used by one skilled in the art. Exemplary reagents and procedures for these reactions appear hereinafter and in the working Examples. Protection and deprotection in the Schemes below may be carried out by procedures generally known in the art (see, for example, T. W. Greene & P. G. M. Wuts, Protecting Groups in Organic Synthesis, $3^{rd}$ Edition, 1999 [Wiley]).

Scheme 1 describes a general synthesis of the amino acids described in this invention. An alcohol 1 ($R^5(CH_2)_x{}^2OH$) is coupled with a hydroxy aryl- or heteroaryl-aldehyde 2 (preferably 3- or 4-hydroxybenzaldehyde) under standard Mitsunobu reaction conditions (e.g. Mitsunobu, O., *Synthesis*, 1981, 1). The resulting aldehyde 3 is then subjected to reductive amination using procedures known in the literature (e.g. Abdel-Magid et al, *J. Org. Chem.* 1996, 61, 3849) with an α-amino ester hydrochloride 4. PG in Scheme 1 denotes a preferred carboxylic acid-protecting group, such as a methyl or tert-butyl ester. The resulting secondary amino-ester 5 is then subjected to a second reductive amination using methods known in the literature (e.g. Abdel-Magid et al, *J. Org. Chem.* 1996, 61, 3849) with an $R^{3a}$ aldehyde 6. Final deprotection of the carboxylic acid ester under standard conditions known in the literature (reference: Greene et al supra) utilizing basic conditions (for methyl esters) or acidic conditions (for tert-butyl esters) then furnishes the desired amino acid products II.

An alternative route to the aldehyde 3 is shown in Scheme 1A. Alcohol 1 ($R^5(CH_2)_xOH$) is treated with methanesulfonyl chloride to give the corresponding mesylate 7. The mesylate 7 is then alkylated under standard basic conditions with a hydroxyaryl or hydroxyheteroaryl aldehyde 2 to furnish the aldehyde 3.

A route to the amino acids III is shown in Scheme 2. The secondary amine-ester 5 is deprotected under standard conditions (basic conditions if the protecting group (PG) is methyl; acidic conditions if PG is tert-butyl; ref. Greene et al supra) to furnish the corresponding amino acid 8. Reductive amination with aldehyde 9 under analogous conditions as described in Scheme 1 provides the desired tertiary amino acid products III.

Alternatively, as shown in Scheme 3, reaction of the secondary amine-ester 5 with an alkylating agent 10 (with an appropriate leaving group (LG) such as halide, mesylate, or tosylate) under standard conditions followed by deprotection of the carboxylic acid ester 11 provides the desired tertiary amino acids III.

As shown in Scheme 4, the tertiary amino acid III may also be assembled through reductive amination first of the $R^{3a}$ aldehyde 12 with an appropriate amine ester hydrochloride 4. The resulting secondary amine-ester 13 then is subjected to reductive amination with appropriate alkyl, aryl or heteroaryl aldehydes 3 (as in Scheme 1) followed by deprotection of the carboxylic acid ester to give the desired amino acid analogs III.

An alternative general synthesis of amino acid analogs II is shown in Scheme 5. A hydroxyaryl or heteroaryl aldehyde 2 is subjected to the usual reductive amination conditions with an appropriate amine-ester hydrochloride 4. The resulting secondary amine-ester 14 is functionalized, in this case by a second reductive amination with aldehyde 6 to furnish the corresponding hydroxy tertiary amine-ester 15. Phenol 15 now undergoes a Mitsunobu reaction with a preferred alcohol 1 ($R^5$—$(CH_2)_nOH$) which is followed by the deprotection of the product, ester 16, to furnish the desired amino acid analogs II.

Scheme 6 illustrates the synthesis of the carbamate-acid analogs IV. The secondary amine-ester 5 can be reacted with appropriate chloroformates 17 under standard literature conditions (optimally in $CH_2Cl_2$ or $CHCl_3$ in the presence of a base such as $Et_3N$) to furnish the corresponding carbamate-esters. The requisite analogs IV are then obtained after deprotection of the carbamate-ester. Alternatively, the secondary amine-ester 5 can be reacted with phosgene to generate the corresponding carbamyl chloride 18. This carbamyl chloride intermediate 18 can be reacted with $R^{3a}$—OH (19; optimally substituted phenols) to afford the corresponding carbamate-acids IV after deprotection.

The secondary amine-ester 5 can be functionalized with substituted aryl or aliphatic carboxylic acids 20, under standard peptide coupling conditions, as illustrated in Scheme 7. The amide bond-formation reactions are conducted using standard peptide coupling procedures known in the art. Optimally, the reaction is conducted in a solvent such as DMF at 0° C. to RT using 1-ethyl-3-(3-dimethylaminopropyl) carbodiimide (EDAC or EDCI or WSC), 1-hydroxybenzotriazole (HOBT) or 1-hydroxy-7-azabenzotriazole (HOAT) and a base, e.g. diisopropylethylamine, N-methyl morpholine or triethylamine. Deprotection of the amide-ester then furnishes the desired amide-acid analogs V.

The secondary amine-ester 5 can also be reacted with aliphatic or aryl isocyanates 21 to provide the corresponding urea-esters. Deprotection of this product provides the desired urea-acid analogs VI, as shown in Scheme 8. Alternatively, as shown in Scheme 9, the carbamyl chloride intermediate 18 described in Scheme 6 can be reacted with appropriate primary or secondary aliphatic or aryl amines 23 and 23 in the presence of a tertiary amine (e.g. $Et_3N$) to furnish tri- or tetrasubstituted urea-acid analogs VII or VIII after deprotection of the ester.

The secondary amine-ester 5 can also be reacted with appropriate sulfonyl chlorides 24 under standard literature conditions (optimally in the presence of a base such as pyridine, either neat or using chloroform as a co-solvent), followed by deprotection, to provide the corresponding sulfonamide-acids IX, as shown in Scheme 10.

The different approaches to the preparation of the preferred racemic α-alkylbenzyl carbamate-acid and amino acid analogs X and XI respectively are exemplified in synthetic Schemes 11 and 12. In Scheme 11 a substituted aryl nitrile (with a suitable aromatic heterocycle $R^5$ already appended) is treated with an appropriate organometallic reagent (e.g. a Grignard reagent $R^{10}MgX$ 26 or an organolithium reagent $R^{10}Li$) under standard conditions to give the corresponding imine intermediate, which is immediately reduced (e.g. with $LiAlH_4$) to give the corresponding primary amine 27. Amine 27 is then reacted with an appropriately substituted α-halo-ester 28 to provide the corresponding α-amine-ester 29. It will be understood that in the amine-ester 29, the moiety

does not necessarily represent two repeating units.

Acylation of the amine-ester 29 with an appropriately substituted aryl or heteroaryl chloroformates 17 followed by deprotection provides the racemic carbamate-acid analogs X. Reductive amination of alkylbenzyl amine-ester 29 with aryl aldehyde 6 followed by deprotection provides the racemic amino-acid analogs XI.

Alternatively (as shown in Scheme 12), a protected aryl or heteroaryl nitrile 30 is treated with an appropriate organometallic reagent (e.g. a Grignard reagent $R^{10}MgX$ 26) to give the corresponding imine intermediate, which is immediately reduced (e.g. with $LiAlH_4$) to give the corresponding primary amine 31. This amine is then reacted with an appropriately substituted α-halo-ester 28 to give the corresponding α-amine-ester 32. This intermediate 32 can then be acylated with an appropriately substituted aryl or heteroaryl chloroformate 17 to provide the corresponding carbamate-ester, whose phenolic functionality is then deprotected to provide the key intermediate phenol 33. Alkylation of the phenol 33 with a halide or mesylate 7 followed by deprotection provides the racemic carbamate-acid analogs X. An analogous sequence, which involves reductive amination of the secondary amino-ester 32 with an aryl or heteroaryl aldehyde 6, then selective phenol deprotection, alkylation with mesylate 7 and a final deprotection, provides the racemic amino acid analogs XI.

A synthesis of chiral carbamate analogs XII and amino acid analogs XIII is shown in Scheme 13. Asymmetric reduction (e.g. using the Corey oxazaborolidine reduction protocol; review: E. J. Corey & C. Helal, *Angew. Chem. Int. Ed. Engl.*, 1998, 37, 1986-2012) of the aryl-ketone 34 provides each of the two desired enantiomeric alcohols 35 (although only one enantiomer is represented in the scheme). Treatment of the chiral alcohol 35 with azide in a Mitsunobu-like reaction (ref: A. S. Thompson et. al., *J. Org. Chem.* 1993, 58, 5886-5888) gives the corresponding chiral azide (with inverted stereochemistry from the starting alcohol). This azide is then reduced to the amine 36 by standard methods (e.g. hydrogenation or $Ph_3P/THF/H_2O$). Treatment of the chiral amine 36 with an α-halo-ester 28 provides the secondary amine-ester 37. Acylation of amino-ester 36 with an aryl or heteroaryl chloroformate 17 followed by deprotection provides the chiral carbamate-acid analogs XII (which may be either enantiomer depending upon the stereochemistry of 36). Reductive amination of alkyl amino-ester 37 with aryl aldehydes 6 followed by deprotection provides the chiral amino-acid analogs XIII (which may be either enantiomer depending upon the stereochemistry of 36).

An alternative synthesis of analogs XII and XIII is shown in Scheme 14. An appropriately protected oxyaryl ketone 38 undergoes asymmetric reduction to give the chiral alcohol 39. This is converted to the chiral amine 40 via the identical sequence as in Scheme 13 (via the chiral azide). Treatment of the chiral amine 40 with an ester 28 (LG=halogen or mesylate) gives the corresponding secondary amino-ester 41. Acylation of 41 with an aryl or heteroaryl chloroformate 17 provides the corresponding carbamate-ester. Selective deprotection furnishes the free phenol carbamate-ester 42. Alkylation of the phenol 42 with a halide or mesylate 7 followed by deprotection provides the chiral carbamate-acid analogs XII. An analogous sequence which involves reductive amination of the secondary amine-ester 41 with an aryl or heteroaryl aldehyde 6, then selective deprotection, alkylation with 7 and a final deprotection, provides the chiral amino acid analogs XIII. It will be appreciated that either the (R)— or (S)-enantiomer of X or XI may be synthesized in Schemes 13 and 14, depending upon the chirality of the reducing agent employed.

A preferred alternative asymmetric synthesis of carbamate-acids XII is shown in Scheme 15. Protection of a chiral amine 43 (with the phenol differently protected), preferably as a carbamate, provides intermediate 44. Selective removal of the phenolic protecting group of 44 provides the free phenol 45. Alkylation of phenol 45 with the mesylate 7 furnishes the protected amine 46. Deprotection of the amine of 45 then furnishes the key intermediate, the primary amine-ester 36, which then undergoes alkylation with a α-halo-ester 28 in the presence of base to provide the secondary amine 37. Reaction of amine 37 with a chloroformate 17 provides the chiral carbamate acid analogs XII.

A preferred asymmetric synthesis of analogs XIV and XV is shown in Scheme 16. The aldehyde 3 is subjected to standard Wittig reaction conditions (ref: Preparation of Alkenes, a Practical Approach, J. J. Williams, Ed., Chapter 2, pp 19-58) to furnish the alkene 47. Asymmetric aminohydroxylation according to known literature procedures (ref: O'Brien, P., *Angew. Chem. Int. Ed.*, 1999, 38, 326 and Reddy, K. L., and Sharpless, K. B., *J. Am. Chem. Soc.*, 1998, 120, 1207) furnishes the desired amino-alcohol 48 as a single enantiomer. It is understood that this reaction can produce either enantiomer (of which only one is shown here). Selective protection of the amine 48 provides the alcohol 49. Alcohol 49 is then converted by standard methods to the intermediate 50, which contains a suitable leaving group (either a halide or a mesylate) for the subsequent cuprate displacement reaction. Reaction of an appropriate higher-order cuprate 51 (ref: L. A. Paquette, Ed., *Organic Reactions*, 1992, Vol. 41, J. Wiley & Sons) with the protected amine substrate 50 provides the coupled, protected amine 52. Deprotection of the amine functionality of 52, followed by reaction with an ester 28 (LG=halogen or mesylate), furnishes the corresponding secondary amino-ester 53. Acylation of amine 53 with an aryl or heteroaryl chloroformate 17 provides the corresponding carbamate-ester, which is then deprotected to furnish the carbamate-acid analogs XIV. Alternatively, reductive amination of amine 53 with an aldehyde 6 followed by deprotection provides the tertiary amino acid analogs XV.

The synthesis of carbon-linked analogs are shown in Schemes 17-19. Scheme 17 describes a general synthesis of the acetylene-linked acids XVI and the alkyl-linked acids XVII. A halo-substituted aryl aldehyde 54 (preferably iodide or bromide) is subjected to reductive amination using procedures known in the literature (e.g. Abdel-Magid et al, *J. Org. Chem*. 1996, 61, 3849) with an α-amino acid ester hydrochloride V. The resulting secondary amino-ester 55 is then reacted with an aryl or heteroaryl chloroformate 17 in the presence of an appropriate base (e.g. pyridine or triethylamine) to furnish the corresponding halo-aryl carbamate-ester 56. Aryl halide 56 is then reacted with an appropriate heteroaryl ($R^5$)-substituted acetylene 57 in the presence of an appropriate palladium catalyst (e.g. $(Ph_3P)_2PdCl_2$) and a copper (I) salt (e.g. CuI) in a Sonogashira coupling reaction (ref: Organocopper Reagents, a Practical Approach, R. J. K. Taylor, Ed., Chapter 10, pp 217-236, Campbell, I. B., Oxford University Press, 1994) to furnish the key intermediate, arylacetylene 58. The arylacetylene ester 58 is deprotected to provide the corresponding arylacetylene acid analogs XVI. The acetylene moiety of 58 can be reduced by standard methods (e.g. hydrogenation, ref: M. Hudlicky, Reductions in Organic Chemistry, $2^{nd}$ Edition, ACS, 1996, Chapter 1) to furnish the corresponding fully saturated alkyl aryl carbamate esters, which are then deprotected to give the alkyl aryl carbamate acid analogs XVII.

Stereoselective reduction of the acetylene ester 58 by standard methods (e.g. Lindlar's catalyst; ref: Preparation of Alkenes, A Practical Approach, J. J. Williams, Ed., Chapter 6, pp 117-136, Oxford University Press, 1996) can be achieved to provide the corresponding cis-alkenyl aryl carbamate-ester, which is then deprotected to furnish the Z-alkenyl aryl carbamate acid analogs XVIII (Scheme 18). Alternatively, this sequence can be reversed, i.e. the initial step being the deprotection of acetylenic ester 58 to the acetylenic acid, followed by stereoselective reduction of the acetylene moiety to provide the Z-alkene-acid analogs XVIII.

The corresponding trans-alkenyl aryl carbamate acids XIX are synthesized according to the general route in Scheme 19. A heteroaryl ($R^5$)-acetylene 57 is halogenated under standard conditions (ref: Boden, C. D. J. et al., *J. Chem. Soc. Perkin Trans. I*, 1996, 2417; or Lu, W. et. al., *Tetrahedron Lett*. 1998, 39, 9521) to give the corresponding halo-acetylene, which is then converted to the corresponding trans-alkenyl stannane 59 (ref: Boden, C. D. J., *J. Chem. Soc., Perkin Trans. I*, 1996, 2417). This aryl- or heteroaryl-substituted trans-alkenyl stannane 59 is then coupled with the halo-aryl carbamate ester 56 under standard Stille coupling conditions (ref: Farina, V. et. al., "The Stille Reaction", *Organic Reactions*, 1997, 50, 1) to furnish the corresponding trans-alkenyl aryl carbamate ester 60. This carbamate-ester is then deprotected under standard conditions to give the desired trans-alkenyl aryl carbamate acid analogs XIX.

In Scheme 20, treatment of a suitably protected halo-aryl carbamate-ester 56 with a metallating agent (e.g. isopropyl magnesium bromide, reference: P. Knochel et al., *Synthesis*, 2002, 565-569) furnishes the corresponding arylmagnesium reagent, which is then reacted with formaldehyde to provide benzyl alcohol 61. Treatment of alcohol 61 with mesylate VIII in the presence of base provides the corresponding ether-carbamate ester, which is then deprotected to furnish the ether-acid XX of the invention.

In Scheme 21, treatment of a suitably protected halo-aryl carbamate-ester 56 with an appropriate vinyl tin reagent (e.g. tributylvinyltin) under Stille coupling conditions (reference: Farina, V., Krishnamurthy, V., and Scott, W. J., *Organic Reactions*, 1997, 50, 1) provides the corresponding vinyl intermediate, which can then undergo hydroboration (e.g. borane-THF) to give the alcohol 62. Treatment of alcohol 62 with mesylate VIII in the presence of base provides the corresponding ether carbamate-ester, which is then deprotected to provide the ether acid XXI of the invention.

The synthesis of N-aryl acids XXII of the invention is shown in Scheme 22. Reductive amination of protected phenol-aldehyde 2 with an appropriate aniline 63 (or other heteroarylamine) provides the substituted aromatic amine intermediate 64. N-alkylation of the aromatic amine 64 with an appropriate halo-substituted ester 65 in the presence of base (e.g. sodium hexamethyldisilazide) provides the N-aryl (or heteroaryl) ester 66. Deprotection of the phenol of amino-ester 66 provides free phenol 67, which then undergoes Mitsunobu reaction (e.g. using cyanomethylene tributylphosphorane) With an appropriate alcohol 1 to provide the alkylated phenol N-aryl amino-ester 68. Deprotection of the ester 68 provides N-aryl (or N-heteroaryl) acids XXII of the invention. Alternatively, phenol 67 can be alkylated with mesylate 7 in the presence of base (e.g. $K_2CO_3$) followed by acid deprotection to also provide N-aryl (or N-heteroaryl) acids XXII of the invention.

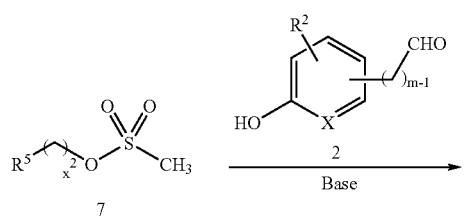

Scheme 1

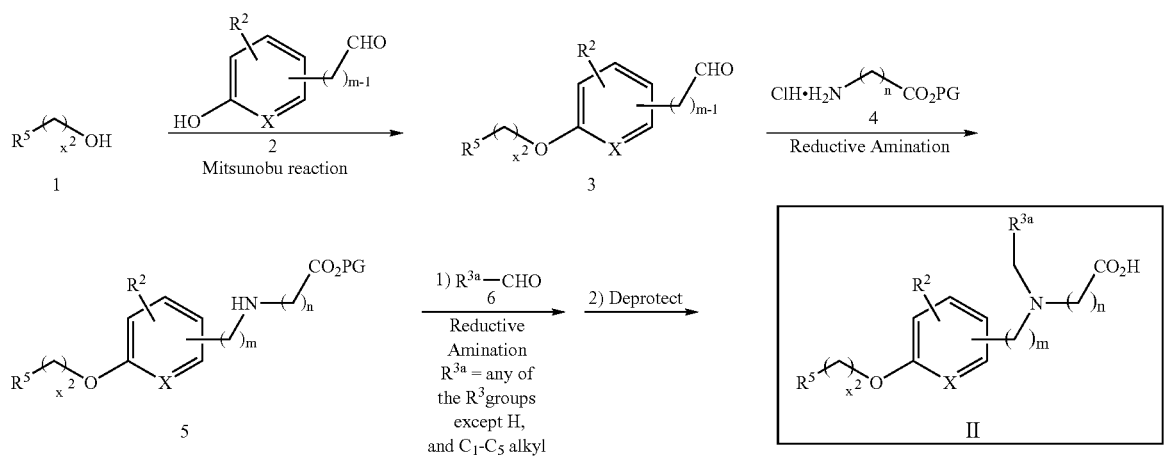

In this and the following Reaction Schemes:

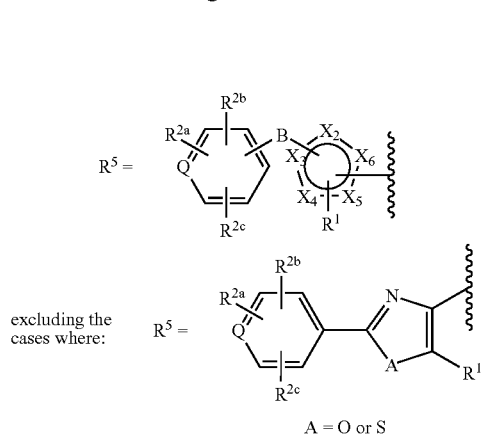

A = O or S

Alternative Scheme 1A for Preparing Aldehyde IV

SCHEME 1A

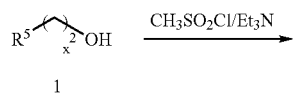

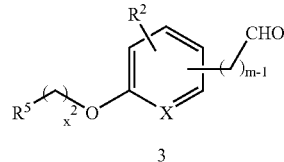

Scheme 2

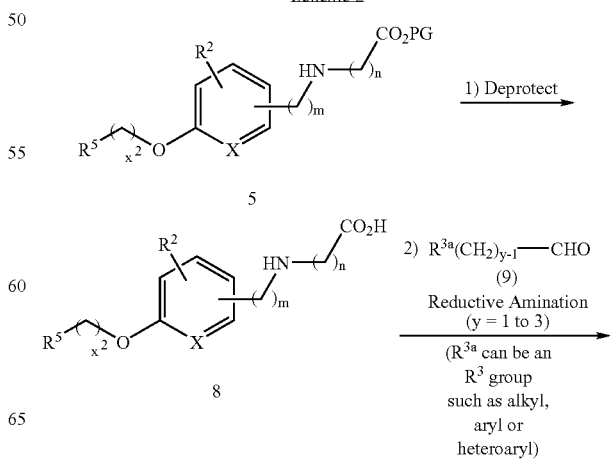

-continued
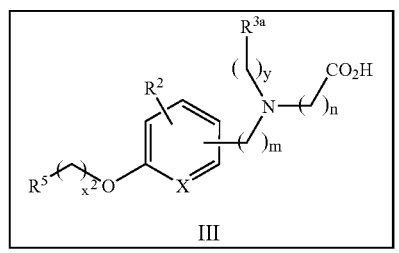
III
Scheme 3
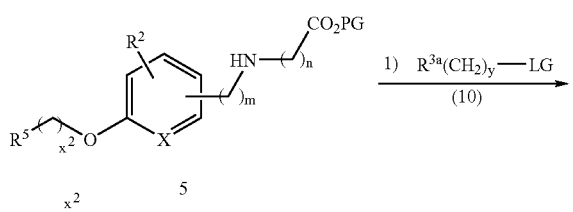
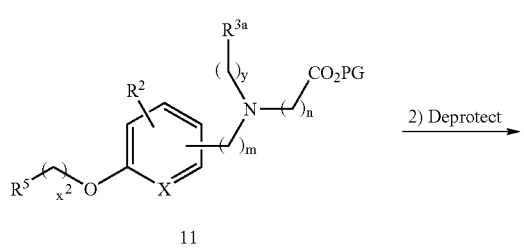
y = 1-3
LG = leaving group, eg halide, tosylate, etc.
III
Scheme 4
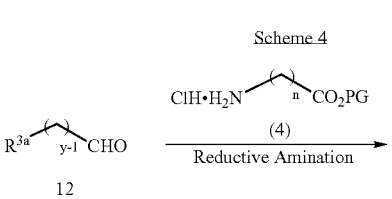
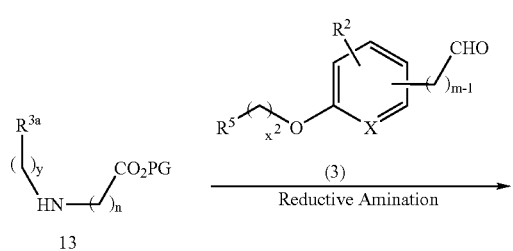
-continued
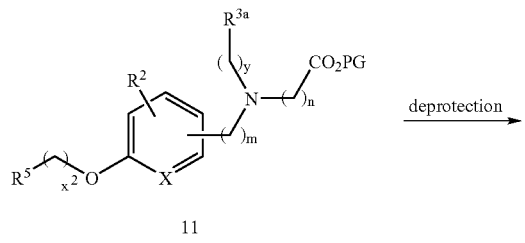
11 → deprotection
III
Scheme 5
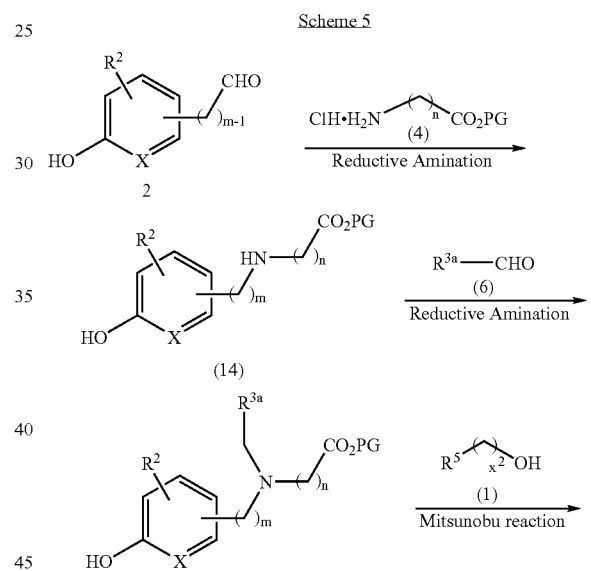
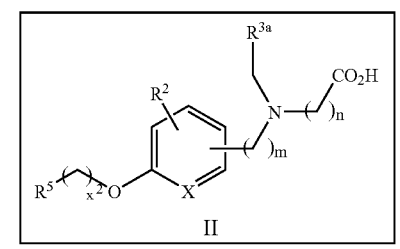
II Scheme 6
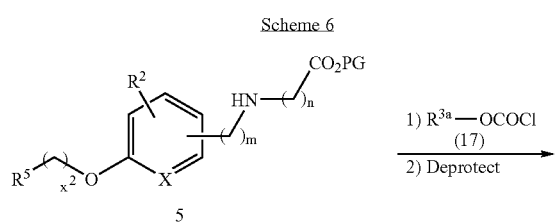
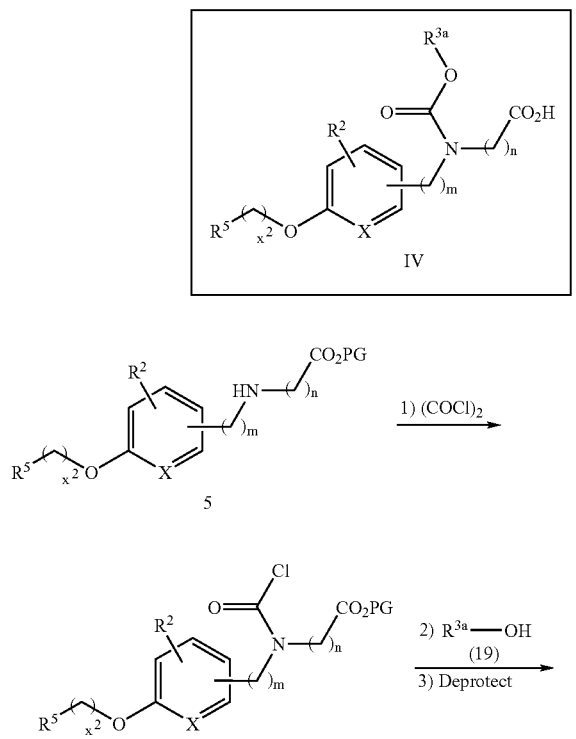
Scheme 7
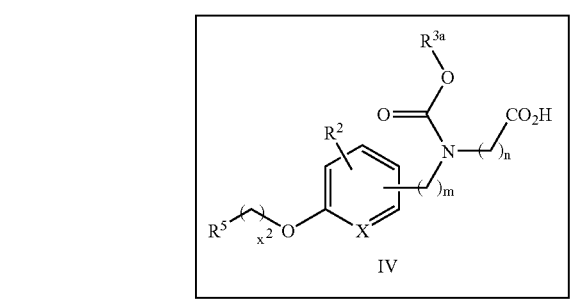
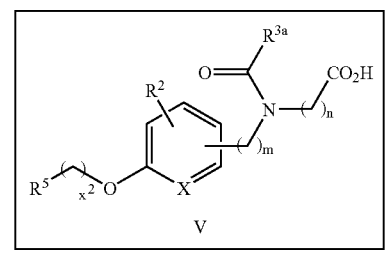
Scheme 8
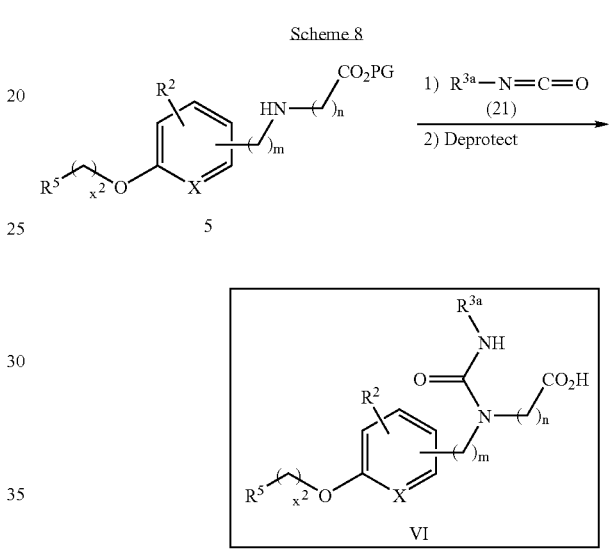
Scheme 9
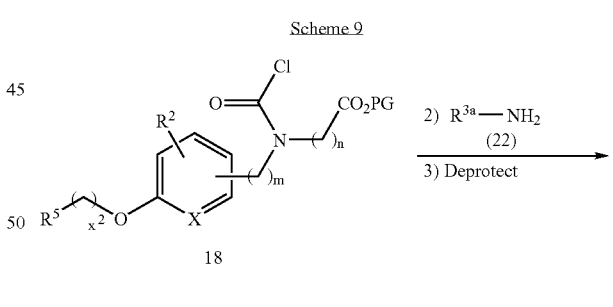
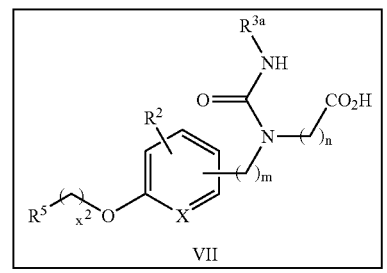

-continued
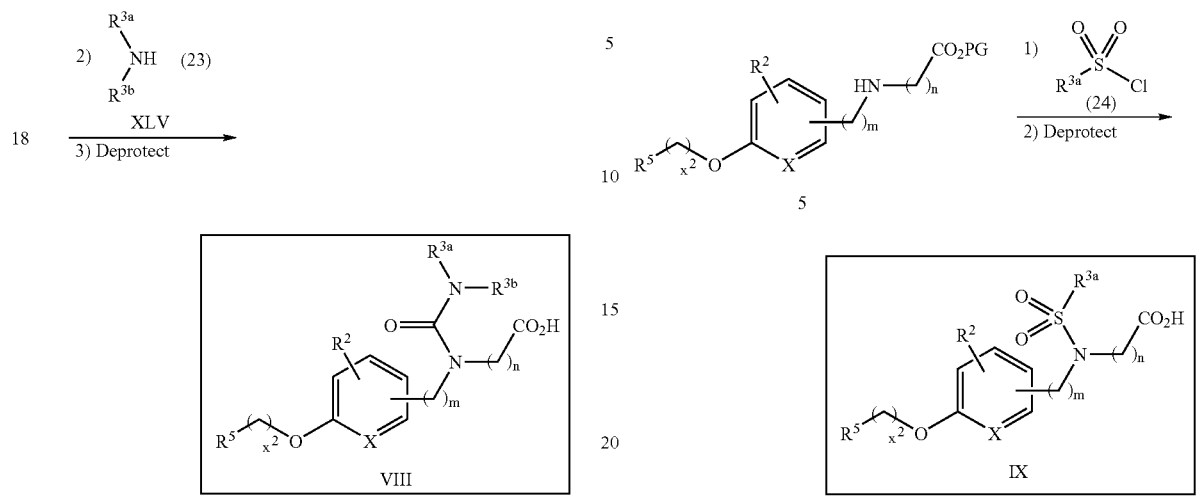
Scheme 10
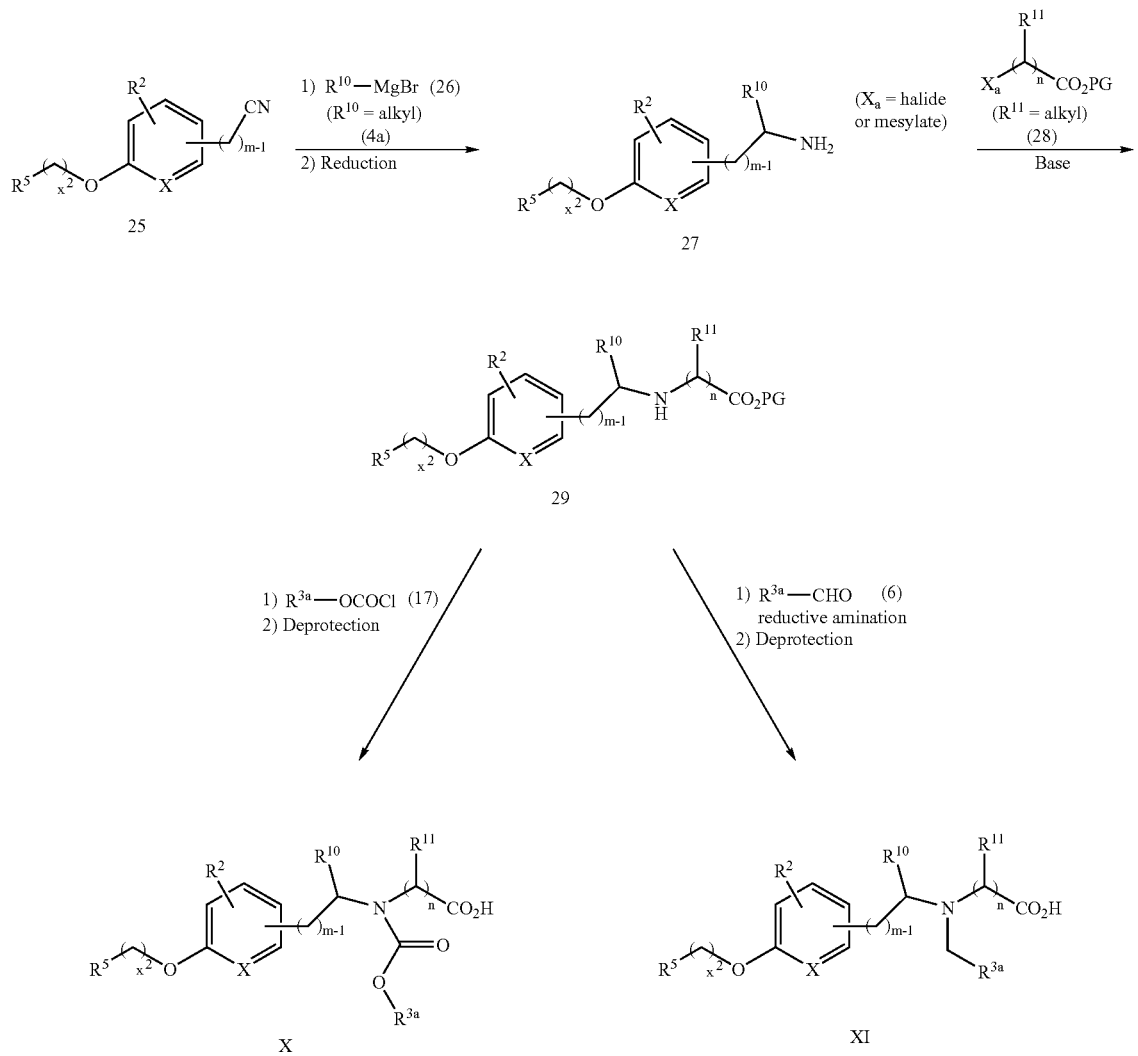
Scheme 11

Scheme 12
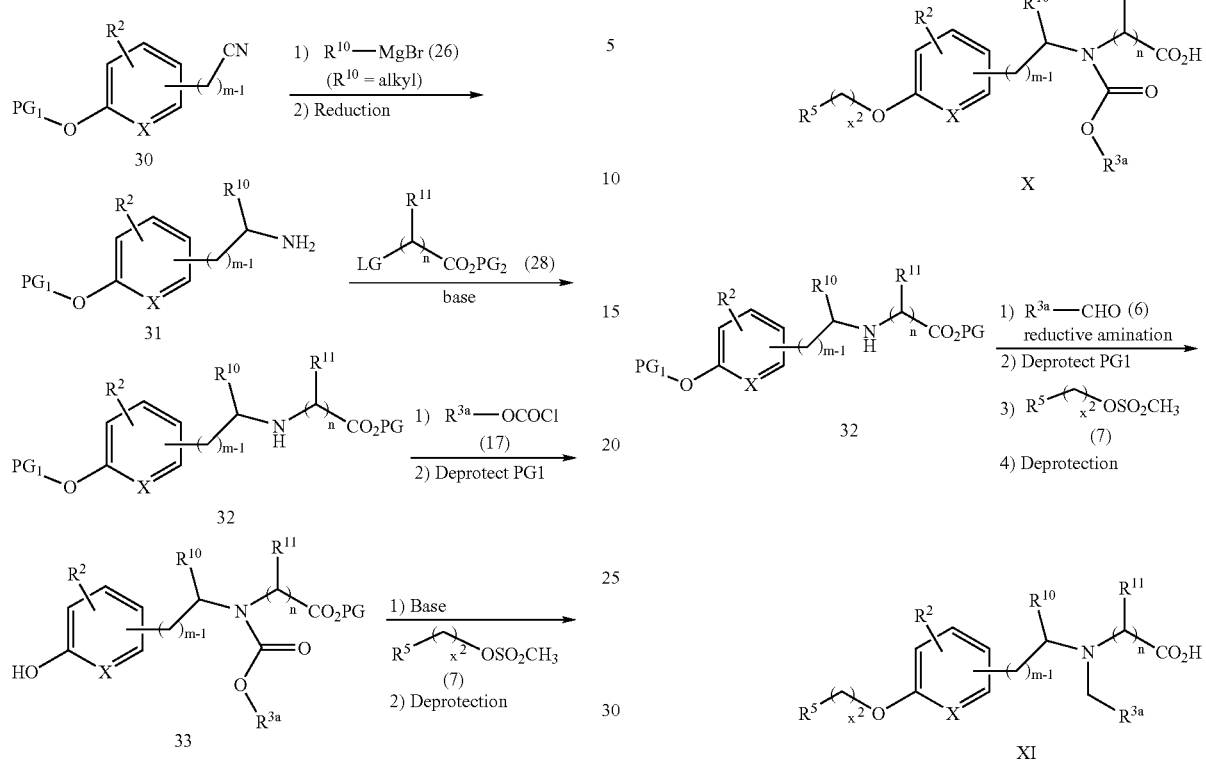
Scheme 13
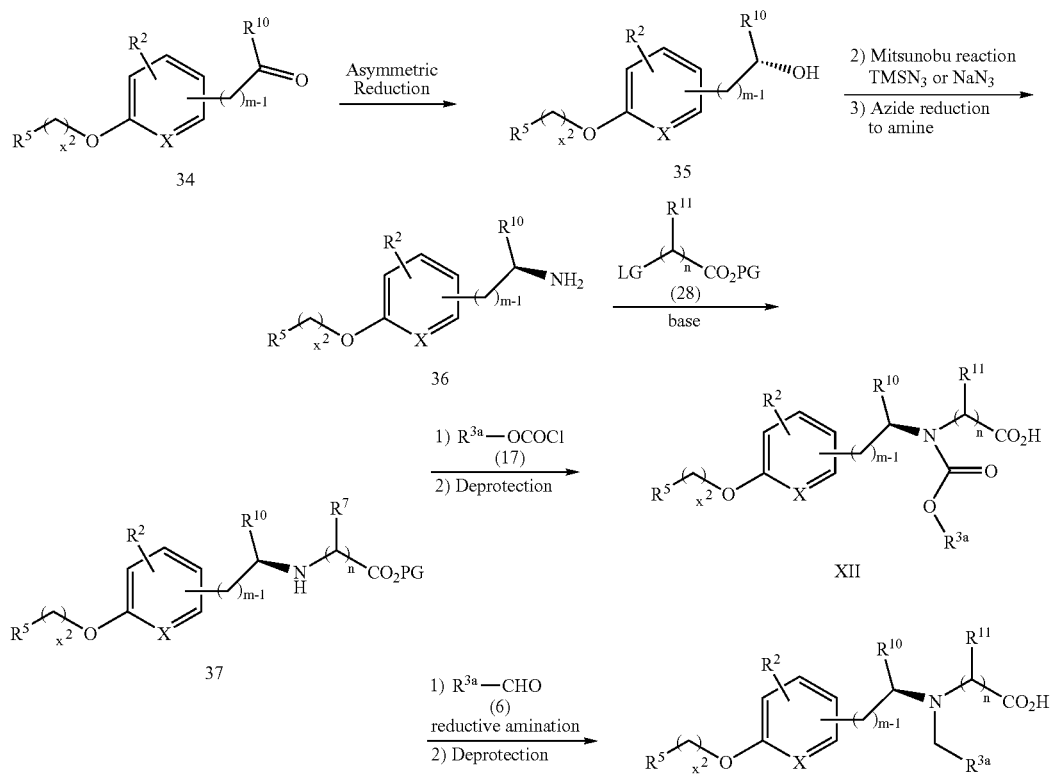

Scheme 14
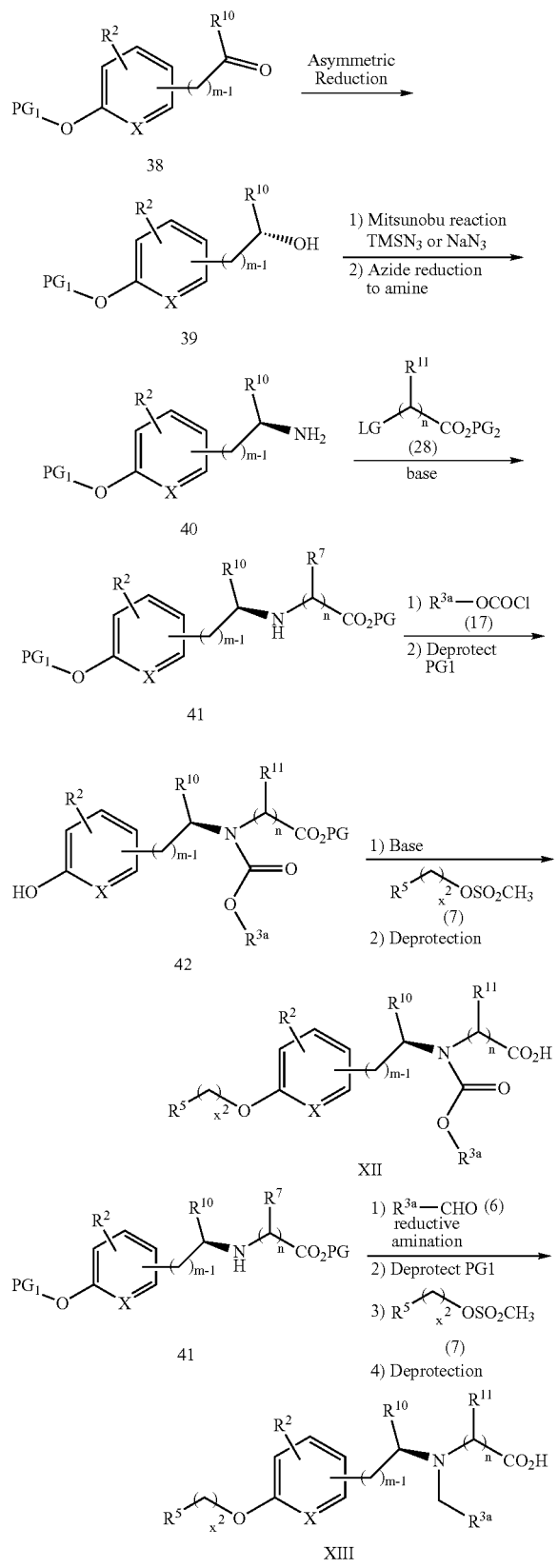
Scheme 15
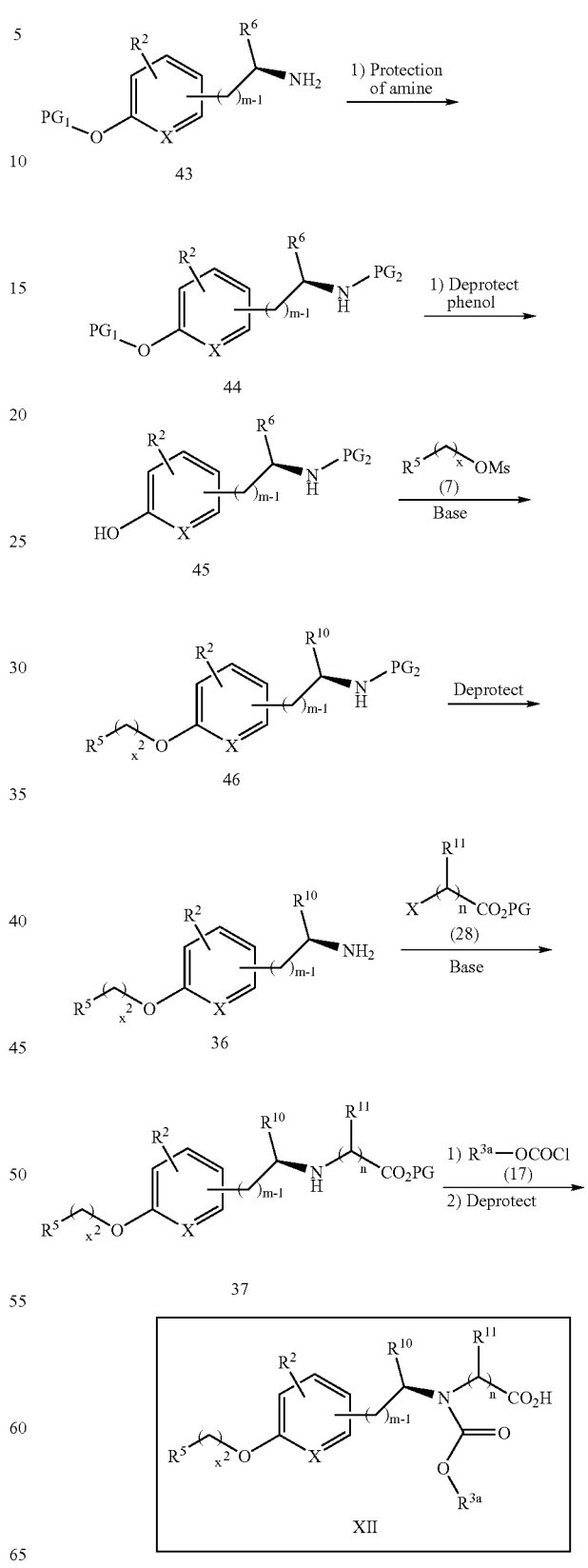

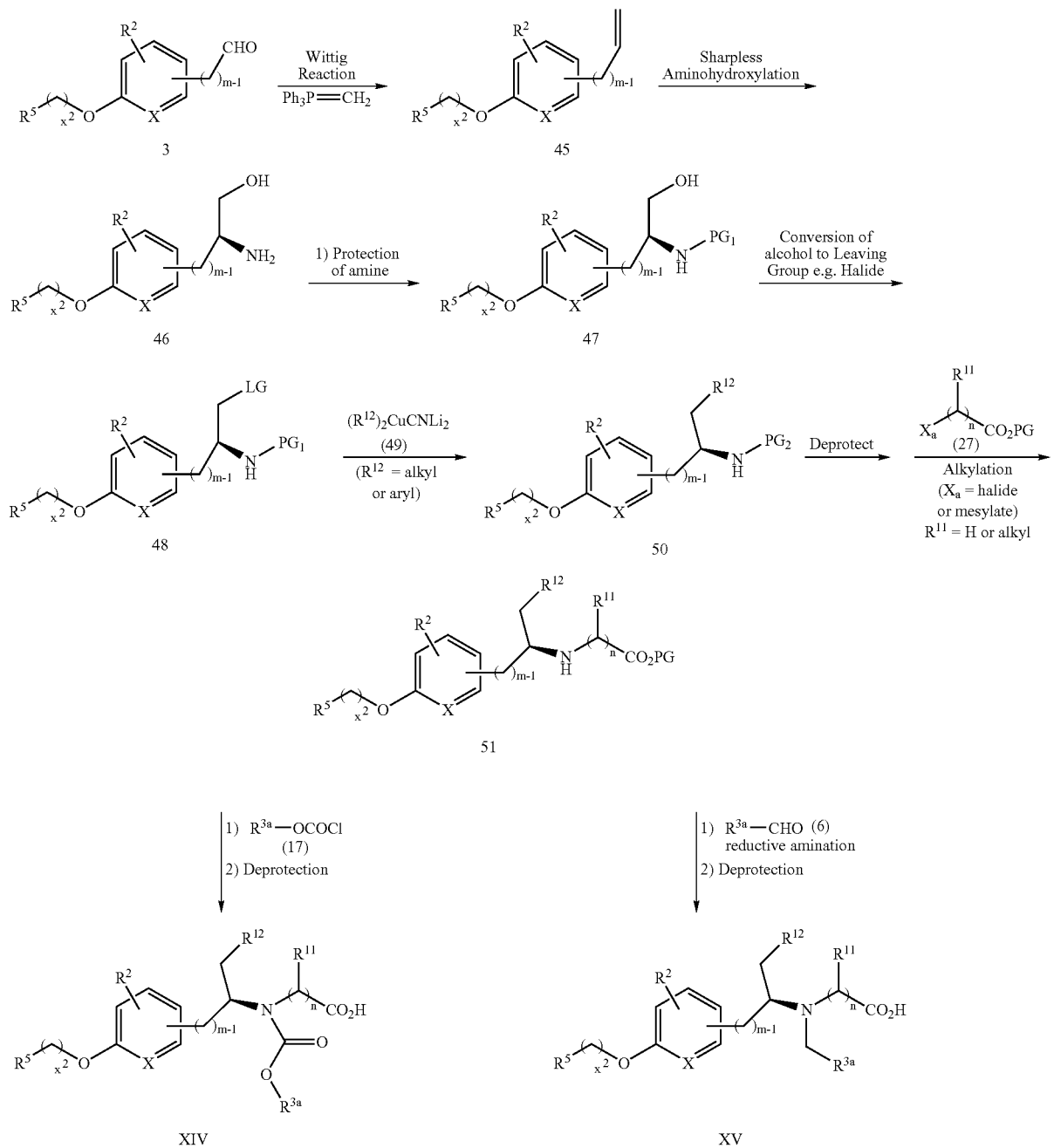
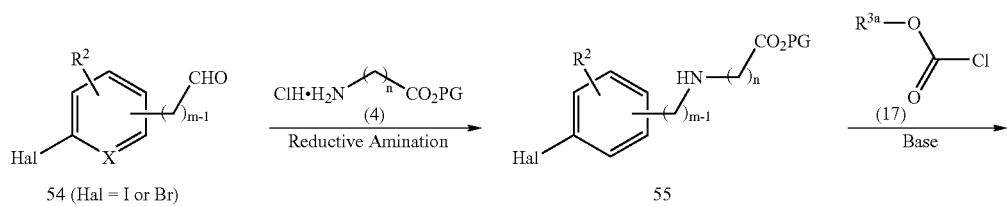

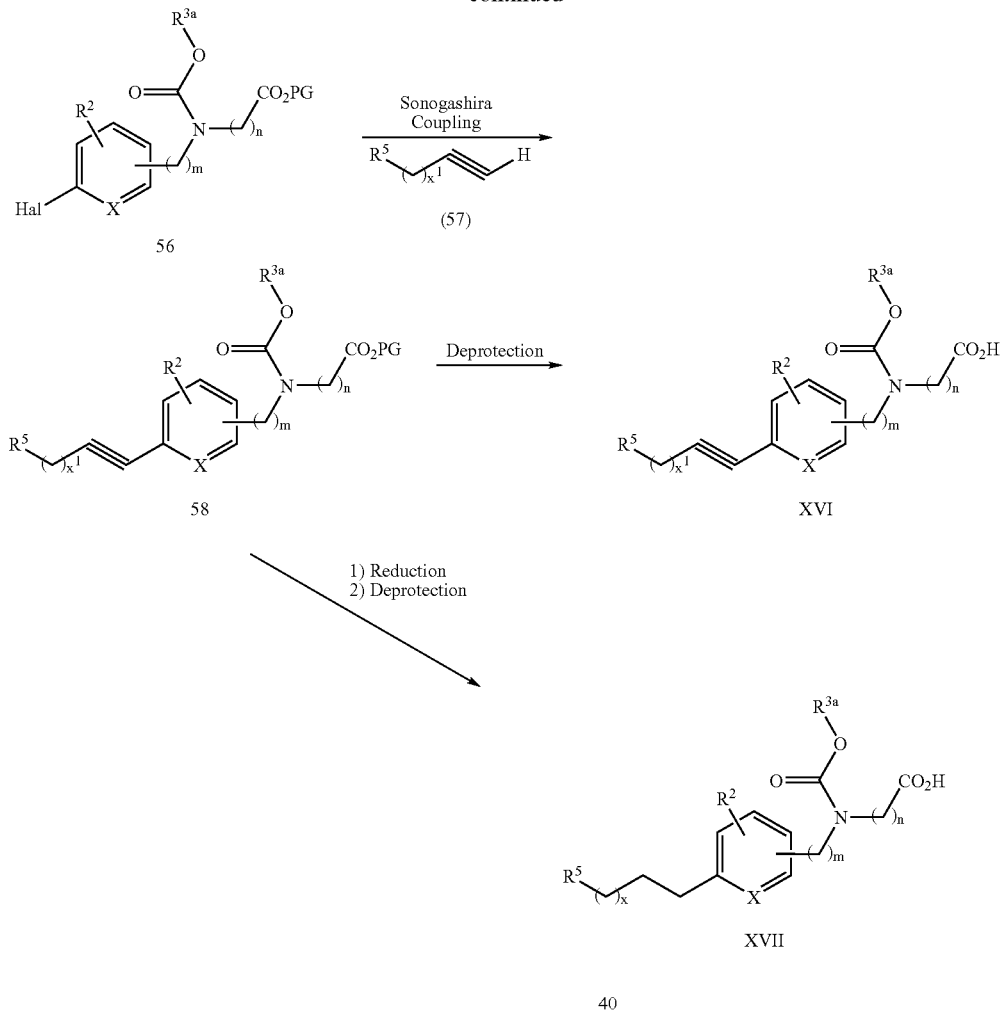
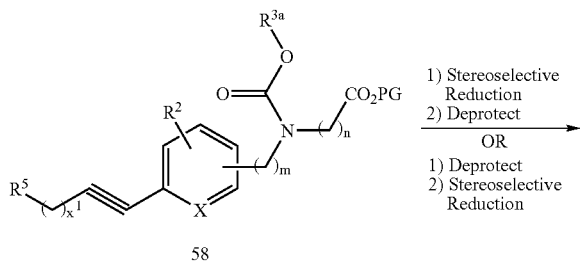
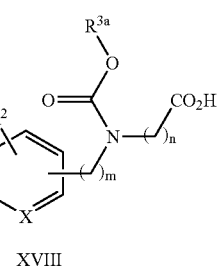
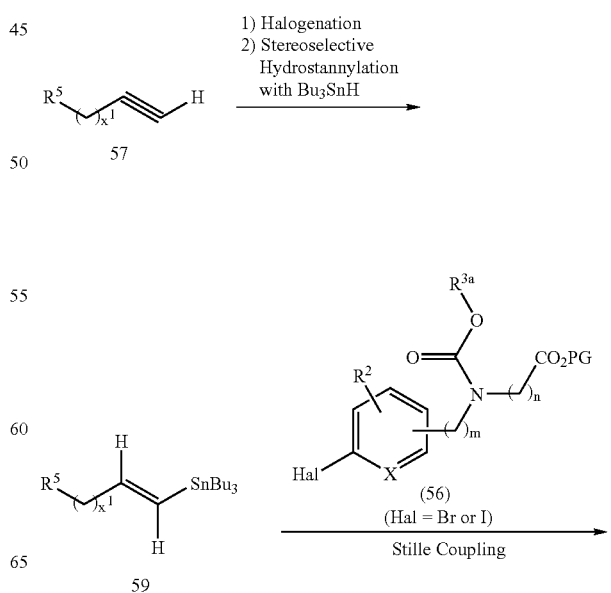

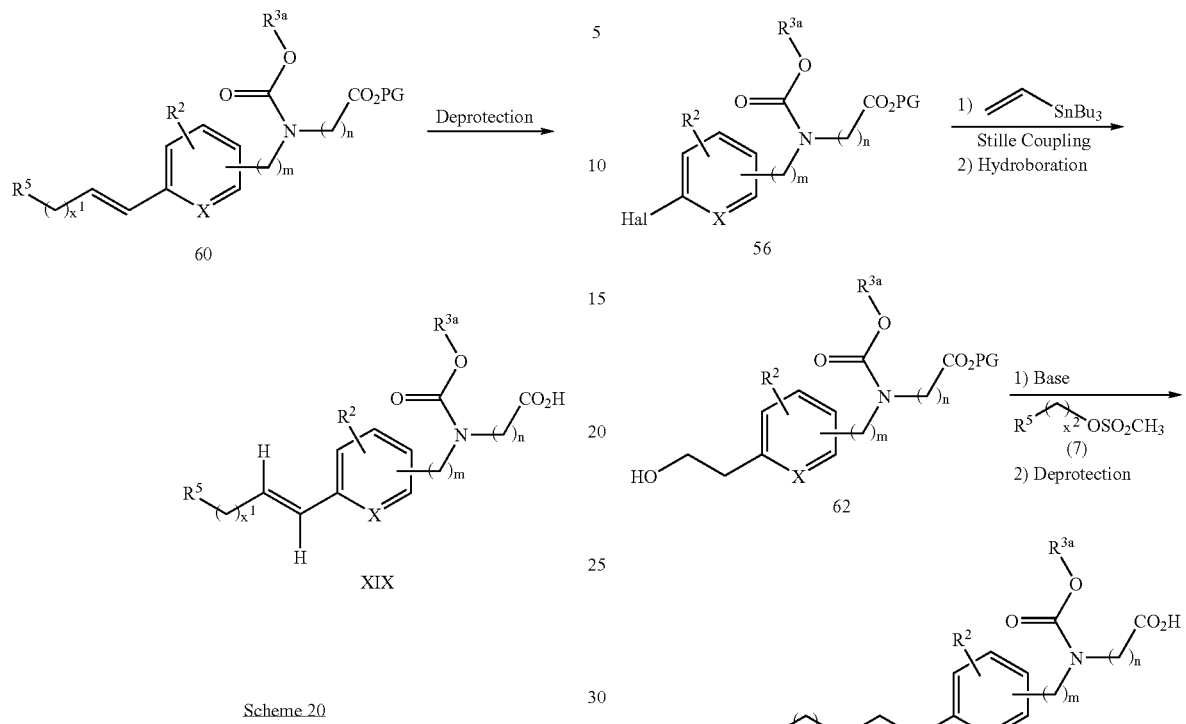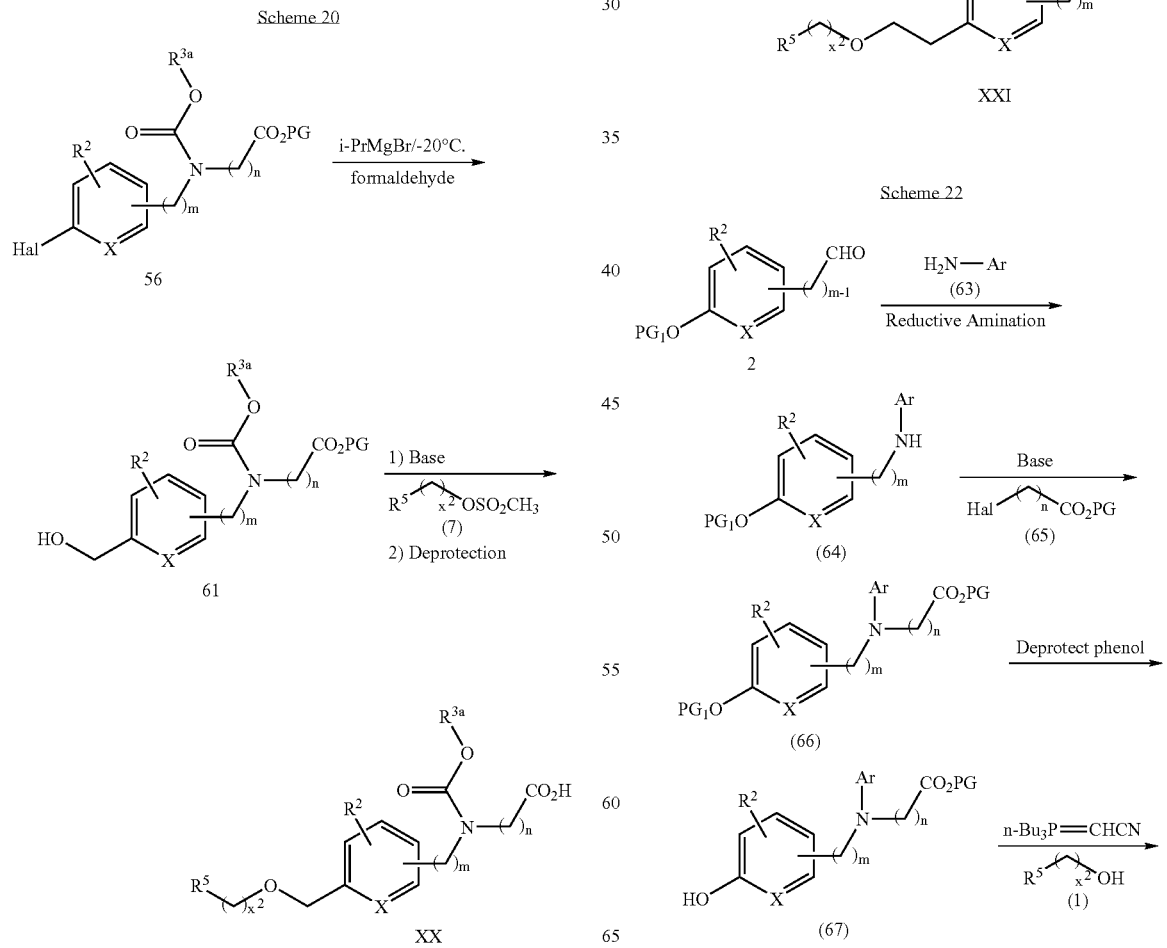

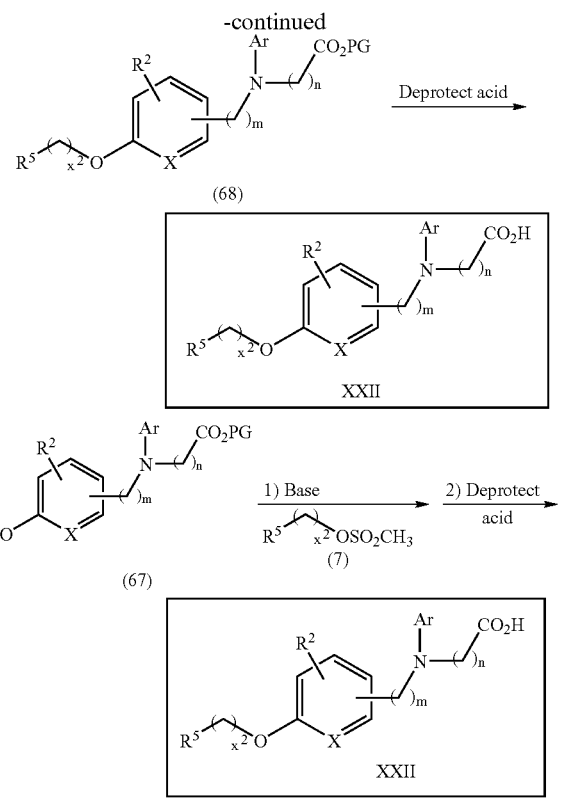

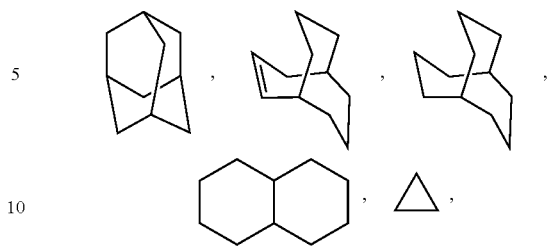

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

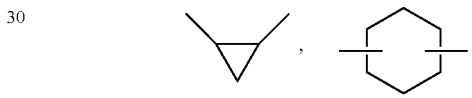

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, and may optionally include an oxygen or nitrogen in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the substituents for alkyl set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, and may optionally include an oxygen or nitrogen in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, and may optionally include an oxygen or nitrogen in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio and/or any of the $R^3$ groups.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the substituents for alkyl set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

$(CH_2)_x$, $(CH2)_x^1$, $(CH_2)_x^2$, $(CH_2)_x^3$ $(CH_2)_x^4$, $(CH_2)_m$ or $(CH_2)_n$ includes alkylene, allenyl, alkenylene or alkynylene groups, as defined herein, each of which may optionally include an oxygen or nitrogen in the normal chain, which may optionally include 1, 2, or 3 substituents which include alkyl, alkenyl, halogen, cyano, hydroxy, alkoxy, amino, thioalkyl, keto, $C_3$-$C_6$ cycloalkyl, alkylcarbonylamino or alkylcarbonyloxy; the alkyl substituent may be an alkylene moiety of 1 to 4 carbons which may be attached to one or two carbons in the $(CH_2)_x$, $(CH_2)_x^1$, $(CH_2)_x^2$, $(CH_2)_x^3$, $(CH_2)_x^4$, $(CH_2)_m$ or $(CH_2)_n$ group to form a cycloalkyl group therewith.

Examples of $(CH_2)_x$, $(CH_2)_x^1$, $(CH_2)_x^2$, $(CH_2)_x^3$ $(CH_2)_x^4$ $(CH_2)_m$, $(CH_2)_n$, alkylene, alkenylene and alkynylene include

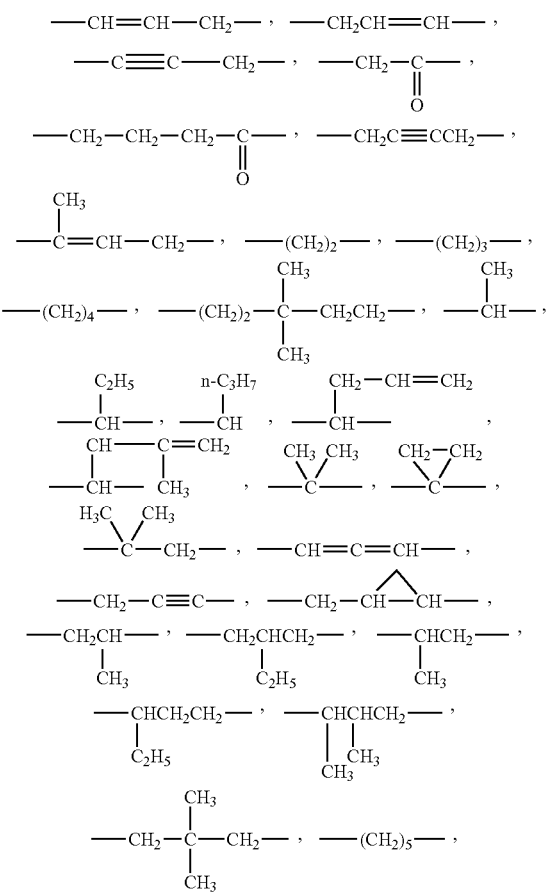

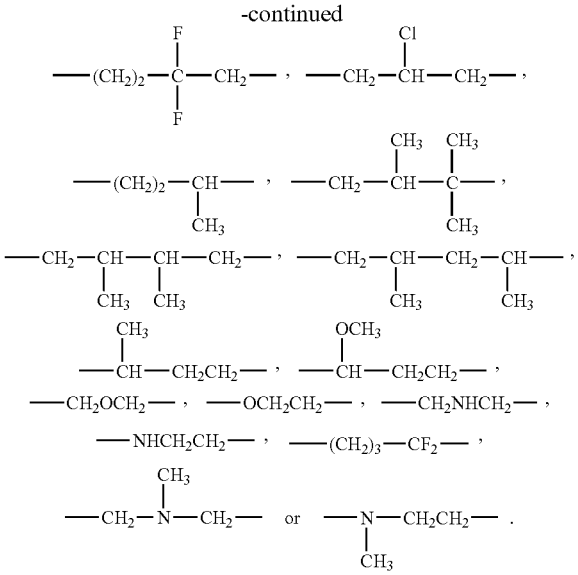

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" or the group

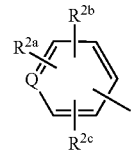

where Q is C, as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

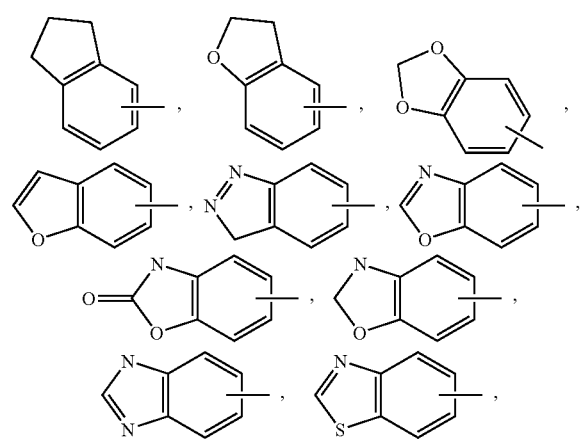

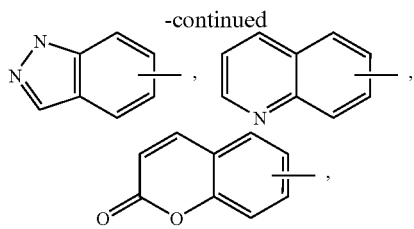,

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the substituents for alkyl set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", "alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl group; examples of acyl groups include any of the $R^3$ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 1, 2 or 3), such as

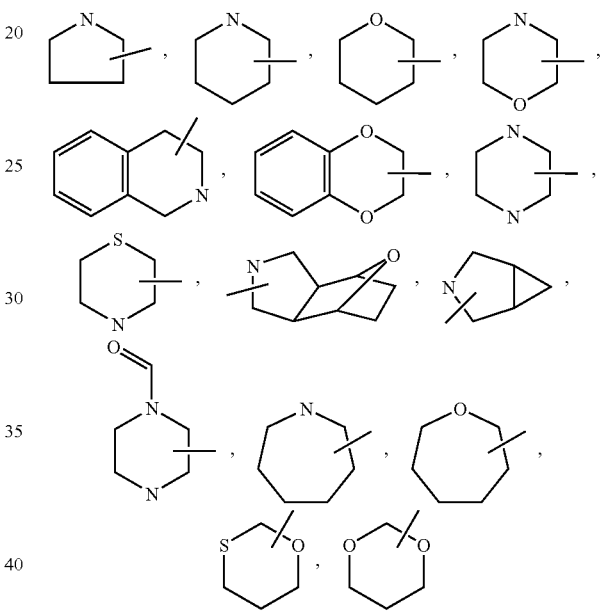

and the like. The above groups may include 1 to 4 substituents such as alkyl, halo, oxo and/or any of of the substituents for alkyl or aryl set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring including

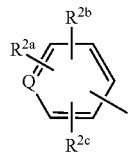

where Q is N, which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the the substituents for alkyl or aryl set out above. Examples of heteroaryl groups include the following:

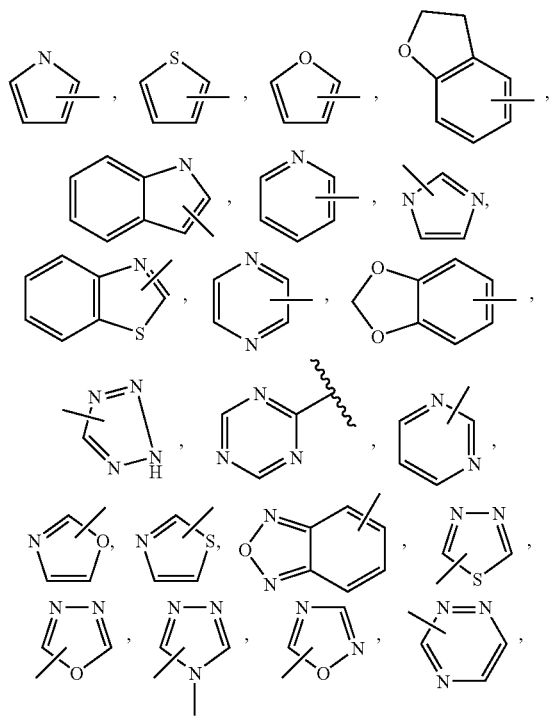

and the like.

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a —$(CH_2)_p$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "prodrug esters" as employed herein includes prodrug esters which are known in the art for carboxylic and phosphorus acid esters such as methyl, ethyl, benzyl and the like. Other prodrug ester examples of $R^4$ include the following groups: (1-alkanoyloxy)alkyl such as,

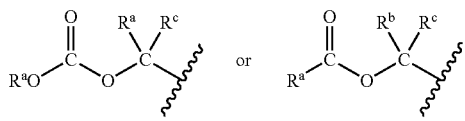

wherein $R^a$, $R^b$ and $R^c$ are H, alkyl, aryl or arylalkyl; however, $R^aO$ cannot be HO.

Examples of such prodrug esters $R^4$ include

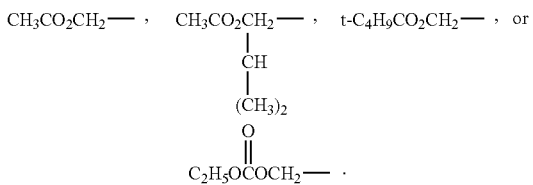

Other examples of suitable prodrug esters $R^4$ include

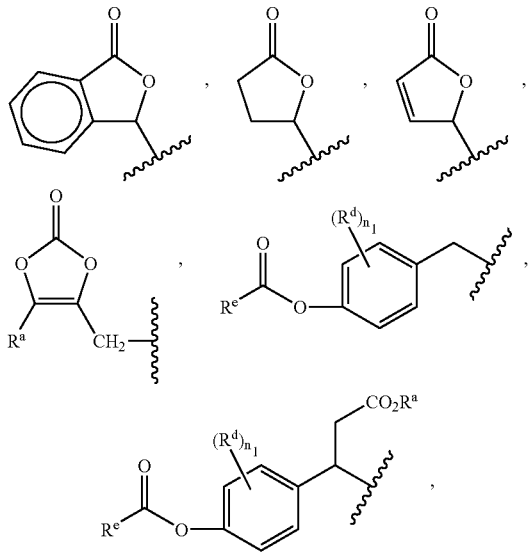

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

Where the compounds of structure I are in acid form they may form a pharmaceutically acceptable salt such as alkali metal salts such as lithium, sodium or potassium, alkaline earth metal salts such as calcium or magnesium as well as zinc or aluminum and other cations such as ammonium, choline, diethanolamine, lysine (D or L), ethylenediamine, t-butylamine, t-octylamine, tris-(hydroxymethyl)aminomethane (TRIS), N-methyl glucosamine (NMG), triethanolamine and dehydroabietylamine.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Where desired, the compounds of structure I may be used in combination with one or more hypolipidemic agents or lipid-lowering agents and/or one or more other types of therapeutic agents including antidiabetic agents, anti-obesity agents, antihypertensive agents, platelet aggregation inhibitors, and/or anti-osteoporosis agents, which may be administered orally in the same dosage form, in a separate oral dosage form or by injection.

The hypolipidemic agent or lipid-lowering agent which may be optionally employed in combination with the compounds of formula I of the invention may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and 5,760,246.

The most preferred MTP inhibitor is 9-[4-[4-[[2-(2,2,2-Trifluoroethoxy)benzoyl]amino]-1-piperidinyl]butyl]-N-(2,2,2-trifluoroethyl)-9H-fluorene-9-carboxamide

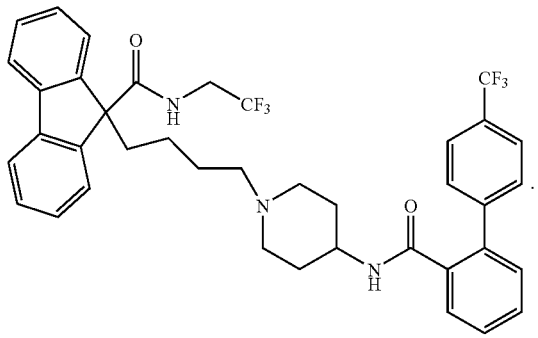

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl]pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322.

In addition, phosphonic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277, 082 and CL-283, 546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future 24, 9-15 (1999), (Avasimibe); "The ACAT inhibitor, Cl -1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl) methyl]ureas with enhanced hypocholesterolemic activity", Stout et al, Chemtracts: Org. Chem. (1995), 8(6), 359-62, or TS-962 (Taisho Pharmaceutical Co. Ltd) as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 (ezetimibe) as well as those disclosed in Atherosclerosis 115, 45-63 (1995) and J. Med. Chem. 41, 973 (1998).

The hypolipidemic agent may be an ileal $Na^+$/bile acid cotransporter inhibitor such as disclosed in Drugs of the Future, 24, 425-430 (1999).

The lipid-modulating agent may be a cholesteryl ester transfer protein (CETP) inhibitor such as Pfizer's CP 529,414 as well as those disclosed in WO/0038722 (i.e. (torcetrapib) and in EP 818448 (Bayer) and EP 992496 and Pharmacia's SC-744 and SC-795, as well as CETi-1 and JTT-705.

The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR alpha agonist and/or an FXR agonist; a PPAR delta agonist (e.g. GW-501516, ref: Oliver, Jr., W. R., et. al, *Proc. Nat. Acad. Sci. USA*. 2001, 98, 5306-5311), an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or rosuvastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or rosuvastatin as well as niacin and/or cholestagel.

The other antidiabetic agent which may be optionally employed in combination with the compound of formula I may be 1,2,3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPARγ agonists such as thiazolidinediones, PPARα agonists such as fibric acid derivatives, PPARδ agonists or antagonists, PPARα/γ dual agonists, aP2 inhibitors, dipeptidyl peptidase IV (DP4) inhibitors, SGLT2 inhibitors, glycogen phosphorylase inhibitors, glucagon-like peptide-1 (GLP-1), PTP-1B (protein tyrosine phosphatase-1B) inhibitors, 11β-HSD 1 (11β-hydroxy-steroid dehydrogenase 1) inhibitors and/or meglitinides, as well as insulin.

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as rosiglitazone (Glaxo SmithKline), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 or balaglitazone (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AZ-242/tesaglitazar (Astra/Zeneca; as described: in B. Ljung et. al., *J. Lipid Res.*, 2002, 43, 1855-1863), GW-409544 (Glaxo-Wellcome), KRP-297/MK-767 (Kyorin/Merck; as described in: K. Yajima et. al., *Am. J. Physiol. Endocrinol. Metab.*, 2003, 284: E966-E971) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998) or the compounds (from Bristol-Myers Squibb) described in U.S. Pat. No. 6,414,002.

The antidiabetic agent may be an SGLT2 inhibitor such as disclosed in U.S. provisional application No. 60/158,773, filed Oct. 12, 1999, employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. provisional application No. 60/127,745, filed Apr. 5, 1999, employing dosages as set out herein. Preferred are the compounds designated as preferred in the above application.

The antidiabetic agent may be a DP4 (Dipeptidyl peptidase IV) inhibitor such as disclosed in Provisional Application 60/188,555 filed Mar. 10, 2000 WO 99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597-11603, 1999, TSL-225 (tryptophyl-1,2,3,4-tetrahydro-isoquinoline-3-carboxylic acid (disclosed by Yamada et al, Bioorg. & Med. Chem. Lett. 8 (1998) 1537-1540, 2-cyanopyrrolidides and 4-cyanopyrrolidides as disclosed by Ashworth et al, Bioorg. & Med. Chem. Lett., Vol. 6, No. 22, pp 1163-1166 and 2745-2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a melanocortin receptor (MC4R) agonist, a melanin-concentrating hormone receptor (MCHR) antagonist, a growth hormone secretagogue receptor (GHSR) antagonist, an orexin receptor antagonist, a CCK (cholecystokinin) agonist, a GLP-1 agonists, NPY1 or NPY5 antagonist, a corticotropin releasing factor (CRF) antagonist, a histamine receptor-3 (H3) modulator, a PPARγ modulator, a PPARδ modulator, a beta 3 adrenergic agonist, a lipase inhibitor, a serotonin (and dopamine) reuptake inhibitor, a erotonin receptor agonist (e.g. BVT-933), an aP2 inhibitor, a thyroid receptor agonist and/or an anorectic agent.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or CNTF/axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), GB98/284425 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be fenfluramine, dexfenfluramine, fluxoxamine, fluoxetine, paroxetine, sertraline, chlorphentermine, clorofex, clortermine, picilorex, sibutramine, dexamphetamine, phentermine, phenylpropanolamine or mazindol. Other anorectic agents which may be optionally employed in combination with a compound of formula I include CNTF (ciliary neurotrophic factor)/Axokine (Regeneron), BDNF (brain-derived neurotrophic factor), leptin or cannabinoid receptor antagonists, such as SR-141716/rimonabant (Sanofi) or SLV-319 (Solvay).

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79-022 and Curr. Ther. Res. 40:74 (1986); Ru 44570 (Hoechst) disclosed in Arzneimittelforschung 34:1254 (1985), cilazapril (Hoffman-LaRoche) disclosed in J. Cardiovasc. Pharmacol. 9:39 (1987); R 31-2201 (Hoffman-LaRoche) disclosed in FEBS Lett. 165: 201 (1984); lisinopril (Merck), indalapril (delapril) disclosed in U.S. Pat. No. 4,385,051; indolapril (Schering) disclosed in J. Cardiovasc. Pharmacol. 5:643, 655 (1983), spirapril (Schering) disclosed in Acta. Pharmacol. Toxicol. 59 (Supp. 5):173 (1986); perindopril (Servier) disclosed in Eur. J. clin. Pharmacol. 31:519 (1987); quinapril (Warner-Lambert) disclosed in U.S. Pat. No. 4,344,949 and CI925 (Warner-Lambert) ([3S-[2[R(★)R(★)][3R(★)[-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl)disclosed in Pharmacologist 26:243, 266 (1984), WY-44221 (Wyeth) disclosed in J. Med. Chem. 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, 5,552,397, 5,504,080, 5,612,359, 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred is omapatrilat, BMS 189,921 ([S-(R★,R★)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physician's Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®). Dosages employed will be as set out in the PDR.

In carrying our the method of the invention, a pharmaceutical composition will be employed containing the compounds of structure I, with or without another therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 50 and 2,000 mg per day, which can be administered in a single dose or in the form of individual doses from 1-4 times per day.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The following abbreviations are employed in the Examples:
Ph=phenyl
Bn=benzyl
t-Bu=tertiary butyl
Me=methyl
Et=ethyl
TMS=trimethylsilyl
$TMSN_3$=trimethylsilyl azide
$TMSCHN_2$=trimethylsilyl diazomethane
TBS=tert-butyldimethylsilyl
TBDPS=tert-butyldiphenylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
$Et_2O$=diethyl ether
hex=hexanes
EtOAc=ethyl acetate
DMF=dimethyl formamide
MeOH=methanol
EtOH=ethanol
i-PrOH=IPA=isopropanol
DMSO=dimethyl sulfoxide
DME=1,2 dimethoxyethane
DCE=1,2 dichloroethane
HMPA=hexamethyl phosphoric triamide
HOAc or AcOH=acetic acid
TFA=trifluoroacetic acid
PTSA=pTSOH=para-toluenesulfonic acid
i-$Pr_2$NEt=diisopropylethylamine
$Et_3N$=TEA=triethylamine
$Et_2NH$=diethylamine
NMM=N-methyl morpholine
DMAP=4-dimethylaminopyridine
$NaBH_4$=sodium borohydride
$NaBH(OAc)_3$=sodium triacetoxyborohydride
DIBALH=diisobutyl aluminum hydride
$LiAlH_4$=lithium aluminum hydride
n-BuLi=n-butyllithium
Pd/C=palladium on carbon
$PtO_2$=platinum oxide
KOH=potassium hydroxide
NaOH=sodium hydroxide
LiOH=lithium hydroxide
$K_2CO_3$=potassium carbonate
$NaHCO_3$=sodium bicarbonate
$H_2SO_4$=sulfuric acid
$KHSO_4$=potassium hydrogen phosphate
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.$H_2O$=1-hydroxybenzotriazole hydrate
HOAT=1-Hydroxy-7-azabenzotriazole BOP reagent=benzotriazol-1-yloxy-tris (dimethylamino) phosphonium hexafluorophosphate
NaN(TMS)$_2$=sodium hexamethyldisilazide or sodium bis(trimethylsilyl)amide
Ph$_3$P=triphenylphosphine
Pd(OAc)$_2$=Palladium acetate
(Ph$_3$P)$_4$Pd°=tetrakis triphenylphosphine palladium
DEAD=diethyl azodicarboxylate
DIAD=diisopropyl azodicarboxylate
Cbz-Cl=benzyl chloroformate
CAN=ceric ammonium nitrate
SiO$_2$=silica gel
SAX=Strong Anion Exchanger
SCX=Strong Cation Exchanger
Ar=argon
N$_2$=nitrogen
min=minute(s)
h or hr=hour(s)
L=liter
mL=milliliter
μL=microliter
μM=micromolar
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point
ee=enantiomeric excess The following examples represent preferred embodiments of the invention.

EXAMPLE 1

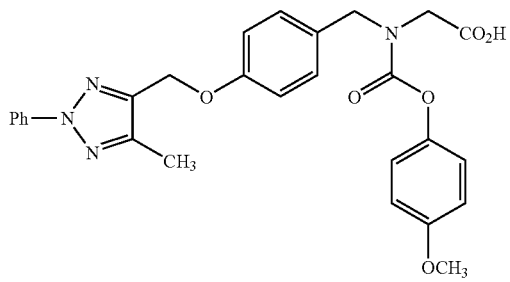

A.

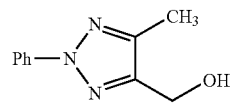

To a 0° C. solution of 4-methyl-2-phenyl-1,2,3 triazole-5-carboxylic acid (2.0 g; 9.8 mmol) in anhydrous THF (30 mL) was added borane in THF (29.5 mL of a 1 M solution; 29.5 mmol) dropwise. The reaction was allowed to warm to RT and the clear solution was stirred at RT for 20 h, then poured into an ice/H$_2$O mixture. The mixture was extracted with EtOAc (100 mL). The organic phase was washed with H$_2$O (50 mL), 1 N aqueous NaOH (50 mL), H$_2$O (2×50 mL), dried (Na$_2$SO$_4$), and concentrated in vacuo to give Part A compound (1.80 g; 100%) as white crystals.

B.

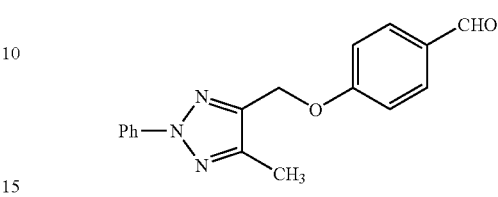

To a 0° C. solution of Part A compound (300 mg; 1.71 mmol), 4-hydroxybenzaldehyde (232 mg; 1.90 mmol) and Ph$_3$P (524 mg; 2.0 mmol) in anhydrous THF (15 mL) was added DEAD (400 μL; 2.2 mmol) dropwise and the resulting solution was allowed to warm to RT and stirred overnight at RT. Volatiles were removed in vacuo and the residue was chromatographed (SiO$_2$; stepwise gradient from 3:1 to 1:1 hexane:EtOAc) to provide Part B compound (440 mg; 88%) as a solid.

C.

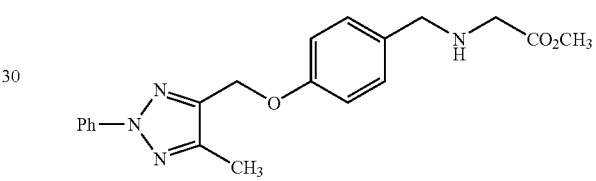

A mixture of Part B compound (100 mg; 0.34 mmol), glycine methyl ester hydrochloride (50 mg; 0.40 mmol) and Et$_3$N (50 mg; 0.50 mmol) in MeOH (2 mL) was stirred at RT for 5 h. The reaction mixture was cooled to 0° C. and NaBH$_4$ (18 mg; 0.50 mmol) was added portionwise (exothermic reaction). The reaction was allowed to warm to RT and stirred at RT for 30 min, then partitioned between EtOAc and H$_2$O. The organic phase was dried (Na$_2$SO$_4$) and concentrated in vacuo. The residue was chromatographed (SiO$_2$; stepwise gradient from 3:1 to 1:1 hexane:EtOAc) to give Part C compound (72 mg; 66%) as an oil.

D.

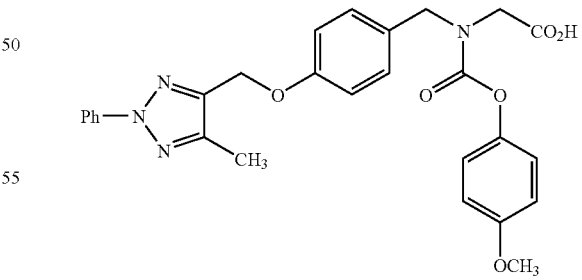

A solution of Part C compound (10 mg; 0.032 mmol), 4-methoxyphenyl chloroformate (6 mg; 0.032 mmol) and Et$_3$N (200 μL; 1.44 mmol) in CH$_2$Cl$_2$ (1 mL) was stirred at RT for 30 min. The reaction was complete by TLC at this point. Volatiles were removed in vacuo and the residue was dissolved in THF (2 mL) and aqueous LiOH (0.5 mL of a 1 M solution) was added. The reaction was stirred at RT overnight, after which volatiles were removed in vacuo. The residue was partitioned between EtOAc and excess aqueous 1M HCl. The organic phase was washed with H₂O, dried (Na₂SO₄) and concentrated in vacuo. The residue was purified by preparative HPLC (from 70% A:30% B to 0% A:100% B(A=90% H₂O/10% MeOH+0.1% TFA);(B=90% MeOH/10% H₂O+ 0.1% TFA) for 10 min at 25 ml/min; detection at 220 nm.; YMC ODS 20×100 mm column) to give the title compound (7 mg; 43%) as a solid.

[M+H]⁺=503.2

¹H NMR (CHCl₃): δ 2.44 (3H, s), 3.79 (3H, s), 4.04-4.56 (2H, 2s), 4.58-4.68 (2H, 2s), 5.19-5.21 (2H, 2s), 6.85-6.92 (2H, m), 7.00-7.75 (4H, m), 7.25-7.38 (3H, m), 7.44-7.48 (2 H, m), 8.00-8.02 (2H, m)

EXAMPLE 2

A solution of Example 1 Part C compound (10 mg; 0.032 mmol), benzoyl chloride (5 mg; 0.032 mmol) and Et₃N (200 μL; 1.44 mmol) in CH₂Cl₂ (1 mL) was stirred at RT for 30 min. The reaction was complete by TLC at this point. Volatiles were removed in vacuo and the residue was dissolved in THF (2 mL) and aqueous LiOH (0.5 mL of a 1 M solution) was added. The reaction was stirred at RT overnight, after which volatiles were removed in vacuo. The residue was partitioned between EtOAc and excess aqueous 1M HCl. The organic phase was washed with H₂O, dried (Na₂SO₄) and concentrated in vacuo. The residue was purified by preparative HPLC (from 70% A:30% B to 0% A:100% B(A=90% H₂O/10% MeOH+0.1% TFA);(B=90% MeOH/10% H₂O+ 0.1% TFA) for 10 min at 25 ml/min; detection at 220 nm.; YMC ODS 20×100 mm column) to give the title compound (9 mg; 60%) as a solid.

EXAMPLE 3

A.

To a 0° C. solution of Example 1 Part A compound (300 mg; 1.71 mmol), 3-hydroxybenzaldehyde (232 mg; 1.90 mmol) and Ph₃P (524 mg; 2.0 mmol) in THF (15 mL) was added DEAD (400 μL; 2.2 mmol) dropwise and the resulting solution was allowed to warm to RT and stirred overnight at RT. Volatiles were removed in vacuo and the residue was chromatographed (SiO₂; stepwise gradient from 3:1 to 1:1 hexane:EtOAc) to provide Part B compound (390 mg; 77%) as a solid.

B.

A mixture of Part A compound (100 mg; 0.34 mmol), glycine methyl ester hydrochloride (50 mg; 0.40 mmol) and Et₃N (50 mg; 0.50 mmol) in MeOH (2 mL) was stirred at RT for 5 h. The reaction mixture was cooled to 0° C. and NaBH₄ (18 mg; 0.50 mmol) was added portionwise (exothermic reaction). The reaction was allowed to warm to RT and stirred at RT for 30 min, then partitioned between EtOAc and H₂O. The organic phase was dried (Na₂SO₄) and concentrated in vacuo. The residue was chromatographed (SiO₂; stepwise gradient from 3:1 to 1:1 hexane:EtOAc) to give Part C compound (46 mg; 42%) as an oil.

C.

A solution of Part B compound (10 mg; 0.032 mmol), 4-methoxyphenyl chloroformate (6 mg; 0.032 mmol) and Et₃N (200 μL; 1.44 mmol) in CH₂Cl₂ (1 mL) was stirred at RT for 30 min. The reaction was complete by TLC at this point. Volatiles were removed in vacuo and the residue was dissolved in THF (2 mL) and aqueous LiOH (0.5 mL of a 1 M solution) was added. The reaction was stirred at RT overnight, after which volatiles were removed in vacuo. The residue was partitioned between EtOAc and excess aqueous 1M HCl. The organic phase was washed with H₂O, dried (Na₂SO₄) and concentrated in vacuo. The residue was purified by preparative HPLC (from 70% A:30% B to 0% A:100% B(A=90% H₂O/10% MeOH+0.1% TFA); (B=90% MeOH/10% H₂O+ 0.1% TFA) for 10 min at 25 ml/min; detection at 220 nm.; YMC ODS 20×100 mm column) to give the title compound (4 mg; 26%) as a solid.

[M+H]⁺=503.2

¹H NMR (CDCl₃): δ 2.44 (3H, s), 3.78 (3H, s), 4.07? (2H, ), 4.63-4.72 (2H, ), 5.20-5.22 (2H, ), 6.85-7.05 (7H, m), 7.26-7.32 (2H, m), 7.43-7.47 (2 H, m), 7.99-8.01 (2H, m)

EXAMPLE 4

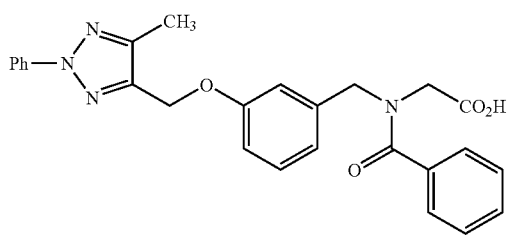

A solution of Example 3 Part B compound (10 mg; 0.032 mmol), benzoyl chloride (5 mg; 0.032 mmol) and Et₃N (200 μL; 1.44 mmol) in CH₂Cl₂ (1 mL) was stirred at RT for 30 min. The reaction was complete by TLC at this point. Volatiles were removed in vacuo and the residue was dissolved in THF (2 mL) and aqueous LiOH (0.5 mL of a 1 M solution) was added. The reaction was stirred at RT overnight, after which volatiles were removed in vacuo. The residue was partitioned between EtOAc and excess aqueous 1M HCl. The organic phase was washed with H₂O, dried (Na₂SO₄) and concentrated in vacuo. The residue was purified by preparative HPLC (from 70% A:30% B to 0% A:100% B(A=90% H₂O/10% MeOH+0.1% TFA); (B=90% MeOH/10% H₂O+ 0.1% TFA) for 10 min at 25 ml/min; detection at 220 nm.; YMC ODS 20×100 mm column) to give the title compound (16 mg; 90%) as a solid.

EXAMPLE 5

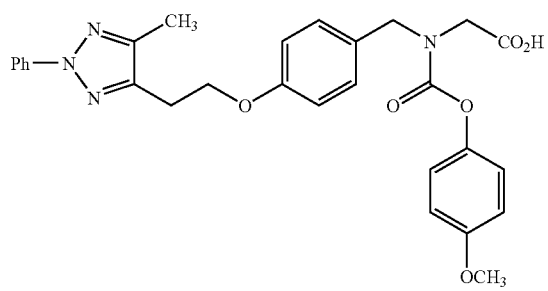

A.

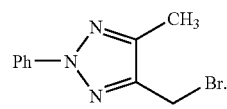

To a solution of Example 1 Part A compound (500 mg; 2.86 mmol) in CH₂Cl₂ (10 mL) was added PBr₃ (1.55 g; 2.86 mmol) and the solution was stirred at RT for 2 h. The reaction was partitioned between EtOAc (20 mL) and saturated aqueous NaHCO₃ (20 mL). The organic phase was washed successively with aqueous NaHCO₃ and water, dried (Na₂SO₄) and concentrated in vacuo to give Part A compound (600 mg; 83%) as a white solid.

B.

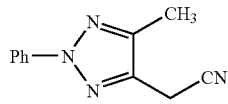

A mixture of Part A compound (600 mg; 2.38 mmol), KCN (300 mg; 2.50 mmol) and 18-crown-6 (200 mg; 0.76 mmol) in MeCN (10 mL) was refluxed under an atmosphere of N₂ for 2 h. HPLC indicated that all starting bromide had been consumed at this point. The reaction mixture was partitioned between EtOAc and H₂O. The organic phase was dried (Na₂SO₄) and concentrated in vacuo to give Part B compound (500 mg; 99%) as an oil, which was used in the next step without further purification.

C.

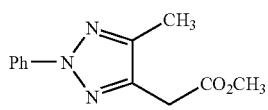

A solution of Part B compound (2.0 g; 10.0 mmol) in concentrated HCl (2.2 mL) and MeOH (35 mL) was heated in a sealed tube for 3 h at 85° C. Analytical HPLC showed that the mixture contained 80% product, 10% acid and 10% starting material. The reaction was cooled to RT and partitioned between EtOAc and saturated aqueous NaHCO₃. The organic phase was washed with water, dried (Na₂SO₄) and concentrated in vacuo. The residue was chromatographed (SiO₂; stepwise gradient from 10:1 to 5:1 hexane:EtOAc) to give Part C compound (1.30 g; 56%) as a white solid.

D.

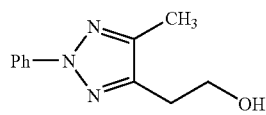

To a −78° C. solution of Part C compound (1.30 g; 5.62 mmol) in THF (5 mL) was added dropwise a solution of LiAlH₄ in THF (5.0 mL of a 1 M solution). The reaction mixture was allowed to warm to RT and stirred at RT for 2 h. At this point HPLC showed that all starting material had been consumed. The reaction was quenched by cautious dropwise addition of H₂O at 0° C. The resulting white solid was filtered off and the filtrate was concentrated in vacuo. The residue was chromatographed (SiO₂; stepwise gradient from 2:1 to 1:1 hexane:EtOAc) to give Part D compound (1.0 g; 88%) as a white solid.

E.

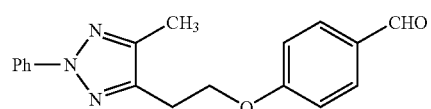

To a 0° C. solution of Part D compound (100 mg; 0.49 mmol), 4-hydroxybenzaldehyde (61 mg; 0.50 mmol) and Ph₃P (140 mg; 0.53 mmol) in anhydrous THF (2 mL) was added DEAD (95 μL; 0.60 mmol) dropwise and the resulting solution was allowed to warm to RT and stirred overnight at RT. Volatiles were removed in vacuo and the residue was chromatographed (SiO$_2$; stepwise gradient from 5:1 to 3:1 hexane:EtOAc) to provide Part E compound (163 mg; 99%) as a solid.

F.

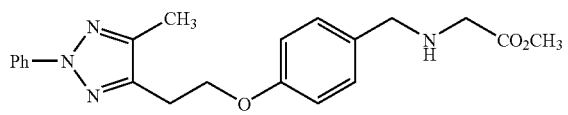

A mixture of Part E compound (100 mg; 0.33 mmol), glycine methyl ester hydrochloride (50 mg; 0.40 mmol) and Et$_3$N (70 μL; 0.50 mmol) in MeOH (2 mL) was stirred at RT for 5 h. The reaction mixture was cooled to 0° C. and NaBH$_4$ (15 mg; 0.40 mmol) was added portionwise (exothermic reaction). The reaction was allowed to warm to RT and stirred at RT for 30 min, then partitioned between EtOAc and H$_2$O. The organic phase was dried (Na$_2$SO$_4$) and concentrated in vacuo. The residue was chromatographed (SiO$_2$; stepwise gradient from 3:1 to 1:1 hexane:EtOAc) to give Part F compound (100 mg; 80%) as an oil.

G.

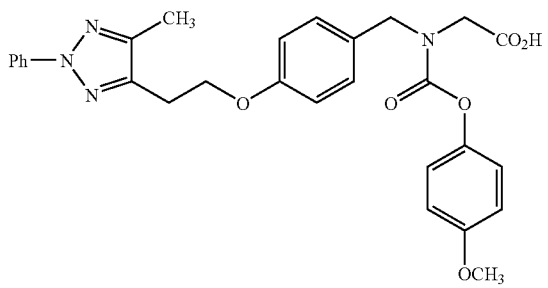

A solution of Part F compound (100 mg; 0.26 mmol), 4-methoxyphenyl chloroformate (56 mg; 0.30 mmol) and Et$_3$N (42 μL; 0.30 mmol) in CH$_2$Cl$_2$ (1 mL) was stirred at RT for 30 min. The reaction was complete by TLC at this point. Volatiles were removed in vacuo and the residue was dissolved in THF (3 mL) and aqueous LiOH (1.0 mL of a 1 M solution) was added. The reaction was stirred at RT overnight, after which volatiles were removed in vacuo. The residue was partitioned between EtOAc and excess aqueous 1M HCl. The organic phase was washed with H$_2$O, dried (Na$_2$SO$_4$) and concentrated in vacuo. The residue was purified by preparative HPLC (from 70% A:30% B to 0% A:100% B(A=90% H$_2$O/10% MeOH+0.1% TFA); (B=90% MeOH/10% H$_2$O+ 0.1% TFA) for 30 min at 25 ml/min; detection at 220 nm.; YMC ODS 30×250 mm column) to give the title compound (54 mg; 40%) as a solid.

[M+H]$^+$=517.3

$^1$H NMR (CDCl$_3$): δ 2.40 (3H, s), 3.17-3.20 (2H, m), 3.78 (3H, s), 4.02-4.03 (2H, m), 4.26-4.30 (2H, m), 4.55-4.60 (2H, ss), 6.81-6.92 (5H, m), 6.99-7.10 (2H, m), 7.20-7.31 (2H, m), 7.41-7.46 (2 H, m), 7.96-7.98 (2H, m).

EXAMPLE 6

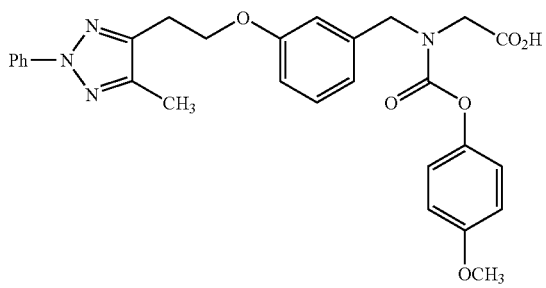

-continued

A.

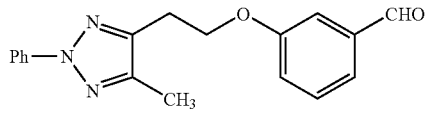

To a 0° C. solution of Example 5 Part D compound (100 mg; 0.49 mmol), 3-hydroxybenzaldehyde (61 mg; 0.50 mmol) and Ph$_3$P (140 mg; 0.53 mmol) in anhydrous THF (2 mL) was added DEAD (95 μL; 0.60 mmol) dropwise and the resulting solution was allowed to warm to RT and stirred overnight at RT. Volatiles were removed in vacuo and the residue was chromatographed (SiO$_2$; stepwise gradient from 5:1 to 3:1 hexane:EtOAc) to provide Part A compound (45 mg; 30%) as a solid.

B.

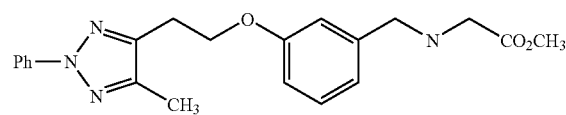

A mixture of Part A compound (50 mg; 0.33 mmol), glycine methyl ester hydrochloride (50 mg; 0.40 mmol) and Et$_3$N (70 μL; 0.50 mmol) in MeOH (2 mL) was stirred at RT for 5 h. The reaction mixture was cooled to 0° C. and NaBH$_4$ (15 mg; 0.40 mmol) was added portionwise (exothermic reaction). The reaction was allowed to warm to RT and stirred at RT for 30 min, then partitioned between EtOAc and H$_2$O. The organic phase was dried (Na$_2$SO$_4$) and concentrated in vacuo. The residue was chromatographed (SiO$_2$; stepwise gradient from 3:1 to 1:1 hexane:EtOAc) to give Part F compound (100 mg; 81%) as an oil.

C.

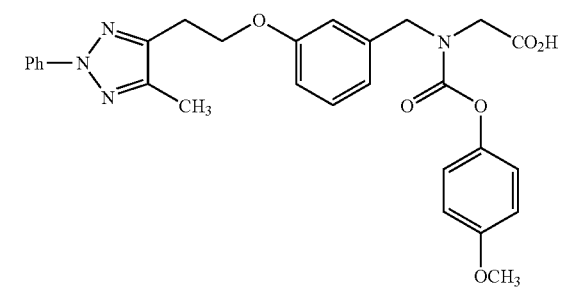

A solution of Part B compound (100 mg; 0.26 mmol), 4-methoxyphenyl chloroformate (56 mg; 0.30 mmol) and Et$_3$N (42 μL; 0.30 mmol) in CH$_2$Cl$_2$ (1 mL) was stirred at RT for 30 min. The reaction was complete by TLC at this point. Volatiles were removed in vacuo and the residue was dissolved in THF (3 mL) and aqueous LiOH (1.0 mL of a 1 M solution) was added. The reaction was stirred at RT overnight, after which volatiles were removed in vacuo. The residue was partitioned between EtOAc and excess aqueous 1M HCl. The organic phase was washed with H$_2$O, dried (Na$_2$SO$_4$) and concentrated in vacuo. The residue was purified by preparative HPLC (from 70% A:30% B to 0% A:100% B (A=90% H$_2$O/10% MeOH+0.1% TFA); (B=90% MeOH/10% H$_2$O+ 0.1% TFA) for 30 min at 25 ml/min; detection at 220 nm.; YMC ODS 30×250 mm column) to give the title compound (26 mg; 19%) as a solid.

[M+H]$^+$=517.3

$^1$H NMR (CDCl$_3$): δ 2.41 (3H, s), 3.18-3.20 (2H, m), 3.77 (3H, s), 4.06 (2H,d, J=4.4Hz), 4.28-4.32 (2H, m), 4.60-4.70

(2H, ss), 6.80-6.91 (5H, m), 7.01-7.05 (2H, m), 7.25-7.31 (2H, m), 7.41-7.45 (2 H, m), 7.95-7.97 (2H, m)

EXAMPLE 7

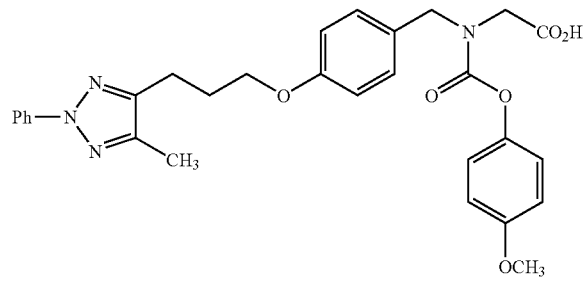

A.

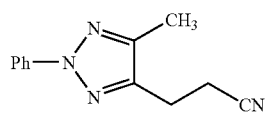

A solution of Example 5 Part D compound (900 mg; 4.43 mmol) in PBr$_3$ (5.0 mL of a 1 M solution in CH$_2$Cl$_2$) was stirred at RT for 30 min. At this point HPLC showed that all starting material had been consumed. Volatiles were removed in vacuo and the residue was partitioned between EtOAc and H$_2$O. The organic phase was washed with saturated aqueous NaHCO$_3$ and concentrated in vacuo. The residue was chromatographed (SiO$_2$; hexane:EtOAc) to give the crude bromide (427 mg; 36%). A mixture of this material, KCN (290 mg; 4.43 mmol) and 18-crown-6 (1.2 g; 4.54 mmol) in MeCN (5 mL) was refluxed under an atmosphere of N$_2$ for 2 h. The reaction mixture was partitioned between EtOAc and H$_2$O. The organic phase was dried (Na$_2$SO$_4$) and concentrated in vacuo to give Part A compound (300 mg; 88%) as an oil, which was used in the next step without further purification.

B.

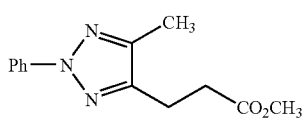

A solution of Part A compound (300 mg; 1.41 mmol) in concentrated HCl (2 mL) and MeOH (5 mL) was heated at 85° C. in a sealed tube for 3 h. The reaction was cooled to RT, then partitioned between EtOAc (20 mL) and excess aqueous 1 M NaOH and aqueous 1 M NaHCO$_3$. The organic extract was washed with H$_2$O, dried (Na$_2$SO$_4$) and concentrated in vacuo. The residue was treated with trimethylsilyldiazomethane (1 mL of a 2.0 M solution in hexanes; 2.0 mmol) and MeOH (3 mL) for 1 h at RT, after which volatiles were removed in vacuo. The residue was chromatographed (SiO$_2$; 4:1 hexane:EtOAc) to give Part B compound (260 mg; 99%) as a colorless oil.

C.

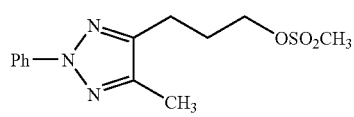

To a 0° C. solution of Part B compound (260 mg; 1.06 mmol) in THF (10 mL) was added dropwise a solution of LiAlH$_4$ in THF (1.0 mL of a 1 M solution; 1.0 mmol). The reaction mixture was allowed to warm to RT and stirred at RT for 1 h. At this point TLC showed that reaction was complete.

The reaction was quenched at 0° C. by dropwise addition of H$_2$O (0.5 mL). The solids were filtered off and the filtrate was concentrated in vacuo to give the crude alcohol as an oil. To a 0° C. solution of this material and Et$_3$N (101 mg; 1.0 mmol) in CH$_2$Cl$_2$ (2 mL) was added methanesulfonyl chloride (121 mg; 1.0 mmol) dropwise. The reaction mixture was allowed to warm to RT and stirred at RT for 2 h, at which point TLC indicated that all starting material had been consumed. The mixture was partitioned between EtOAc and H$_2$O, and the organic phase was dried (Na$_2$SO$_4$) and concentrated in vacuo to give Part C compound (325 mg; 99%) as an oil. This crude material was used in the next step without further purification.

D.

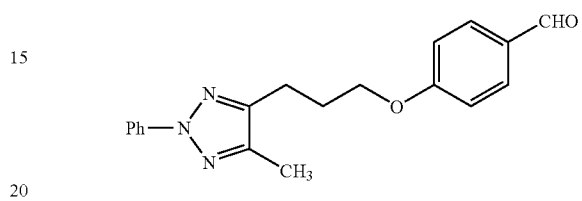

A mixture of Part C compound (150 mg; 0.51 mmol), 4-hydroxybenzaldehyde (62 mg; 0.51 mmol) and K$_2$CO$_3$ (210 mg; 1.53 mmol) in DMF (1 mL) was heated at 100° C. in an oil bath for 2 h. At this point HPLC indicated that all starting material had been consumed. The reaction was cooled to RT and poured into ice-water (20 mL) and stirred for ~10 min. The solid precipitate was collected, dried under vacuum, and recrystallized from toluene/hexanes to provide Part D compound (162 mg; 90%) as a solid.

E.

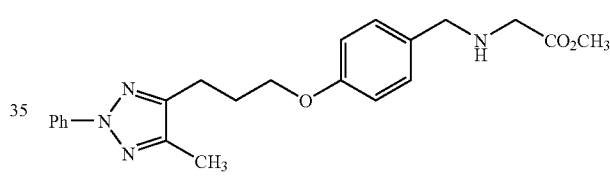

A mixture of Part D compound (174 mg; 0.543 mmol), glycine methyl ester hydrochloride (68 mg; 0.54 mmol) and Et$_3$N (72 µL; 0.54 mmol) in MeOH (4 mL) was stirred at RT for 5 h. The reaction mixture was cooled to 0° C. and NaBH$_4$ (20 mg; 0.54 mmol) was added portionwise (exothermic reaction). The reaction was allowed to warm to RT and stirred at RT for 30 min, then partitioned between EtOAc and H$_2$O. The organic phase was dried (Na$_2$SO$_4$) and concentrated in vacuo. The residue was chromatographed (SiO$_2$; stepwise gradient from 3:1 to 1:1 hexane:EtOAc) to give Part E compound (176 mg; 82%) as an oil.

F.

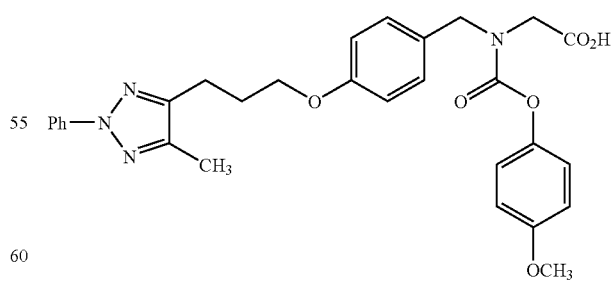

A solution of Part E compound (25 mg; 0.063 mmol), 4-methoxyphenyl chloroformate (12 mg; 0.065 mmol) and Et$_3$N (28 µL; 0.20 mmol) in CH$_2$Cl$_2$ (1 mL) was stirred at RT for 30 min. The reaction was complete by TLC at this point. Volatiles were removed in vacuo and the residue was dissolved in THF (1 mL) and aqueous LiOH (100 μL of a 1 M solution) was added. The reaction was stirred at RT overnight, after which volatiles were removed in vacuo. The residue was partitioned between EtOAc and excess aqueous 1M HCl. The organic phase was washed with $H_2O$, dried ($Na_2SO_4$) and concentrated in vacuo. The residue was purified by preparative HPLC (from 70% A:30% B to 0% A:100% B (A=90% $H_2O$/10% MeOH+0.1% TFA); (B=90% MeOH/10% $H_2O$+ 0.1% TFA) for 30 min at 25 ml/min; detection at 220 nm.; YMC ODS 30×250 mm column) to give the title compound (20 mg; 60%) as a solid.

[M+H]$^+$=531.3
$^1$H NMR (CDCl$_3$): δ 2.21 (2H, m), 2.33 (3H, s), 2.88 (2H, m), 3.78 (3H, s), 4.05 (4H, m), 4.57-4.67 (2H, m), 6.85-6.91 (5H, m), 7.02-7.08 (2H, m), 7.22-7.30 (2H, m), 7.39-7.48 (2 H, m), 7.95-7.97 (2H, d, J=7.9 Hz)

EXAMPLE 8

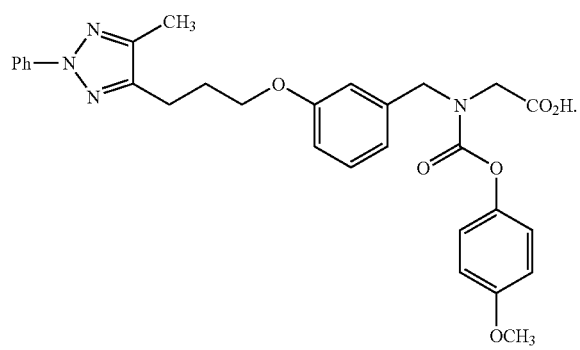

A.

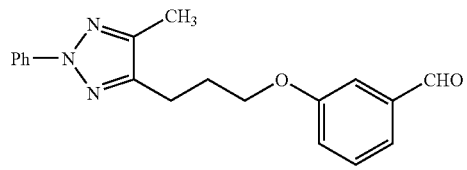

A mixture of Example 7 Part C compound (150 mg; 0.51 mmol), 3-hydroxybenzaldehyde (62 mg; 0.51 mmol) and $K_2CO_3$ (210 mg; 1.53 mmol) in DMF (1 mL) was heated at 100° C. in an oil bath for 2 h. At this point HPLC indicated that all starting material had been consumed. The reaction was cooled to RT and poured into ice-water (20 mL) and stirred for ~10 min. The solid precipitate was collected, washed with cold water (2×5 mL), dried under vacuum, and recrystallized from toluene/hexanes to provide to provide Part A compound (174 mg; 90%) as a solid.

B.

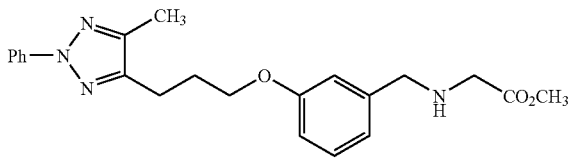

A mixture of Part A compound (174 mg; 0.543 mmol), glycine methyl ester hydrochloride (68 mg; 0.54 mmol) and Et$_3$N (72 μL; 0.54 mmol) in MeOH (4 mL) was stirred at RT for 5 h. The reaction mixture was cooled to 0° C. and NaBH$_4$ (20 mg; 0.54 mmol) was added portionwise (exothermic reaction). The reaction was allowed to warm to RT and stirred at RT for 30 min, then partitioned between EtOAc and $H_2O$. The organic phase was dried ($Na_2SO_4$) and concentrated in vacuo. The residue was chromatographed (SiO$_2$; stepwise gradient from 3:1 to 1:1 hexane:EtOAc) to give Part B compound (180 mg; 84%) as an oil.

C.

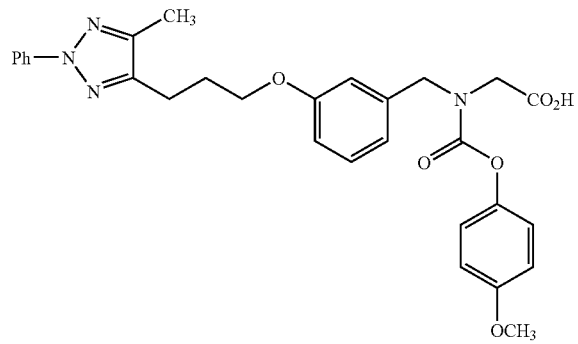

A solution of Part B compound (25 mg; 0.063 mmol), 4-methoxyphenyl chloroformate (12 mg; 0.065 mmol) and Et$_3$N (28 μL; 0.20 mmol) in CH$_2$Cl$_2$ (1 mL) was stirred at RT for 30 min. The reaction was complete by TLC at this point. Volatiles were removed in vacuo and the residue was dissolved in THF (1 mL) and aqueous LiOH (100 μL of a 1 M solution) was added. The reaction was stirred at RT overnight, after which volatiles were removed in vacuo. The residue was partitioned between EtOAc and excess aqueous 1M HCl. The organic phase was washed with $H_2O$, dried ($Na_2SO_4$) and concentrated in vacuo. The residue was purified by preparative HPLC (from 70% A:30% B to 0% A:100% B (A=90% $H_2O$/10% MeOH+0.1% TFA); (B=90% MeOH/10% $H_2O$+ 0.1% TFA) for 30 min at 25 ml/min; detection at 220 nm.; YMC ODS 30×250 mm column) to give the title compound (15 mg; 45%) as a solid.

[M+H]$^+$=531.3
$^1$H NMR (CDCl$_3$): δ 2.21 (2H, m), 2.33 (3H, s), 2.88 (2H, t, J=7.5 Hz), 3.78 (3H, s), 4.03 (4H, m), 4.57-4.67 (2H, m), 6.84-6.89 (5H, m), 7.01-7.05 (2H, m), 7.29 (2H, m), 7.40-7.45 (2 H, m), 7.94-7.96 (2H, d, J=7.9 Hz)

EXAMPLE 9

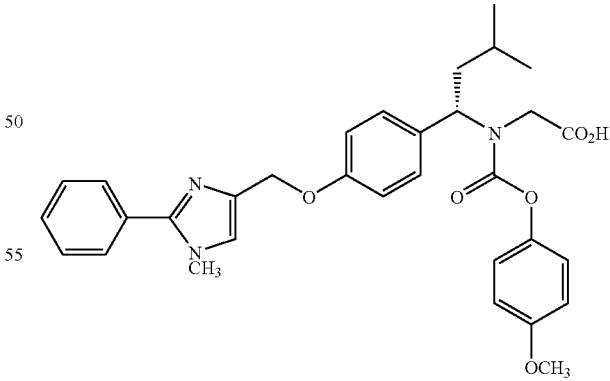

A and B

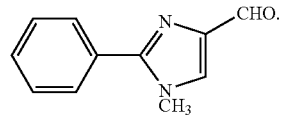

To a solution of 4-formyl-2-phenylimidazole (100 mg, 0.58 mmol) in CH$_2$Cl$_2$ (2 mL) was added aqueous KOH (2 mL of a 30% solution), followed by dimethyl sulfate (66 µL, 0.70 mmol), and tetrabutylammonium bromide (10 mg; 0.03 mmol). The reaction mixture was stirred overnight at RT and then was partitioned between EtOAc and water; the organic phase was washed with brine and then concentrated in vacuo. The residue was chromatographed (SiO$_2$; continuous gradient from 1:1 hexane:EtOAc to 100% EtOAc) to give 1-methyl-2-phenyl-imidazole-5-carboxaldehyde as a solid (45 mg; 42%; $1^{st}$ product to elute; Part A compound) and the isomeric product Part B compound

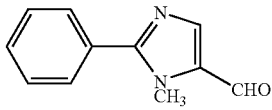

(35 mg; 32%; $2^{nd}$ product to elute) as a solid.

C.

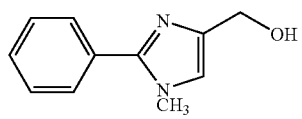

To a solution of Part A compound (50 mg, 0.27 mmol) in MeOH (5 mL) was added NaBH$_4$ (30 mg; 0.79 mmol). The mixture was stirred at RT for 1 h, after which the reaction was quenched with excess saturated aqueous NH$_4$Cl (5 mL). Volatiles were removed in vacuo, and the residue was partitioned between saturated aqueous NaHCO$_3$ and EtOAc. The organic phase was washed with brine, dried (Na$_2$SO$_4$) and concentrated in vacuo to give Part C compound as a white solid (37 mg, 75%).

D.

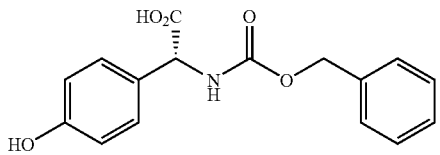

To a solution of (D)-4-hydroxyphenylglycine (20.0 g; 120 mmol) in MeOH (400 mL) was added dropwise chlorotrimethylsilane (30.4 mL; 240 mmol). The reaction was stirred at RT for 74 h, then concentrated in vacuo. To a solution of the residue in dioxane/H$_2$O (400 mL of a 1:1 solution) were successively added NaHCO$_3$ (30.2 g; 359 mmol) and benzyl chloroformate (18.8 mL; 132 mmol). The reaction was stirred at RT for 4 h, then concentrated in vacuo. The residue was partitioned between H$_2$O and EtOAc; the organic phase was washed with brine, dried (MgSO$_4$) and concentrated in vacuo to give crude Part D compound (39.5 g). This material was recrystallized from hexane:EtOAc to give pure Part D compound (37.5 g; 99%) as white crystals.

E.

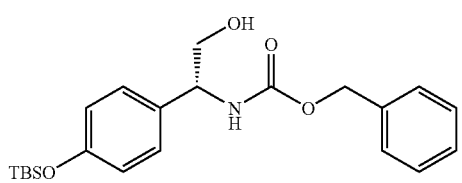

To a solution of Part D compound (20 g; 63.5 mmol) in DMF (127 mL) were successively added tertbutyldimethyl-silyl chloride (14.4 g; 95 mmol) and imidazole (6.50 g; 95 mmol). The reaction was s tirred at RT overnight, then partitioned between EtOAc and H$_2$O. The organic phase was washed with H$_2$O and brine, dried (MgSO$_4$) and concentrated in vacuo. The residue was dissolved in THF (318 mL) and cooled to 0° C.; a solution of lithium borohydride (76.2 mL of a 2 M solution in THF; 152 mmol) was added dropwise. After addition was complete, the reaction mixture was allowed to warm to RT and stirred at RT overnight, then quenched by slow addition of excess MeOH. Volatiles were removed in vacuo to provide crude Part E compound.

F.

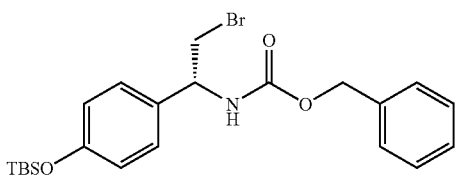

To a 0° C. solution of crude Part E compound (theoretically 63.5 mmol) in CH$_2$Cl$_2$ (212 mL) were successively added Et$_3$N (8.9 mL; 63.5 mmol) and methanesulfonyl chloride (4.90 mL; 63.5 mmol). The reaction was stirred at 0° C. for 1 h, then was partitioned between CH$_2$Cl$_2$ and aqueous 1 N HCl. The organic phase was washed with brine, dried (MgSO4), then concentrated in vacuo to give the crude mesylate. This material was dissolved in acetone (212 mL) and lithium bromide (9.0 g; 104 mmol) was added. The reaction mixture was stirred at 50° C. overnight, then cooled to RT and concentrated in vacuo. The residue was chromatographed (SiO$_2$; continuous gradient from 100% hexane to 100% EtOAc) to give Part F compound (1.15 g; 4% over 4 steps) as well as the deprotected phenol

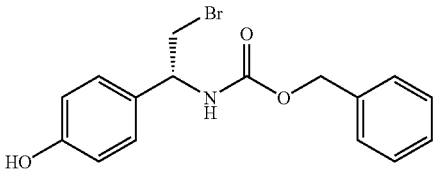

1.44 g; 7% over 4 steps)

G.

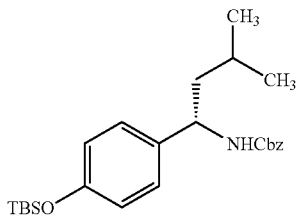

To a −78° C. slurry of CuCN (650 mg; 7.26 mmol) in freshly distilled dry THF (24.2 mL) under argon was added dropwise isopropyllithium (20.4 mL of a 0.7 M solution in hexane; 14.5 mmol). The mixture was allowed to warm slowly to 0° C., at which point a clear solution of the cyanocuprate reagent was obtained. The solution was cooled to −50° C. (cyclohexanone-dry ice bath) and Part F compound (1.12 g; 2.42 mmol) in dry THF (6.9 mL) was added dropwise. The resulting mixture was allowed to warm from −50° C. to 10° C. over 4 h, then quenched by slow addition of an aqueous solution of 9:1 saturated aqueous NH4Cl:concentrated NH$_4$OH. The mixture was vigorously stirred until most of the solids had been dissolved, then partitioned between H$_2$O and EtOAc. The organic phase was washed with saturated aqueous NH₄Cl and brine, dried (MgSO₄) and concentrated in vacuo. The residue was chromatographed (continuous gradient from 100% hexane to 100% EtOAc) to give Part G compound (317 mg; 31%) as a clear colorless oil.

H.

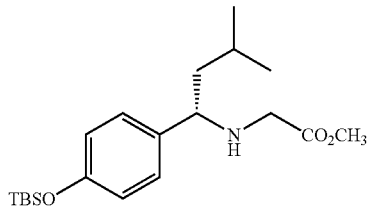

A mixture of Part G compound (317 mg; 0.742 mmol) and 10% Pd/C (159 mg) in MeOH (3.7 mL) was stirred under an atmosphere of H₂ (balloon) at RT for 3 h. The catalyst was filtered off (Celite®) and the filtrate was concentrated in vacuo. A solution of the resulting crude free amine, Et₃N (114 µL; 0.81 mmol) and methyl bromoacetate (77 µL; 0.81 mmol) in THF (9.3 mL) was stirred at RT overnight. The reaction mixture was partitioned between EtOAc and H₂O; the organic phase was washed with brine, dried (MgSO₄) and concentrated in vacuo to provide crude Part H compound.

I.

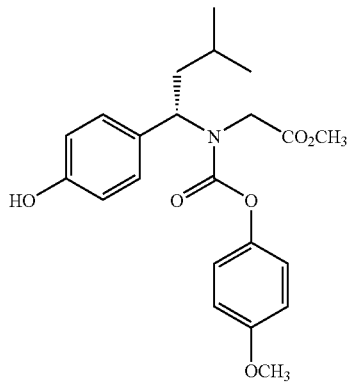

To a solution of the crude Part H compound from above (0.742 mmol theoretically) and NaHCO₃ (125 mg; 1.48 mmol) in dioxane:H₂O (7.4 mL of a 1:1 solution) was added 4-methoxyphenyl chloroformate (220 µL; 1.48 mmol) dropwise. The reaction was stirred at RT for 2 h, then partitioned between EtOAc and H₂O. The organic phase was washed with aqueous 1N HCl and brine, dried (MgSO₄) and concentrated in vacuo. The crude TBS-protected phenol product was dissolved in THF (3 mL) and tetrabutylammonium fluoride (1 mL of a 1M solution in THF) was added. The reaction was stirred at RT for 1 h, after which it was partitioned between EtOAc and H₂O. The organic phase was washed with brine, dried (MgSO4) and concentrated in vacuo. The residue was purified by preparative HPLC (continuous gradient from 70:30 A:B to 100% B; A=90:10:0.1 H₂O:MeOH:TFA; B=90:10:0.1 MeOH:H₂O:TFA; 12 min run @ 20 mL/min; detection at 220 nm; YMC ODS 20×100 mm column) to provide Part I compound (117 mg; 39% over 4 steps) as an oil.

J.

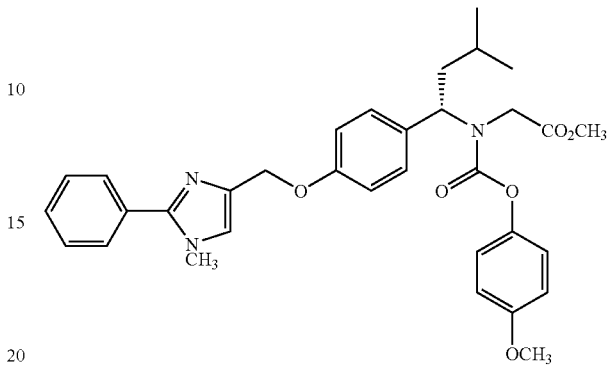

To a 65° C. solution of Part I compound (10 mg; 0.025 mmol), Part B compound (10 mg; 0.05 mmol) and Ph₃P (16 mg; 0.063 mmol) in toluene (2 mL) was added dropwise diethyl azodicarboxylate (10 µL; 0.063 mmol). The reaction was stirred at 65° C. for 2 days, then was partitioned between EtOAc/Hex (1:1) and water (15 mL each). The organic phase was dried (MgSO₄) and concentrated in vacuo. The residue was purified by preparative HPLC (continuous gradient from 50:50 A:B to 100% B; A=90:10:0.1 H₂O:MeOH:TFA; B=90:10:0.1 MeOH:H₂O:TFA) to give Part J compound (2.5 mg; 18%) as a solid.

K.

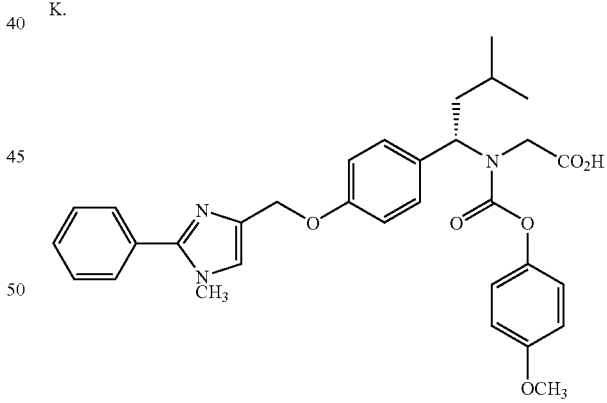

A solution of Part J compound (2.5 mg; 0.0043 mmol) and LiOH.H₂O (1 mg; 0.024 mmol) in H₂O/THF was stirred at RT overnight, after which volatiles were removed in vacuo. The residue was partitioned between EtOAc and excess aqueous 1M HCl. The organic phase was washed with H₂O, dried (Na₂SO₄) and concentrated in vacuo. The residue was purified by preparative HPLC (using the same conditions as for the purification of Part J compound) to give the title compound (0.5 mg; 21%) as a solid $[M+H]^+$=558.2.

EXAMPLE 10

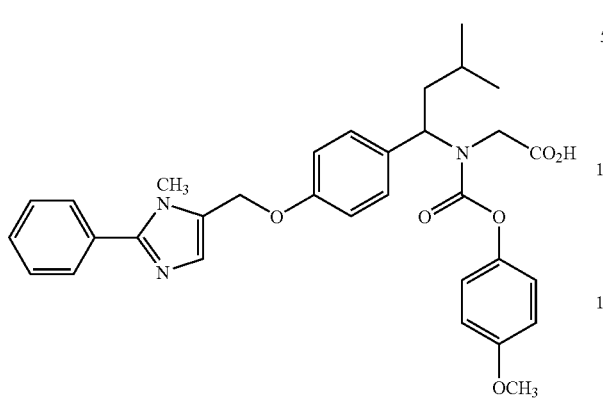

A.

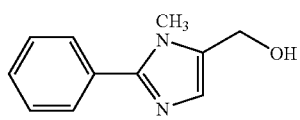

To a solution of Example 9 Part B compound (136 mg, 0.73 mmol) in MeOH (10 mL) was added NaBH$_4$ (60 mg; 1.58 mmol). The mixture was stirred at RT for 1 h, after which the reaction was quenched with excess saturated aqueous NH$_4$Cl (10 mL). Volatiles were removed in vacuo, and the residue was partitioned between saturated aqueous NaHCO$_3$ and EtOAc. The organic phase was washed with brine, dried (Na$_2$SO$_4$) and concentrated in vacuo to give Part A compound as an oil (110 mg, 80%).

B.

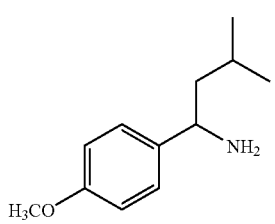

To a RT solution of 4-methoxybenzonitrile (13 g; 98 mmol) in THF (200 mL) under argon were successively added CuCl (250 mg; 2.5 mmol) and isobutyl magnesium bromide (50 mL of a 2 M solution in Et$_2$O; 100 mmol). The reaction mixture was heated at 60° C. for 2 h, then was cooled to RT. Lithium aluminum hydride (3.50 g; 18.4 mmol) was added portionwise, after which the reaction mixture was heated at 60° C. for a further 2 h, then was cooled to RT and stirred overnight at RT. The reaction was quenched by slow dropwise addition of EtOAc (50 mL), then was stirred at RT for 2 h, followed by addition of THF (100 mL) and saturated aqueous NaHCO$_3$ (50 mL). The mixture was stirred at RT for 2 h, then was filtered. The residual solids were washed with EtOAc and the combined filtrates were concentrated in vacuo. The residue was partitioned between EtOAc (500 mL) and aqueous 1 N NaOH (200 mL). The organic phase was dried (Na$_2$SO$_4$) and concentrated in vacuo to give crude Part B compound (19 g; 100%) as a yellow oil.

C.

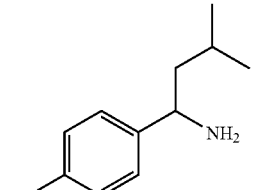

To a 0° C. solution of crude Part B compound (18 g; 93 mmol) in CH$_2$Cl$_2$ (200 mL) under argon was added dropwise BBr$_3$ (30 mL; 320 mmol). The reaction was allowed to slowly warm to RT and was stirred at RT for 2 h, then was cooled to −78° C. CH$_2$Cl$_2$ (200 mL) was added, followed by slow dropwise addition of MeOH (30 mL). After addition was complete, the mixture was allowed to warm slowly to RT, then cooled to 0° C. Additional MeOH (100 mL) was added cautiously, followed by 15% aqueous HCl (150 mL). Organic solvents were removed in vacuo to give ~150 mL of aqueous solution, which was cooled to 0° C. and cautiously basified with excess concentrated ammonium hydroxide solution (until pH ~10). The resultant white precipitate was washed successively with H$_2$O, THF and EtOAc and dried to give crude Part C compound (9.0 g; 54%) as a white solid.

D.

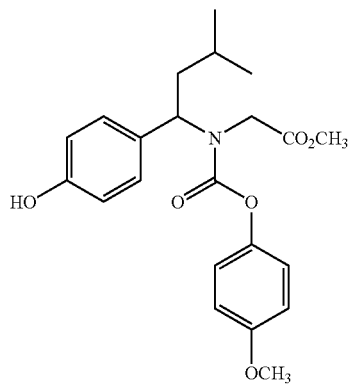

To a solution of Part C compound (800 mg; 4.47 mmol) in THF/MeOH (20 mL of a 1:1 solution) were successively added Et$_3$N (1 mL; 6.4 mmol) and methyl bromoacetate (800 μL; 8.5 mmol). The reaction mixture was stirred at RT for 2 h, at which point the reaction was ~80% complete by analytical HPLC. Saturated aqueous NaHCO$_3$ (2 mL) was then added, followed by dropwise addition of 4-methoxy-phenyl chloroformate (1.10 mL; 7.4 mmol). The reaction was stirred at RT for 30 min, after which volatiles were removed in vacuo. The residue was partitioned between saturated aqueous NaHCO$_3$ and Et$_2$O (100 mL). The organic phase was washed with aqueous 1 N HCl and brine, dried (Na$_2$SO$_4$) and concentrated in vacuo. The residue was chromatographed (SiO$_2$; continuous gradient from 100% hexane to 100% EtOAc) to give Part D compound (400 mg; 27%) as a white solid.

ent from 99:1 to 95:5 CH$_2$Cl$_2$:MeOH) to give Part A compound (650 mg; 51%) as a yellow solid.

E.

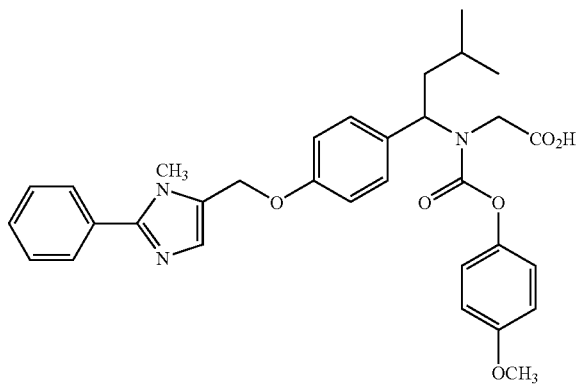

B.

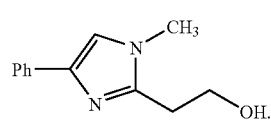

To a −78° C. solution of Part A compound (650 mg; 4.11 mmol) in anhydrous THF (8.5 mL) was added dropwise n-BuLi (1.9 mL of a 2.5 M solution in hexanes; 4.75 mmol). The reaction was stirred at −78° C. for 15 min, after which ethylene oxide (3 mL; 580 mmol; liquefied by cooling in dry-ice/acetone) was added. The reaction mixture was gradually allowed to warm to RT and stirred at RT overnight, then partitioned between water and Et$_2$O (60 mL each). The organic phase was washed with brine (50 mL), dried (MgSO$_4$) and concentrated in vacuo. The residue was chromatographed (SiO$_2$; continuous gradient from 100% CH$_2$Cl$_2$ to 92:8 CH$_2$Cl$_2$:MeOH) to provide Part B compound (200 mg; 24%) as a white solid.

To a 65° C. solution of Part D compound (53 mg; 0.13 mmol), Part A compound (50 mg; 0.27 mmol) and Ph$_3$P (84 mg; 0.33 mmol) in toluene (6 mL) was added dropwise diethyl azodicarboxylate (51 μL; 0.33 mmol). The reaction was stirred at 65° C. for 2 days, then was partitioned between EtOAc/Hex (1:1) and water (25 mL each). The organic phase was dried (MgSO$_4$) and concentrated in vacuo. The residue was purified by preparative HPLC (as for the purification of Example 9 Part J compound) to give the ester intermediate. This material was subjected to lithium hydroxide-mediated hydrolysis (as for Example 9 compound) and the crude product was purified by preparative HPLC (as for Example 9 compound Part J compound) to provide the title compound (30 mg; 36%) as an oil.
[M+H]$^+$=558.2

C.

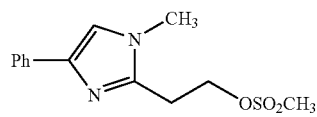

To a 0° C. solution of Part B compound (30 mg; 0.15 mmol) and Et$_3$N (25 μL; 0.18 mmol) in CH$_2$Cl$_2$ (2 mL) was added dropwise methanesulfonyl chloride (14 μL; 0.18 mmol). The reaction was stirred at 0° C. for 30 min, after which TLC (hexane:EtOAc 1:1) indicated that the reaction was complete. Volatiles were removed in vacuo to give Part C compound (38 mg; 91%) which was used in the next step without further purification.

D.

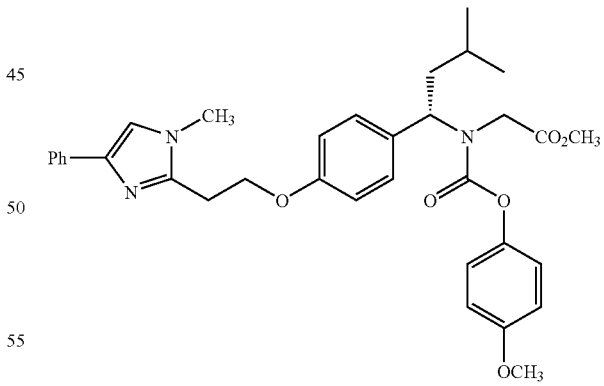

EXAMPLE 11

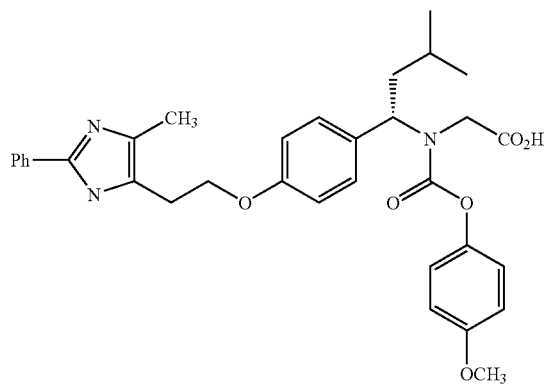

A.

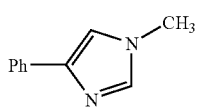

A mixture of 4-phenyl imidazole (1.15 g; 8 mmol) and acetic anhydride (1.85 mL, 20 mmol) in toluene (6 mL) was heated at 80° C. for 1.5 h. At this point a solution of iodomethane (1.25 mL; 20 mmol) in toluene (6 mL) was added and the reaction mixture was heated in a sealed tube at 140° C. overnight. Volatiles were removed in vacuo & the residue was taken up in CH$_2$Cl$_2$ (40 mL). The insoluble material was filtered off and the filtrate was concentrated in vacuo. The residue was chromatographed (SiO2; continuous gradi- A mixture of crude Part C compound (38 mg; 0.14 mmol), Example 9 Part H compound (10 mg; 0.025 mmol) and K$_2$CO$_3$ (7 mg; 0.05 mmol) in MeCN (2 mL) was heated at reflux for 19 h. Volatiles were removed in vacuo and the residue was purified by preparative HPLC (from 50% A:50% B to 100% B (A=90:10:0.1 H$_2$O:MeOH:TFA; B=90:10:0.1 MeOH:H$_2$O:TFA) for 12 min at 20 mL/min; detection at 220 nm; YMC ODS 20×100 mm column) to give Part D compound (9 mg; 61%) as a syrup.

E.

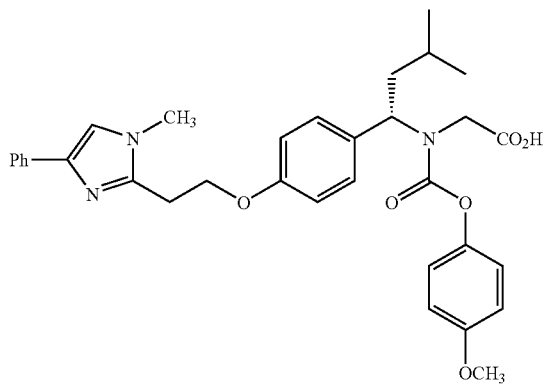

A solution of Part D compound (9 mg; 0.015 mmol) and LiOH.H₂O (7 mg; 0.15 mmol) in THF and H₂O (1 mL each) was stirred at RT for 44 h. The solution was acidified to pH 5 with aqueous 1 N HCl, then extracted with EtOAc (3×). The combined organic extracts were concentrated in vacuo and the residue was purified by preparative HPLC (as for Part D compound) to give, after lyophilization from dioxane, the title compound (6 mg; 68%) as a white solid.

$[M+H]^+=572.3$

EXAMPLE 12

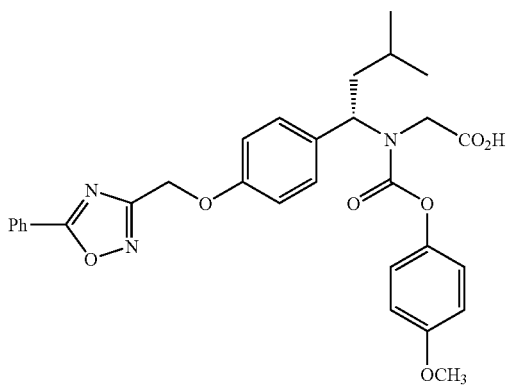

A.

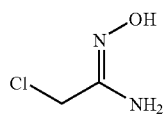

To a vigorously stirred mixture of chloroacetonitre (7.5 g; 0.10 mmol) and hydroxylamine hydrochloride (6.95 g; 0.10 mmol) in H₂O (25 mL) was carefully added Na₂CO₃ (5.3 g; 0.05 mmol) while maintaining the reaction temperature at ≦30° C. The mixture was then stirred at 30° C. for 15 min, then was extracted with Et₂O (2×80 mL). The combined organic extracts were dried (Na₂SO₄) and concentrated in vacuo to give Part A compound (6.9 g; 64%) as a white solid.

B.

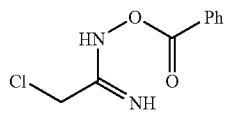

To a 0° C. mixture of Part A compound (1.0 g; 9.0 mmol) and K₂CO₃ (870 mg; 6.3 mmol) in acetone (45 mL) was added dropwise a solution of benzoyl chloride (1.0 mL; 9.0 mmol) in acetone (5 mL). The reaction was allowed to warm to RT and stirred at RT for 30 min. Volatiles were removed in vacuo and the residue was partitioned between H₂O and EtOAc. The organic phase was washed with brine, dried (Na₂SO₄) and concentrated in vacuo to give crude Part B compound (1.50 g; 76%) as a white solid.

C.

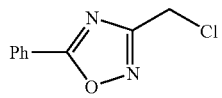

A solution of crude Part B compound (1.50 g) in HOAc (25 mL) was heated to reflux for 1.5 h, after which volatiles were removed in vacuo. The residue was partitioned between H₂O (40 mL) and EtOAc (50 mL); the organic phase was washed with H₂O (2×40 mL), saturated aqueous NaHCO₃ (2×40 mL) and brine (40 mL), dried (MgSO₄) and concentrated in vacuo. The residue was chromatographed (SiO2; continuous gradient from 4:1 to 7:3 hexane:EtOAc) to give Part C compound (840 mg; 61%) as a white solid.

D.

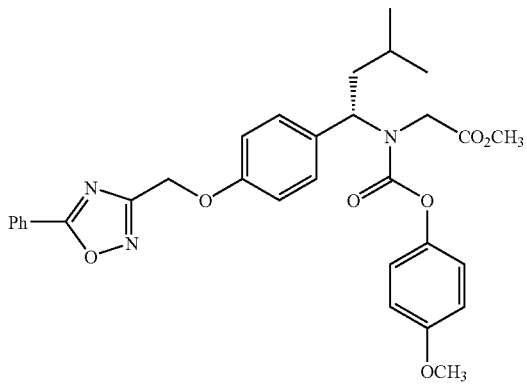

A mixture of crude Part C compound (20 mg; 0.10 mmol), Example 9 Part H compound (8 mg; 0.02 mmol) and K₂CO₃ (5 mg; 0.03 mmol) in MeCN (5 mL) was heated at reflux for 1.5 h. Volatiles were removed in vacuo and the residue was purified by preparative HPLC (continuous gradient from 60:40 A:B to 100% B; A=90:10:0.1 H₂O:MeOH:TFA; B=90:10:0.1 MeOH:H₂O:TFA; 12 min run @ 20 mL/min; detection at 220 nm; YMC ODS 20×100 mm column) to give Part D compound (8 mg; 72%) as a syrup.

E.

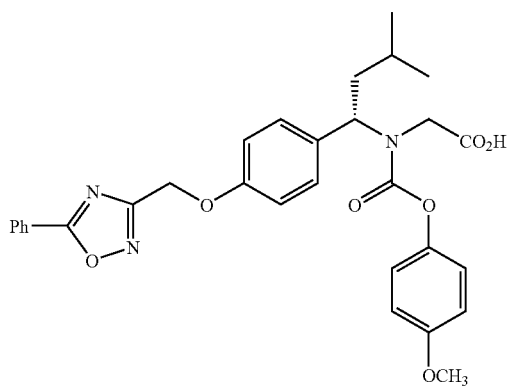

A solution of Part D compound (8 mg; 0.014 mmol) and LiOH.H$_2$O (3 mg; 0.07 mmol) in THF (1 mL) and H$_2$O (0.5 mL) was stirred at RT for 24 h. The solution was acidified to pH 5 with aqueous 1 N HCl, then extracted with EtOAc (3×). The combined organic extracts were concentrated in vacuo and the residue was purified by preparative HPLC (same conditions as for Part D compound) to give the title compound (6 mg; 77%) as a colorless syrup.

[M+H]$^+$=546.2

EXAMPLE 13

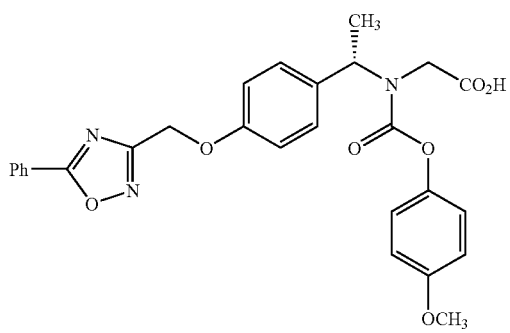

A.

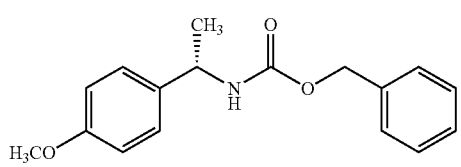

To a RT mixture of (S)-1-(4-methoxyphenyl)-ethylamine (5.45 g, 36 mmol) in THF (50 mL) and aqueous NaHCO$_3$ (6.05 g in 25 mL H$_2$O) was added dropwise benzyl chloroformate (6.20 mL; 43 mmol). The reaction was stirred at RT for 30 min; the organic phase was isolated and concentrated in vacuo. The residue was partitioned between EtOAc and H$_2$O (100 mL each); the organic phase was washed with brine, dried (MgSO$_4$), and concentrated in vacuo to about 30 mL volume. An equivalent volume of hexane (30 mL) was added and Part A compound (9.12 g; 89%) crystallized as colorless needles.

B.

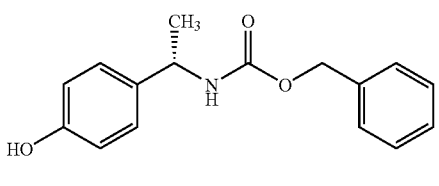

To a −78° C. solution of Part A compound (2.50 g; 8.8 mmol) in anhydrous CH$_2$Cl$_2$ (11 mL) was added dropwise a solution of BBr$_3$ in CH$_2$Cl$_2$ (11.4 mL of a 1.0 M solution; 11.4 mmol) over 25 min. The reaction was allowed to warm to 0° C. and stirred at 0° C. for 6 h, then quenched carefully at −78° C. by dropwise addition of excess MeOH (6 mL). The solution was allowed to warm to 0° C. and stirred at 0° C. for 5 min. The solution was partitioned between CH$_2$Cl$_2$ (60 mL) and H$_2$O (50 mL). The organic phase was washed successively with brine and 5% aqueous NaHCO$_3$ (50 mL each), dried (MgSO$_4$) and concentrated in vacuo. The residue was chromatographed (SiO$_2$; stepwise gradient from 4:1 to 1:1 hex:EtOAc) to furnish Part B compound (1.30 g; 63% yield based on 650 mg (26%) of recovered unreacted Part A compound) as a white solid.

C.

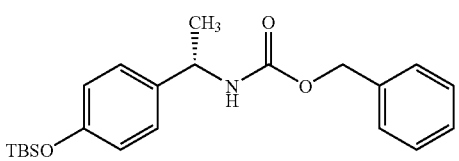

A mixture of tert-butyldimethylsilyl chloride (357 mg; 2.36 mmol), Part B compound (535 mg; 1.97 mmol) and imidazole (161 mg; 2.36 mmol) in DMF (5 mL) was stirred at RT for 2 h. The reaction was partitioned between EtOAc (20 mL) and water (50 mL). The organic phase was washed with water (2×50 mL), dried (Na$_2$SO$_4$), and concentrated in vacuo. The residue was chromatographed (SiO$_2$; hex:EtOAc 3:1) to give Part C compound (320 mg; 42%) as an oil in addition to recovered starting phenol (150 mg; 20%).

D.

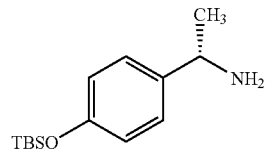

A mixture of Part C compound (320 mg; 0.83 mmol) and 10% palladium on carbon (30 mg) in MeOH (30 mL) was stirred under an atmosphere of H$_2$ (balloon) at RT for 1 h, at which point the reaction was complete by HPLC. The catalyst was filtered off through Celite® and the filtrate was concentrated in vacuo to give Part D compound (230 mg) as a white solid which was used in the next step without further purification.

E.

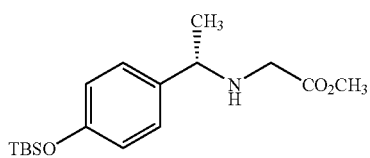

A solution of Part D compound (230 mg), methyl bromoacetate (86 µL; 0.91 mmol) and Et₃N (127 µL; 0.91 mmol) in THF (10 mL) was stirred at RT for 15 h. The reaction mixture was partitioned between H₂O and EtOAc (30 mL) each. The organic phase was washed with brine, dried (MgSO₄) and concentrated in vacuo. The residue was chromatographed (SiO₂; stepwise gradient from hex:EtOAc 9:1 to 1:1) to furnish Part E compound (177 mg; 66% over 2 steps) as an oil.

F.

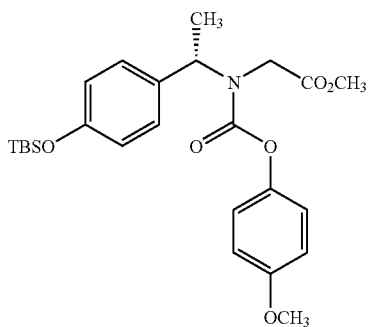

To a solution of Part E compound (9.0 g; 27.9 mmol), NaHCO₃ (4.70 g; 55.8 mmol) in THF:H₂O (240 mL of a 1:1 solution) was added a solution of 4-methoxyphenyl chloroformate (5.0 mL; 33.5 mmol) dropwise. The reaction was stirred at RT for 2 h, then was partitioned between EtOAc (250 mL) and H₂O (200 mL). The organic phase was washed with brine (200 mL), dried (MgSO₄) and concentrated in vacuo. The residue was chromatographed (SiO₂; stepwise gradient from 9:1 to 7:3 hexane:EtOAc) to provide pure Part F compound (12.5 g; 95%).

G.

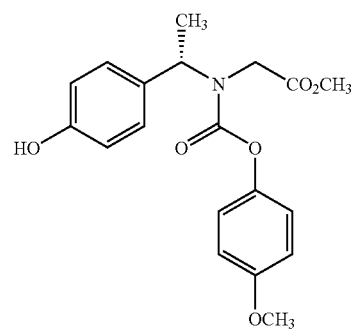

To a solution of Part F compound (12.5 g; 26.4 mmol) in THF (100 mL) was added dropwise tetrabutylammonium fluoride (32 mL of a 1 M solution in THF; 32 mmol). The reaction was stirred at RT for 2 h, then was partitioned between EtOAc (250 mL) and H₂O (200 mL). The organic phase was washed with brine (200 mL), dried (MgSO₄) and concentrated in vacuo. The residue was chromatographed (SiO₂; stepwise gradient from 9:1 to 3:2 hex:EtOAc) to provide Part G compound (8.0 g; 84%) as a syrup.

H.

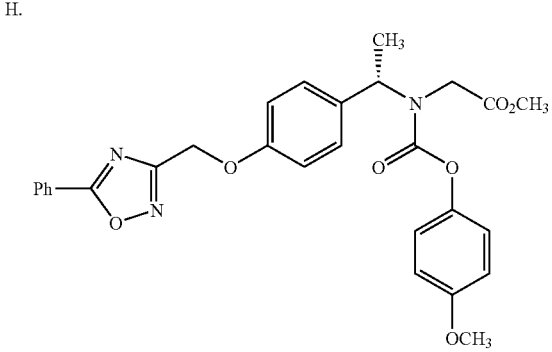

A mixture of crude Example 12 Part C compound (20 mg; 0.10 mmol), Part G compound (8 mg; 0.02 mmol) and K₂CO₃ (5 mg; 0.03 mmol) in MeCN (5 mL) was heated at reflux for 1.5 h. Volatiles were removed in vacuo and the residue was purified by preparative HPLC (same conditions as for Example 12 Part D compound) to give Part H compound (8 mg; 72%) as a syrup.

I.

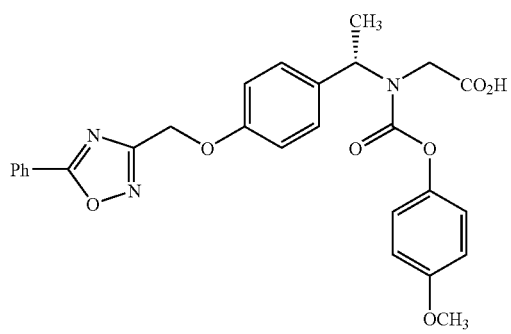

A solution of Part H compound (8 mg; 0.014 mmol) and LiOH.H₂O (3 mg; 0.07 mmol) in THF (1 mL) and H₂O (0.5 mL) was stirred at RT for 24 h. The solution was acidified to pH 5 with aqueous 1 N HCl, then extracted with EtOAc (3×). The combined organic extracts were concentrated in vacuo and the residue was purified by preparative HPLC (same conditions as for Example 12 Part D compound) to give the title compound (6 mg; 77%) as a colorless syrup.

$[M+H]^+=504.2$

EXAMPLE 14

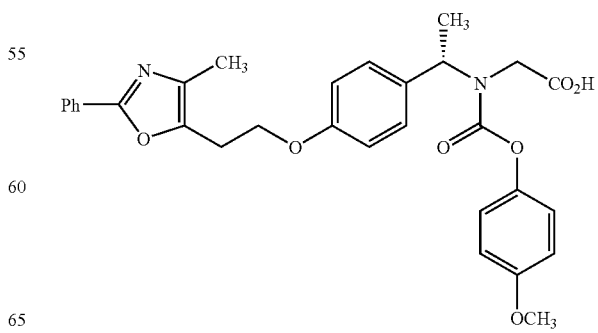

A.

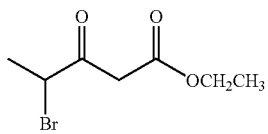

To a 0° C. solution of ethyl propionylacetate (10.0 g, 69.4 mmol) in CHCl₃ (60 mL) was added dropwise a solution of Br₂ (3.6 mL; 69.4 mmol) in CHCl₃ (20 mL) and the resulting mixture was stirred at 0° C. for 0.5 h. The reaction was allowed to warm to RT and stirred at RT for 0.5 h. Air was then bubbled into the mixture for 1 h. Volatiles were then removed in vacuo to yield an oily residue to provide crude Part A compound (15.3 g, >95% yield) as an oil which was used in the next reaction without further purification.

B.

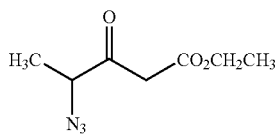

A mixture of Part A compound (400 mg; 1.79 mmol) and sodium azide (136 mg; 2.09 mmol) in acetone (6 mL) and H₂O (1 mL) was stirred at RT for 1 h, then at 50° C. for 1 h. At this point analytical HPLC showed that starting material had been consumed. Volatiles were removed in vacuo and the residue was partitioned between H₂O and CH₂Cl₂. The organic phase was dried (MgSO₄) and concentrated in vacuo. The residue was chromatographed (SiO₂; continuous gradient from hexane to 1:1 hexane:EtOAc) to provide Part B compound (280 mg; 85%) as a pale yellow oil.

C.

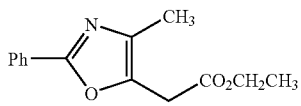

To a solution of Part B compound (100 mg; 0.54 mmol) in dioxane (4 mL) was added resin-bound Ph₃P (540 mg of 3 mmol/g resin; 3 equivalents). The mixture was shaken for 10 min at RT. Benzoyl chloride (70 µL; 0.60 mmol) was added and the reaction mixture was heated at 75° C. for 2 h, at which point the reaction was complete by HPLC. The reaction was filtered and the filtrate was concentrated in vacuo. The residue was chromatographed (SiO₂; continuous gradient from hexane to 1:1 hexane:EtOAc) to provide Part C compound (62 mg; 50%) as a colorless oil.

D.

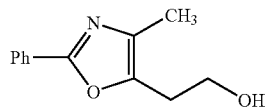

To a 0° C. solution of LiAlH₄ (1.0 mL of a 1 M solution; 1 mmol) was added dropwise a solution of Part C compound (75 mg; 0.031 mmol) in THF. After 30 min at 0° C., the rection was quenched cautiously with H₂O, followed by addition of aqueous NaOH (2 mL of a 3N solution). Volatiles were removed in vacuo and the residue was partitioned between H₂O and CH₂Cl₂. The aqueous phase was extracted with CH₂Cl₂ (2×). The combined organic extracts were concentrated in vacuo and the residue was chromatographed (SiO₂; continuous gradient from 100% hexane to 100% EtOAc) to give Part D compound (55 mg; 89%) as a colorless oil.

E.

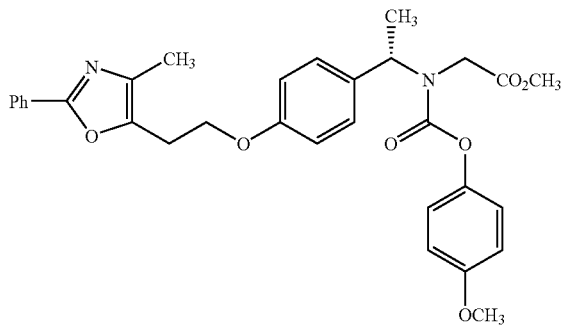

To a 0° C. solution of Part D compound (20 mg; 0.098 mmol), Example 13 Part G compound (33 mg; 0.092 mmol) and Ph₃P (40 mg; 0.15 mmol) in CH₂Cl₂ (2 mL) was added a solution of DEAD (31 µL; 0.20 mmol) in CH₂Cl₂ (2 mL) dropwise. The reaction was allowed to warm to RT and stirred at RT overnight. Volatiles were removed in vacuo and the residue was chromatographed (SiO₂; continuous gradient from 100% hexane to 100% EtOAc) to give Part E compound (32 mg; 61%) as a colorless oil.

F.

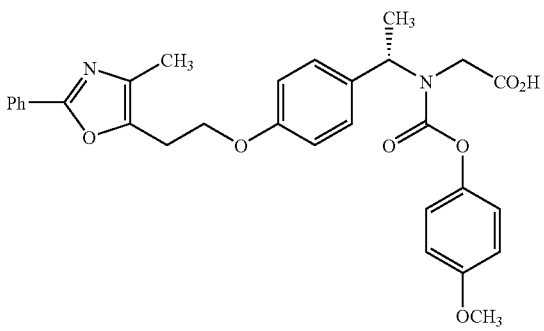

A solution of Part E compound (16 mg; 0.029 mmol) in aqueous LiOH (0.5 mL of a 2N solution) and MeOH/THF (0.5 mL each) was stirred at RT for 4 h. Organic solvents were removed in vacuo and the aqueous phase was acidified to pH 2 with aqueous 1 N HCl. The resultant white precipitate was collected by filtration and dried to give the title compound (9 mg; 60%) as a white solid.

[M+H]⁺=531.2

EXAMPLE 15

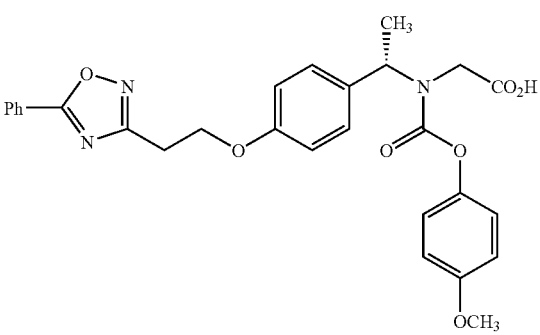

A.

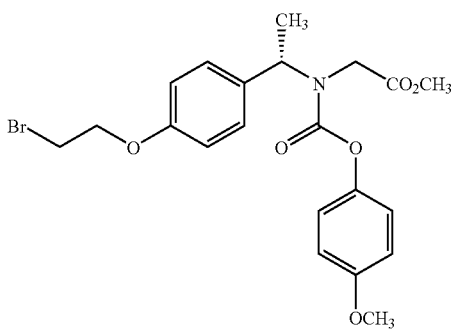

A mixture of Example 13 Part G compound (3.5 g; 9.75 mmol), 1,2-dibromoethane (4.2 mL; 49 mmol) and $K_2CO_3$ (2.2 g; 15.6 mmol) in MeCN (32.5 mL) was heated at 90° C. for 15 h. The mixture was cooled to RT and volatiles were removed in vacuo. The residue was partitioned between $H_2O$ and EtOAc; the organic phase was washed with $H_2O$ and brine, dried ($MgSO_4$) and concentrated in vacuo. The residue was chromatographed ($SiO_2$; continuous gradient from 100% hexane to 1:1 hexane:EtOAc over 45 min; then 1:1 hexane: EtOAc to 100% EtOAc over 10 min) to provide Part A compound (2.0 g; 44%; 66% based on recovered starting material) as an oil.

B.

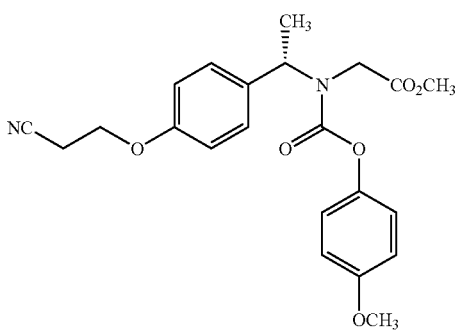

A mixture of Part A compound (2.0 g; 4.3 mmol) and tetrabutylammonium cyanide (3.5 g; 12.9 mmol) in $CH_2Cl_2$ (21.5 mL) was stirred at RT for 2.5 h. Volatiles were removed in vacuo, and the residue was chromatographed ($SiO_2$; continuous gradient from 100% hexane to 1:1 hexane:EtOAc over 45 min, then 1:1 hexane:EtOAc to 100% EtOAc over 10 min) to provide Part B compound (1.49 g; 84%) as an oil.

C.

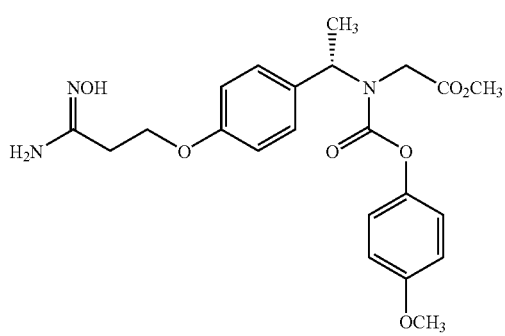

A mixture of Part B compound (450 mg; 1.14 mmol) and hydroxylamine (230 mg of a 50% wt/wt aqueous solution) in MeOH:$H_2O$ (8.4 mL of a 2:1 solution) was heated ato 95° C. for 4 h. The reaction was cooled to RT and volatiles were removed in vacuo. The residue was purified by preparative HPLC (continuous gradient from 70:30 A:B to 100% B for 25 min @ 25 ml/min; A=90:10:0.1 $H_2O$:MeOH:TFA; B=90:10:0.1 MeOH:$H_2O$:TFA; detection at 220 nm; YMC ODS 30×250 mm column; retention time=17.1 min) to provide Part C compound (390 mg; 77%) as an oil.

D.

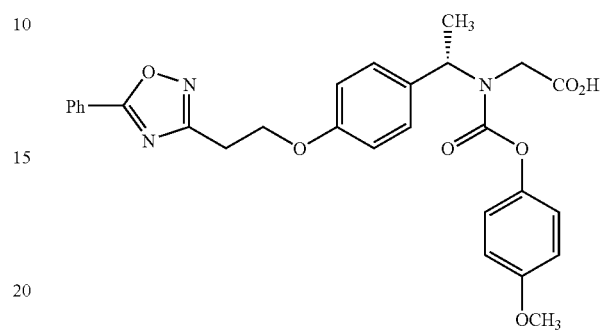

To a solution of Part C compound (43 mg; 0.097 mmol) in pyridine (970 μL) was added benzoyl chloride (100 μL; 0.86 mmol). The mixture was stirred in a sealed tube at 115° C. for 3 h, then was cooled to RT and partitioned between $H_2O$ and EtOAc. The organic phase was washed with $H_2O$ and brine, dried ($MgSO_4$) and concentrated in vacuo. The residue was purified by preparative HPLC (continuous gradient from 60:40 A:B to 100% B for 25 min, then held at 100% B for 10 min at 25 mL/min; A=90:10:0.1 $H_2O$:MeOH:TFA; B=90:10:0.1 MeOH:$H_2O$:TFA; detection at 220 nm; YMC ODS 30×250 mm column; retention time=29.4 min) to provide Part D compound (12 mg; 23%) as an oil.

E.

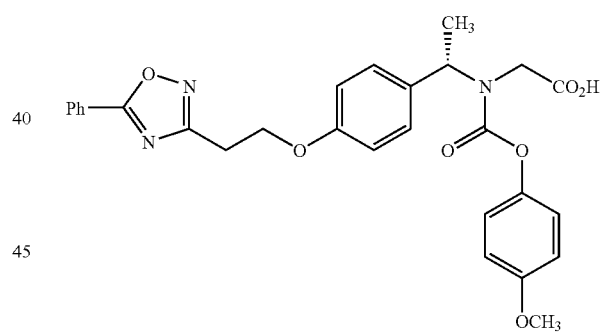

A solution of Part D compound (6 mg; 0.011 mmol) and LiOH.$H_2O$ (2.4 mg; 0.06 mmol) in THF (2 mL) and $H_2O$ (1 mL) was stirred at RT overnight. EtOAc was added and the mixture was acidified to pH 2 with aqueous 1 N HCl; the organic phase was washed with $H_2O$ and brine, dried ($MgSO_4$) and concentrated in vacuo. The residue was purified by preparative HPLC (from 70:30 A:B to 100% B for 10 min, then held at 100% B for 5 min at 20 mL/min; A=90:10:0.1 $H_2O$:MeOH:TFA; B=90:10:0.1 MeOH:$H_2O$:TFA; detection at 220 nm; YMC ODS 20×100 mm column; retention time=11.2 min) to give the title compound (4.0 mg; 68%) as an oil.

$[M+H]^+=518.2$

EXAMPLES 16 TO 17

The following phenyloxadiazole carbamate acids were synthesized according to the synthetic sequence described for Example 15:

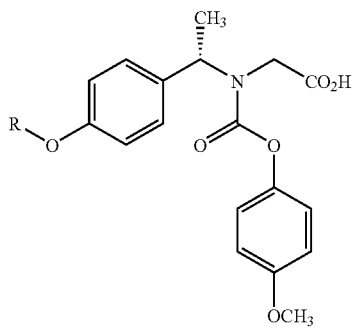

| Example No. | R | [M + H]+ |
|---|---|---|
| 16 | 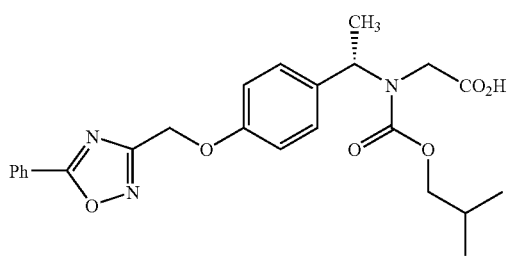 | 602.2 |
| 17 | 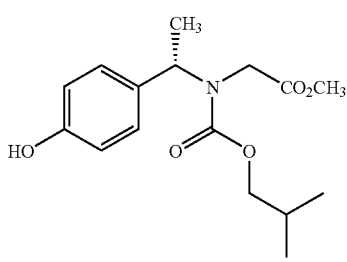 | 532.2 |

EXAMPLE 18

A.

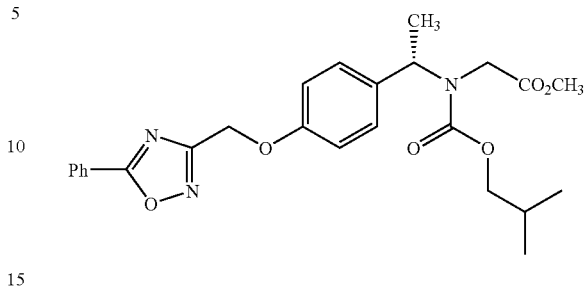

To a solution of Example 13 Part E compound (3.60 g; 11.1 mmol), NaHCO₃ (1.21 g; 14.4 mmol) in dioxane:H₂O (75 mL of a 2:1 solution) was added isobutyl chloroformate (1.87 mL; 14.4 mmol) dropwise. The reaction was stirred at RT for 2 h, then partitioned between EtOAc and H₂O. The organic phase was washed with brine, dried (MgSO₄) and concentrated in vacuo to provide the crude TBS-phenol carbamate. This material was dissolved in THF (50 mL) and tetrabutylammonium fluoride (4.17 mL of a 75% aqueous solution) was added. The reaction was stirred at RT for 40 min, after which volatiles were removed in vacuo. The residue was chromatographed (SiO₂; continuous gradient from 9:1 to 2:3 hexane:EtOAc over 40 min; then 2:3 hexane:EtOAc to 100% EtOAc over 15 min) to provide Part A compound (3.0 g; 87% over 2 steps) as a solid.

B.

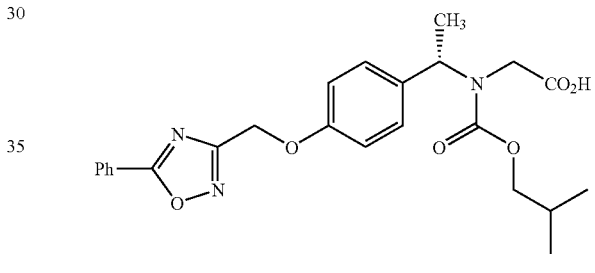

A mixture of Part A compound (45 mg; 0.146 mmol), Example 12 Part C compound (XX mg; 0.292 mmol) and K₂CO₃ (40 mg; 0.292 mmol) in MeCN (1 mL) was stirred at 90° C. overnight. After cooling to RT, the mixture was partitioned between EtOAc and H₂O. The organic phase was washed with brine, dried (MgSO₄) and concentrated in vacuo. The residue was purified by preparative HPLC (continuous gradient from 50:50 A:B to 100% B; A=90:10:0.1 H₂O:MeOH:TFA; B=90:10:0.1 MeOH:H₂O:TFA; 10 min run @ 20 mL/min with 5 min hold time; detection at 220 nm; YMC ODS 20×100 mm column) to provide Part B compound as an oil.

C.

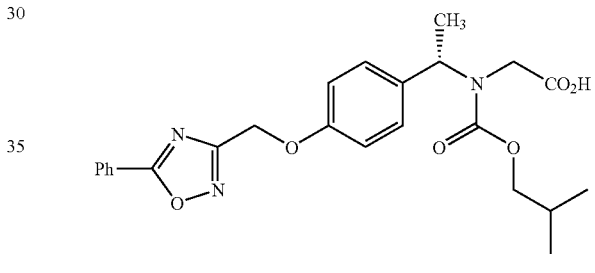

A solution of Part B compound and LiOH.H₂O (18 mg; 0.44 mmol) in THF (0.7 mL) and H₂O (0.35 mL) was stirred at 50° C. for 3 h. EtOAc was added and the mixture was acidified to ~pH 2 with aqueous 1 N HCl; the organic phase was washed with H₂O and brine, dried (MgSO₄) and concentrated in vacuo. The residue was purified by preparative HPLC (continuous gradient from 60:40 A:B to 100% B for 10 min, then held at 100% B for 5 min @ 20 mL/min; A=90:10:0.1 H₂O:MeOH:TFA; B=90:10:0.1 MeOH:H₂O:TFA; detection at 220 nm; YMC ODS 20×100 mm column; retention time=10.2 min) to give the title compound (48 mg; 73% over 2 steps) as a solid.

[M+H]+=454.2

EXAMPLE 19

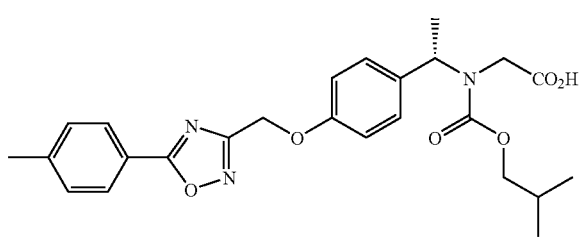

A.

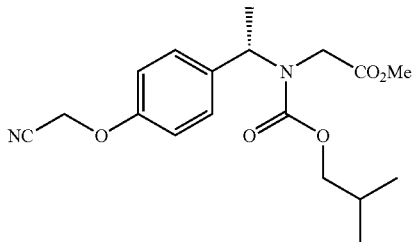

A mixture of Example 18 Part A compound (850 mg; 2.75 mmol) and α-chloroacetonitrile (0.348 mL; 5.50 mmol) and K₂CO₃ (760 mg; 5.50 mmol) in CH₃CN (9.2 mL) was stirred at 90° C. for 3 h, then was cooled to RT and partitioned between EtOAc (95 mL) and H₂O (45 mL). The organic phase was washed with brine (100 mL), dried (MgSO₄) and concentrated in vacuo. The residue was chromatographed (SiO₂; continuous gradient from 100% hex to 100% EtOAc) to give Part A compound (910 mg; 95%) as a colorless oil.

B.

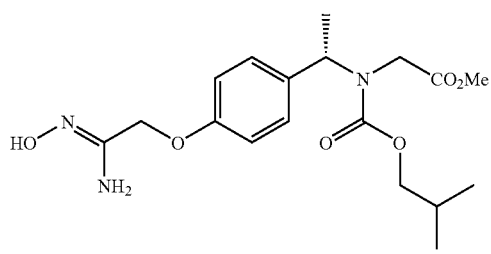

A mixture of Part A compound (910 mg; 2.61 mmol) and hydroxylamine (517 mg of a 50% solution in water; 7.83 mmol) in MeOH (11.6 mL) and H₂O (5.8 mL) was stirred at 95° C. for 6 h, then was cooled to RT and stirred at RT for another 6 h, after which volatiles were removed in vacuo. The residue was partitioned between EtOAc (120 mL) and H₂O (65 mL). The organic phase was washed with brine (20 mL), dried (MgSO₄) and concentrated in vacuo to provide crude Part B compound (901 mg; 91%) as an oil, which was used in the next step without further purification.

C.

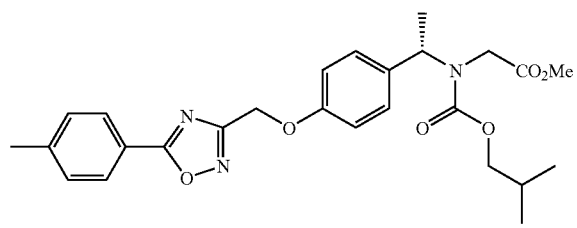

A mixture of Part B compound (56 mg; 0.147 mmol) and p-toluoyl chloride (38.9 µL; 0.294 mmol) in pyridine (1.4 mL) was shaken at 110° C. for 14 h, after which the reaction mixture was cooled to RT and partitioned between EtOAc (10 mL) and H₂O (5 mL). The organic phase was washed with brine (20 mL), and concentrated in vacuo; the residue was purified by preparative HPLC (as described for Example 15 Part E compound except that a continuous gradient from 50:50 Solvent A:Solvent B to 100% B over 10 min was used, followed by 4 min hold at 100% B) to give Part C compound (12.6 mg; 18%) as an oil.

D.

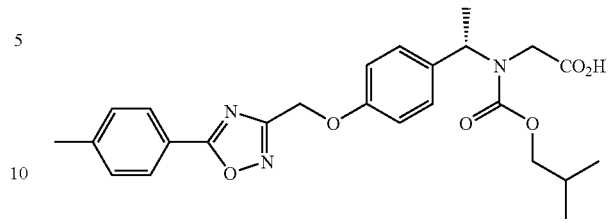

A solution of Part C compound (12.6 mg; 0.0262 mmol) and LiOH.H₂O (30.8 mg; 0.735 mmol) in THF (1 mL) and H₂O (0.5 mL) was stirred at RT for 15 h, after which the mixture was acidified to pH 2 with aqueous 1 N HCl. The mixture was partitioned between EtOAc (10 mL) and H₂O (5 mL). The organic phase was washed with brine (20 mL), dried (MgSO₄) and concentrated in vacuo; the residue was purified by preparative HPLC (as described for Example 15 Part E compound except that a continuous gradient from 40:60 Solvent A:Solvent B to 100% B over 10 min was used, followed by 4 min hold at 100% B) to give the title compound (8.8 mg; 72%) as an oil.

$[M'H]^+=468.0$

EXAMPLES 20-47

Examples 20-47 were prepared in a similar fashion to Example 19 (from Example 19 Part B compound) using a variety of appropriate acid chlorides.

| Example # | R | $[M+H]^+$ |
|---|---|---|
| 20 | Cl-C₆H₄- | 488.2 |
| 21 | 3,5-F₂-C₆H₃- | 490.3 |
| 22 | t-Bu-C₆H₄- | 510.2 |
| 23 | F₃C-C₆H₄- | 522.2 |

-continued

| Example # | R | [M + H]$^+$ |
|---|---|---|
| 24 | 4-(F$_3$CO)-C$_6$H$_4$- | 538.1 |
| 25 | 3,5-(F$_3$C)$_2$-C$_6$H$_3$- | 590.2 |
| 26 | 3-CH$_3$-C$_6$H$_4$- | 468.2 |
| 27 | 3-(F$_3$C)-C$_6$H$_4$- | 522.1 |
| 28 | 3-(F$_3$CO)-C$_6$H$_4$- | 538.3 |
| 29 | 2-CH$_3$-C$_6$H$_4$- | 468.1 |
| 30 | PhCH$_2$- | 468.1 |
| 31 | PhCH$_2$CH$_2$- | 482.1 |
| 32 | 4-(CH$_3$O)-C$_6$H$_4$- | 484.1 |

-continued

| Example # | R | [M + H]$^+$ |
|---|---|---|
| 33 | 3-(CH$_3$O)-C$_6$H$_4$- | 484.1 |
| 34 | 2-(OCH$_3$)-C$_6$H$_4$- | 484.0 |
| 35 | 3,4-methylenedioxyphenyl | 498.1 |
| 36 | 4-(CH$_3$O)-C$_6$H$_4$-CH$_2$- | 498.1 |
| 37 | 4-Cl-C$_6$H$_4$-CH$_2$- | 502.1 |
| 38 | 2-(CF$_3$)-C$_6$H$_4$- | 522.0 |
| 39 | 4-F-C$_6$H$_4$- | 471.8 |
| 40 | 3-F-C$_6$H$_4$- | 472.0 |

-continued

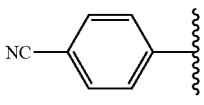

| Example # | R | [M + H]+ |
|---|---|---|
| 41 | 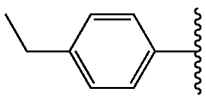 | 479.2 |
| 42 | 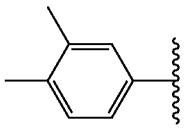 | 482.2 |
| 43 | 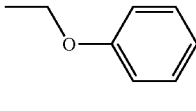 | 482.1 |
| 44 | 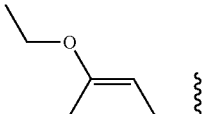 | 498.1 |
| 45 | 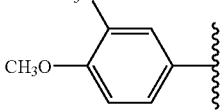 | 498.1 |
| 46 | 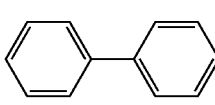 | 514.1 |
| 47 | 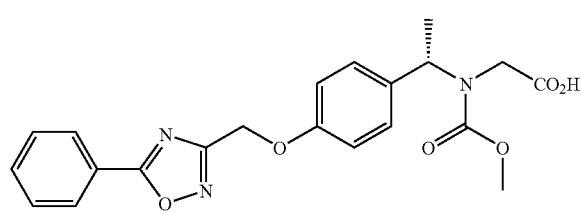 | 530.0 |

EXAMPLE 48

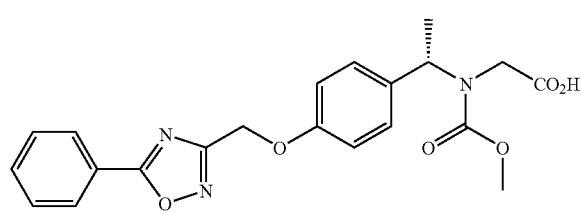

A.

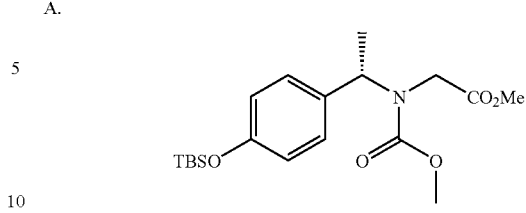

A mixture of Example 13 Part E compound (203 mg; 0.628 mmol), methyl chloroformate (0.063 mL; 0.817 mmol) and NaHCO$_3$ (69 mg; 0.817 mmol) in dioxane:H$_2$O (3.14 mL of a 2:1 solution) was stirred at RT for 14 h, after which the reaction was partitioned between EtOAc (10 mL) and H$_2$O (5 mL). The organic phase was washed with brine (10 mL), dried (MgSO$_4$) and concentrated in vacuo to give crude Part A compound which was used in the next step without further purification.

B.

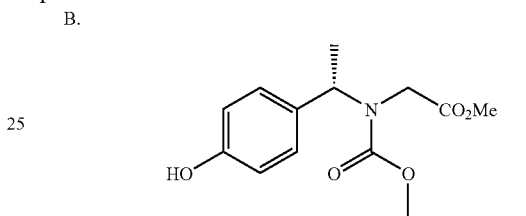

A solution of crude Part A compound and (n-Bu)$_4$NF (237 μL; 0.817 mmol) in THF (2 mL) was stirred at RT for 30 min, after which volatiles were removed in vacuo. The residue was chromatographed (SiO$_2$; continuous gradient from 9:1 hex:EtOAc to 100% EtOAc) to give Part B compound (124 mg; 74% for two steps) as a colorless oil.

C.

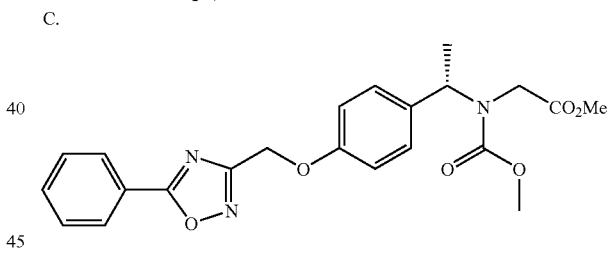

A mixture of Part B compound (14.5 mg; 0.0543 mmol), Example 12 Part C compound ((13.7 mg; 0.0706 mmol) and K$_2$CO$_3$ (9.8 mg; 0.0706 mmol) in CH$_3$CN (1 mL) was shaken at 88° C. for 14 h, then was cooled to RT and partitioned between EtOAc (10 mL) and H$_2$O (5 mL). The organic phase was washed with brine (20 mL) and concentrated in vacuo to give crude Part C compound, which was used in the next step without further purification.

D.

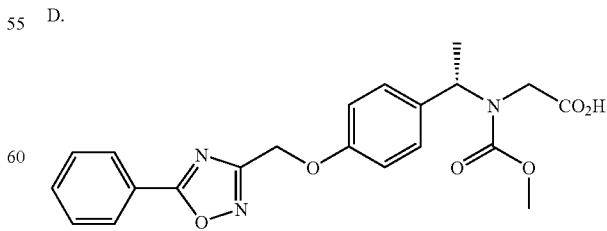

A solution of crude Part C compound and LIOH.H$_2$O (6.8 mg; 0.163 mmol) in THF (1 mL) and H$_2$O (0.5 mL) was stirred at RT for 16 h, after which the mixture was acidified to pH 2 with aqueous 1 N HCl. The mixture was partitioned between EtOAc (10 mL) and H₂O (5 mL). The organic phase was washed with brine (20 mL), dried (MgSO₄) and concentrated in vacuo; the residue was purified by preparative HPLC (as described for Example 15 Part E compound except that a continuous gradient from 40:60 Solvent A:Solvent B to 100% B over 10 min was used, followed by 4 min hold at 100% B) to give the title compound (15.5 mg; 69% for two steps) as an oil.

$[M+H]^+$=412.2

EXAMPLES 49-53

Examples 49-53 were prepared using the same sequence as for the synthesis of Example 48 (from Example 13 part E compound) using appropriate chloroformates (instead of methyl chloroformate asfor Example 48).

| Example No. | R | $[M + H]^+$ |
| --- | --- | --- |
| 49 |  | 426.2 |
| 50 |  | 440.3 |
| 51 |  | 440.4 |
| 52 |  | 454.2 |
| 53 |  | 481.2 |

EXAMPLE 54

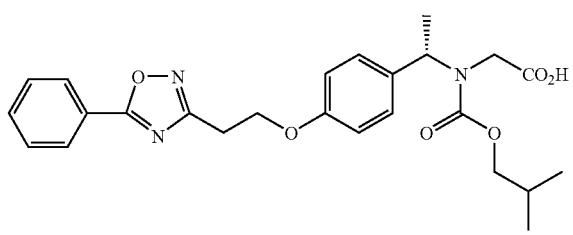

-continued

A.

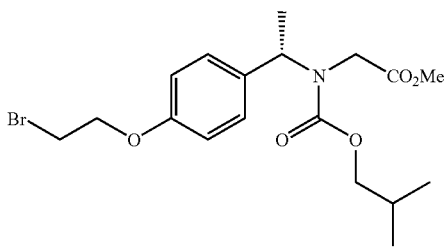

A mixture of Example 18 Part A compound (1000 mg; 3.24 mmol) and 1,2-dibromoethane (1.7 mL; 19.4 mmol) and K₂CO₃ (896 mg; 6.48 mmol) in CH₃CN (9.2 mL) was stirred at 90° C. for 41 h, then was cooled to RT and partitioned between EtOAc (100 mL) and H₂O (50 mL). The organic phase was washed with brine (100 mL), dried (MgSO₄) and concentrated in vacuo. The residue was chromatographed (SiO₂; continuous gradient from 100% hex to 100% EtOAc) to give Part A compound (868 mg; 65%) as a colorless oil.

B.

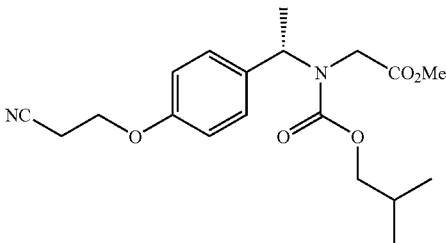

A mixture of Part A compound (868 mg; 2.09 mmol) and tetrabutylammonium cyanide (1.68 g; 6.27 mmol) in CH₂Cl₂ (10.5 mL) was stirred at RT for 15 h, after which volatiles were removed in vacuo; the residue was chromatographed (SiO₂; continuous gradient from 100% hex to 100% EtOAc) to give Part B compound (730 mg; 96%) as a colorless oil.

C.

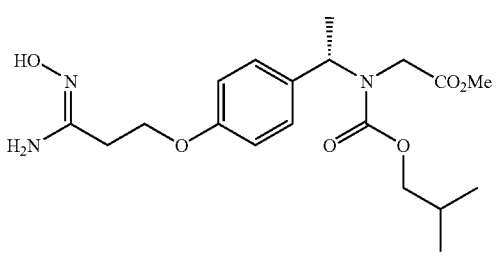

A mixture of Part B compound (730 mg; 2.02 mmol) and hydroxylamine (400 mg of a 50% solution in water; 6.06 mmol) in MeOH (9.0 mL) and H₂O (4.5 mL) was stirred at 95° C. for 4 h, after which volatiles were removed in vacuo. The residue was partitioned between EtOAc (120 mL) and H₂O (65 mL). The organic phase was washed with brine (70 mL), dried (MgSO₄) and concentrated in vacuo to provide crude Part C compound (750 mg; 94%) as an oil.

D.

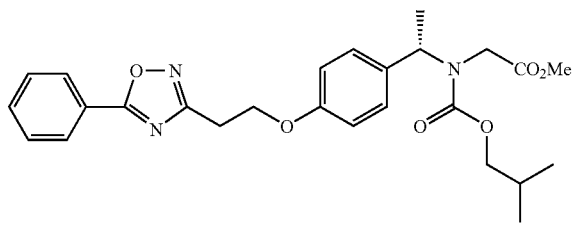

To a solution of Part C compound (50 mg; 0.127 mmol) in pyridine (1.3 mL) was added benzoyl chloride (29.5 µL; 0.254 mmol). The mixture was shaken at 110° C. for 15 h, then was cooled to RT and partitioned between EtOAc (10 mL) and $H_2O$ (5 mL). The organic phase was washed with brine (20 mL), and concentrated in vacuo to give crude Part D compound, which was used in the next step without further purification.

E.

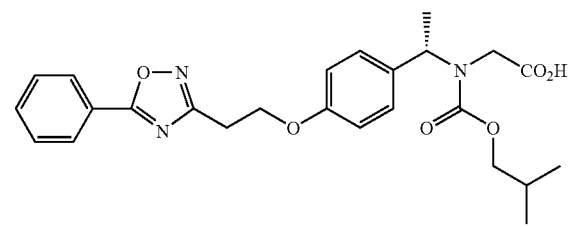

To a solution of crude Part D compound and $LiOH.H_2O$ (26.6 mg; 0.635 mmol) in THF (0.8 mL) and $H_2O$ (0.4 mL) was stirred at RT for 25 h, after which the mixture was acidified to pH 2 with aqueous 1 N HCl. The mixture was partitioned between EtOAc (10 mL) and $H_2O$ (5 mL). The organic phase was washed with brine (20 mL), dried ($MgSO_4$) and concentrated in vacuo; the residue was purified by preparative HPLC (as described for Example 15 Part E compound except that a continuous gradient from 40:60 Solvent A:Solvent B to 100% B over 10 min was used, followed by 4 min hold at 100% B) to give the title compound (6.5 mg; 11% for two steps) as an oil.

$[M+H]^+=468.1$

EXAMPLES 55-65

Examples 55-65 were prepared using the analogous sequence for the synthesis of Example 54 (starting from Example 54 Part C compound), but using a variety of appropriate acid chlorides instead of benzoyl chloride.

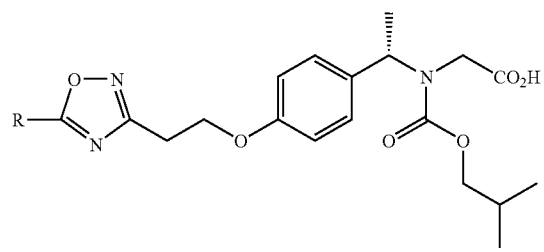

| Example No. | R | $[M + H]^+$ |
|---|---|---|
| 55 | 4-methylphenyl | 482.1 |
| 56 | 3-methylphenyl | 482.2 |
| 57 | 4-Cl-phenyl | 502.1 |
| 58 | 4-tBu-phenyl | 524.2 |
| 59 | 4-$F_3C$-phenyl | 536.1 |
| 60 | 3-$F_3C$-phenyl | 536.2 |
| 61 | 4-$F_3CO$-phenyl | 552.0 |
| 62 | 3-$F_3CO$-phenyl | 552.1 |
| 63 | $PhCH_2$ | 482.1 |
| 64 | $PhCH_2CH_2$ | 496.2 |

-continued

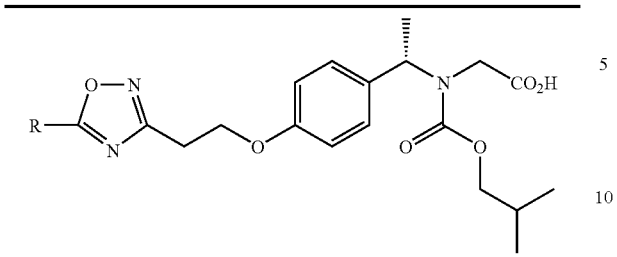

| Example No. | R | [M + H]+ |
|---|---|---|
| 65 | 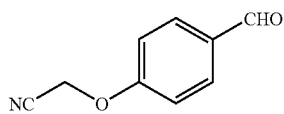 | 516.2 |

EXAMPLE 66

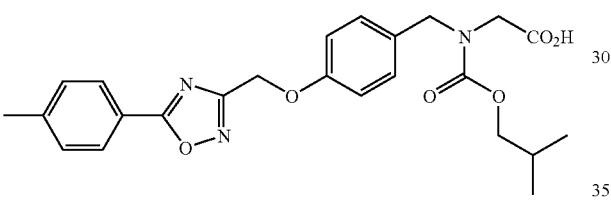

A.

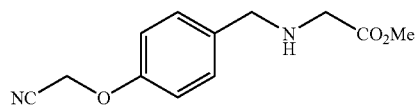

A mixture of 4-hydroxybenzaldehyde (5.2 g; 42.6 mmol), α-chloroacetonitrile (4.0 mL; 63.2 mmol) and $K_2CO_3$ (6.7 g; 48.5 mmol) in $CH_3CN$ (106.5 mL) was stirred at 90° C. for 5 h, then was cooled to RT and partitioned between EtOAc (200 mL) and $H_2O$ (110 mL). The organic phase was washed with brine (200 mL), dried ($MgSO_4$) and concentrated in vacuo to provide crude Part A compound, which was used in the next step without further purification.

B.

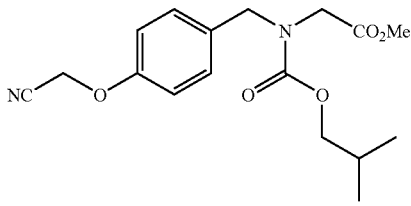

A mixture of crude Part A compound and glycine methylester hydrochloride (5.9 g; 46.9 mmol) and $Et_3N$ (6.5 mL; 46.9 mmol) and 4A molecular sieves (2 g) in MeOH (142 mL) was stirred at RT for 13 h, after which $NaBH_4$ (1.8 g; 46.9 mmol) was slowly added. The mixture was stirred at RT for 1 h, after which volatiles were removed in vacuo. The residue was partitioned between EtOAc (150 mL) and $H_2O$ (80 mL). The organic phase was washed with brine (150 mL), dried ($MgSO_4$) and concentrated in vacuo to give Part B compound (6.0 g; 60% for two steps) as a colorless oil.

C.

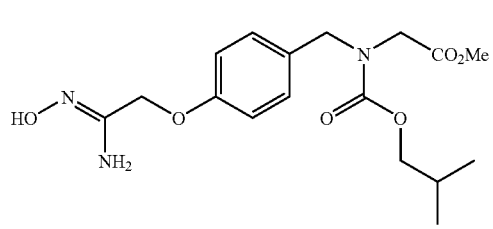

A mixture of Part B compound (2.1 g; 8.97 mmol), isobutyl chloroformate (1.52 mL; 11.7 mmol) and $NaHCO_3$ (983 mg; 11.7 mmol) in dioxane:$H_2O$ (60 mL of a 2:1 solution) was stirred at RT for 2 h, then was partitioned between EtOAc (120 mL) and $H_2O$ (70 mL). The organic phase was washed with brine (140 mL), dried ($MgSO_4$) and concentrated in vacuo. The residue was chromatographed ($SiO_2$; continuous gradient from 100% hex to 100% EtOAc) to give Part C compound (2.84 g; 95%) as a colorless oil.

D.

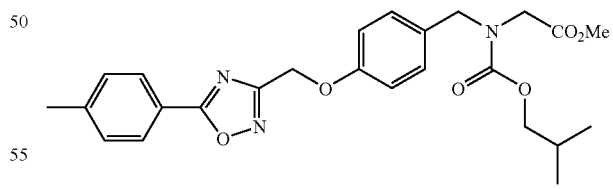

A mixture of Part C compound (1.7 g; 5.09 mmol) and hydroxylamine (1.0 g of a 50% solution in water; 15.27 mmol) in MeOH (22.6 mL) and $H_2O$ (11.3 mL) was stirred at 95° C. for 5 h, after which volatiles were removed in vacuo. The residue was partitioned between EtOAc (140 mL) and $H_2O$ (80 mL). The organic phase was washed with brine (20 mL), dried ($MgSO_4$) and concentrated in vacuo to provide crude Part D compound (1.77 g; 95%) as an oil, which was used in the next step without further purification.

E.

To a solution of Part D compound (50 mg; 0.136 mmol) in solution of pyridine (1.1 mL) was added p-toluoyl chloride (42.1 μL; 0.272 mmol). The mixture was shaken at 115° C. for 6 h, then was concentrated in vacuo; the residue was purified by preparative HPLC (as described for Example 15 Part E compound except that a continuous gradient from 40:60 Solvent A:Solvent B to 100% B over 10 min was used, followed by 4 min hold at 100% B) to give Part E compound (7.6 mg; 12%) as an oil.

F.

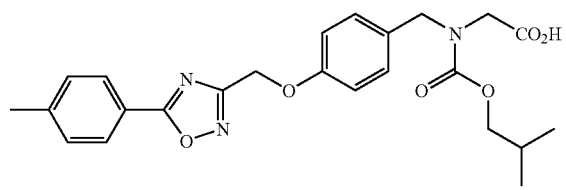

A solution of Part E compound (7.6 mg; 0.0163 mmol) and LiOH.H$_2$O (28.5 mg; 0.68 mmol) in THF (0.86 mL) and H$_2$O (0.43 mL) was stirred at RT for 25 h, after which the reaction mixture was acidified to pH 2 with aqueous 1 N HCl. The mixture was partitioned between EtOAc (10 mL) and H$_2$O (5 mL). The organic phase was washed with brine (20 mL), dried (MgSO$_4$) and concentrated in vacuo; the residue was purified by preparative HPLC (as described for Example 15 Part E compound except that a continuous gradient from 40:60 Solvent A:Solvent B to 100% B over 10 min was used, followed by 4 min hold at 100% B) to give the title compound (4.5 mg; 61%) as an oil.
[M+H]$^+$=454.4

EXAMPLES 67-75

Examples 67-75 were prepared using the same sequence as for the synthesis of Example 66 (starting from Example 66 Part D compound) using a variety of appropriate acid chlorides (instead of p-toluoyl chloride).

| Example No. | R | [M + H]$^+$ |
|---|---|---|
| 67 | MeO-C$_6$H$_4$- | 470.0 |
| 68 | 3-MeO-C$_6$H$_4$- | 470.0 |
| 69 | benzo[1,3]dioxol-5-yl | 484.4 |
| 70 | 4-tBu-C$_6$H$_4$- | 496.1 |
| 71 | 4-F$_3$CO-C$_6$H$_4$- | 524.1 |

-continued

| Example No. | R | [M + H]$^+$ |
|---|---|---|
| 72 | 3-F$_3$CO-C$_6$H$_4$- | 524.1 |
| 73 | C$_6$H$_5$- | 440.0 |
| 74 | Ph-CH$_2$CH$_2$- | 468.1 |
| 75 | 4-Cl-C$_6$H$_4$-CH$_2$- | 487.9 |

EXAMPLE 76

A.

A mixture of (R)-(+)-{1-[4-(tert-butyl-dimethyl-silyloxy)-phenyl]-ethylamino}-acetic acid methyl ester [2.8 g; 8.67 mmol; obtained from (R)-(+)-1-(4-methoxy-phenyl)-ethylamine according to the procedure described for the synthesis of Example 13 Part E compound] and isobutyl chloroformate (1.5 mL; 11.3 mmol) and NaHCO₃ (0.95 g; 11.3 mmol) in dioxane:H₂O (58 mL of a 2:1 solution) was stirred at RT for 1 h, after which the reaction was partitioned between EtOAc (170 mL) and H₂O (90 mL). The organic phase was washed with brine (140 mL), dried (MgSO₄) and concentrated in vacuo to give crude Part A compound, which was used in the next step without further purification.

B.

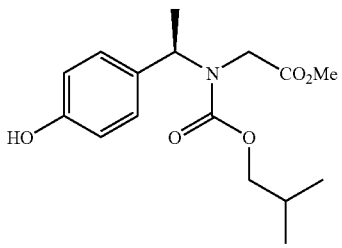

To a solution of crude Part A compound in THF (28.9 mL) was added (n-Bu)₄NF (9.54 mL of a 1 M solution in THF; 9.54 mmol). The mixture was stirred at RT for 45 min, then was partitioned between EtOAc (150 mL) and H₂O (70 mL). The organic phase was washed with brine (140 mL), dried (MgSO₄) and concentrated in vacuo to give Part B compound (2.4 g; 90% for 2 steps) as a colorless oil.

C.

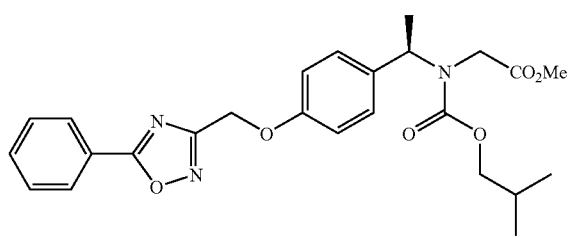

A mixture of Part B compound (46 mg; 0.149 mmol), Example 12 Part C compound ((37.8 mg; 0.194 mmol) and K₂CO₃ (26.8 mg; 0.194 mmol) in CH₃CN (2 mL) was stirred at 90° C. for 16 h, after which the reaction mixture was cooled to RT and partitioned between EtOAc (18 mL) and H₂O (8 mL). The organic phase was washed with brine (20 mL), and concentrated in vacuo; the residue was purified by preparative HPLC (as described for Example 15 Part E compound except that a continuous gradient from 50:50 Solvent A:Solvent B to 100% B over 10 min was used, followed by 4 min hold at 100% B) to give Part C compound (48.3 mg; 69%) as an oil.

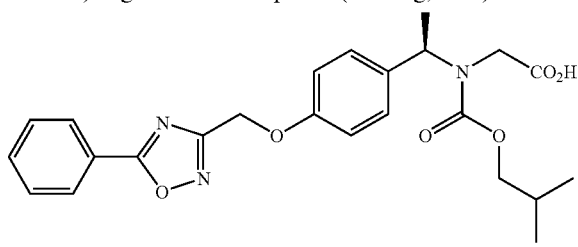

A solution of Part C compound (48.3 mg, 0.103 mmol) and LiOH·H₂O (18.8 mg; 0.447 mmol) in THF (1.2 mL) and H₂O (0.6 mL) was stirred at RT for 15 h, then was acidified to pH 2 with aqueous 1 N HCl. The mixture was partitioned between EtOAc (14 mL) and H₂O (8 mL). The organic phase was washed with brine (15 mL), dried (MgSO₄) and concentrated in vacuo; the residue was purified by preparative HPLC (as described for Example 15 Part E compound except that a continuous gradient from 40:60 Solvent A:Solvent B to 100% B over 10 min was used, followed by 4 min hold at 100% B) to give the title compound (40.3 mg; 86%) as an oil.

[M+H]⁺=454.0

EXAMPLE 77

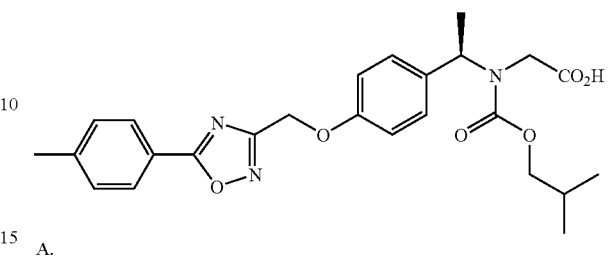

A.

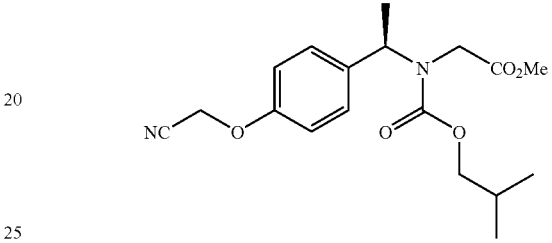

A mixture of Example 76 Part B compound (1.2 g; 3.88 mmol), α-chloroacetonitrile (0.49 mL; 7.76 mmol) and K₂CO₃ (1.07 g; 7.76 mmol) in CH₃CN (12.9 mL) was stirred at 90° C. for 10 h, then was cooled to RT and partitioned between EtOAc (95 mL) and H₂O (45 mL). The organic phase was washed with brine (100 mL), dried (MgSO₄) and concentrated in vacuo. The residue was chromatographed (SiO₂; continuous gradient from 100% hex to 3:2 hex:EtOAc) to give Part A compound (1.17 g; 87%) as a colorless oil.

B.

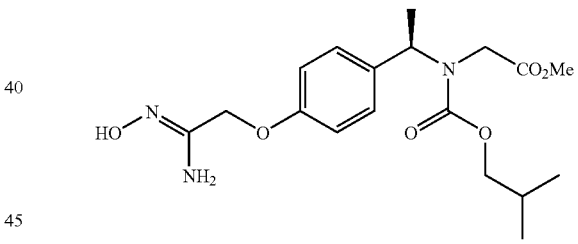

A solution of Part A compound (1.17 g; 3.36 mmol) and hydroxylamine (0.65 g of a 50% solution in water; 9.7 mmol) in MeOH (17.2 mL) and H₂O (8.6 mL) was stirred at 95° C. for 6 h, then was cooled to RT and concentrated in vacuo. The residue was partitioned between EtOAc (140 mL) and H₂O (80 mL). The organic phase was washed with brine (80 mL), dried (MgSO₄) and concentrated in vacuo to provide crude Part B compound (1.19 g; 93%) as an oil, which was used in the next step without further purification.

C.

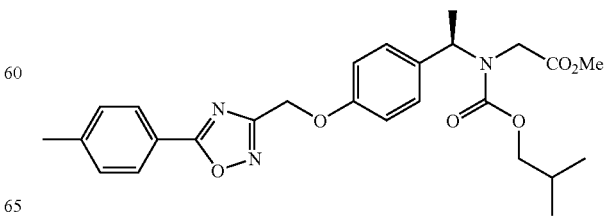

To a solution of Part B compound (40 mg; 0.105 mmol) in pyridine (1.0 mL) was added p-toluoyl chloride (32.5 mg; 0.21 mmol). The mixture was shaken at 115° C. for 6 h, then was cooled to RT and concentrated in vacuo; the residue was purified by preparative HPLC (as described for Example 15 Part E compound except that a continuous gradient from 40:60 Solvent A:Solvent B to 100% B over 10 min was used, followed by 4 min hold at 100% B) to give Part E compound (5.3 mg; 10%) as an oil.

D.

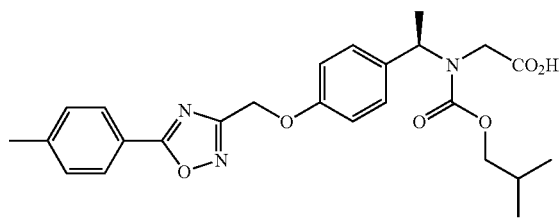

A solution of Part C compound (5.3 mg; 0.011 mmol) and LiOH.H$_2$O (17.6 mg; 0.42 mmol) in THF (0.80 mL) and H$_2$O (0.40 mL) was shaken at 50° C. for 6 h, then was cooled to RT and acidified to pH 2 with aqueous 1 N HCl. The mixture was partitioned between EtOAc (10 mL) and H$_2$O (5 mL). The organic phase was washed with brine (10 mL), dried (MgSO$_4$) and concentrated in vacuo; the residue was purified by preparative HPLC (as described for Example 15 Part E compound except that a continuous gradient from 40:60 Solvent A:Solvent B to 100% B over 10 min was used, followed by 4 min hold at 100% B) to give the title compound (2.9 mg; 56%) as an oil.

[M+H]$^+$=468.0

EXAMPLES 78-83

Examples 78-83 were prepared using the same sequence as for the synthesis of Example 77 (from Example 77 Part B compound) using a variety of appropriate acid chlorides (instead of p-toluoyl chloride).

| Example No. | R | [M + H]$^+$ |
|---|---|---|
| 78 | F$_3$CO—⌬— | 537.9 |
| 79 | Ph—⌬— | 482.0 |
| 80 | \O—⌬— | 484.0 |
| 81 | (methylenedioxyphenyl) | 498.0 |
| 82 | (t-butylphenyl) | 510.0 |
| 83 | (4-chlorobenzyl) | 502.2 |

EXAMPLE 84

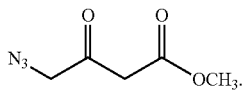

A

A mixture of methyl 4-chloroacetoacetate (400 mg; 2.6 mmol) and sodium azide (136 mg; 2.1 mmol) in acetone (6 mL) was diluted with H$_2$O (~1 mL) until the azide had dissolved. The mixture was heated at 50° C. for 1 h, stirred overnight at RT, then was heated at 50° C. for 2 h. The reaction was cooled to RT and the acetone was removed in vacuo. The aqueous phase was extracted with CH$_2$Cl$_2$; the combined organic extracts were dried (MgSO$_4$) and concentrated in vacuo. The residue was chromatographed (SiO$_2$; continuous gradient from 100% hex to 3:2 hex:EtOAc) to give Part A compound (237 mgs; 72%).

B.

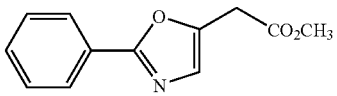

A mixture of Part A compound (237 mg; 1.51 mmol) and resin-bound Ph₃P (1.56 g of 3 mmol/g resin; 4.68 mmol) in dioxane (5 mL) was shaken for 10 min at RT. Benzoyl chloride (263 mg; 1.87 mmol) was then added and the reaction was heated at 75° C. for 2 h, then cooled to RT and filtered. The filtrate was concentrated in vacuo and the residue was chromatographed (SiO₂; continuous gradient from 100% hex to 1:1 hex:EtOAc; compound was pre-loaded onto the column with Celite®) to give Part B compound (95 mg; 28%) as a pale yellow oil.

C.

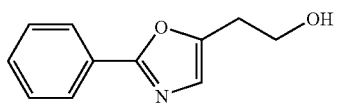

A solution of LiAlH₄ in THF (2.0 mL of a 1 M solution; 2.0 mmol) was added dropwise to Part B compound (95 mg; 0.44 mol) at RT. The reaction was stirred overnight at RT, then was cooled to 0° C. and quenched cautiously with H₂O. Aqueous 3 N NaOH was added and the mixture was concentrated in vacuo. The residue was partitioned between CH₂Cl₂ and H₂O. The aqueous phase was extracted with CH₂Cl₂; the combined organic extracts were dried (Na₂SO₄) and concentrated in vacuo. The residue was chromatographed (SiO₂; continuous gradient from 100% hex to 100% EtOAc; compound preloaded onto column with CH₂Cl₂) to provide Part C compound (100 mg; 100%) as a colorless oil.

D.

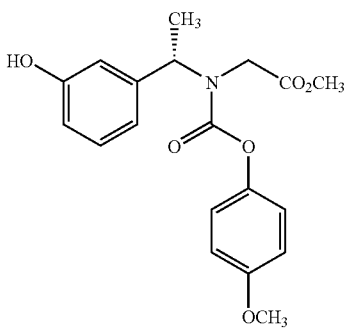

Part D compound was synthesized from (S)-1-(3-methoxyphenyl)-ethylamine using the identical sequence as for the synthesis of Example 13 Part G compound from (S)-1-(4-methoxyphenyl)-ethylamine.

E.

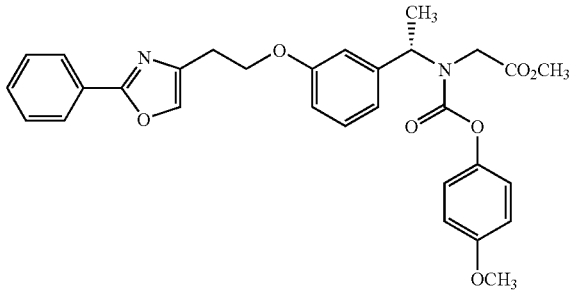

A mixture of Part C compound (20 mg; 0.106 mmol), Part D compound (35 mg; 0.098 mmol) and cyanomethylene tributylphosphorane (70 µL; 0.29 mmol) in toluene (1.5 mL) at 70° C. was shaken overnight, then was concentrated in vacuo. The residue was chromatographed (SiO₂; continuous gradient from 100% hex to 2:3 hex:EtOAc) to give a 2:1 mixture of Part E compound and unreacted Part D compound (37 mg; 55%) as a yellow oil.

[M+H]⁺=531.3

F.

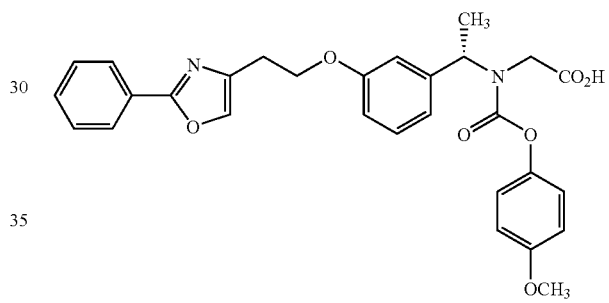

The mixture obtained in Part E (37 mg; 0.052 mmol) in a 1:1:1 mixture of 2N solution of LiOH.H₂O, MeOH and THF (1.5 mL) was stirred at RT for 2 h, then was concentrated in vacuo. The resulting aqueous solution was acidified to pH ~3 with 1N aqueous HCl and extracted with CH₂Cl₂ (3×1 mL). The combined organic extracts were concentrated in vacuo and the residue was purified by preparative HPLC (as for the purification of Example 26) to give the title compound (10 mg; 26%) as a solid.

[M+H]⁺=517.20

EXAMPLE 85

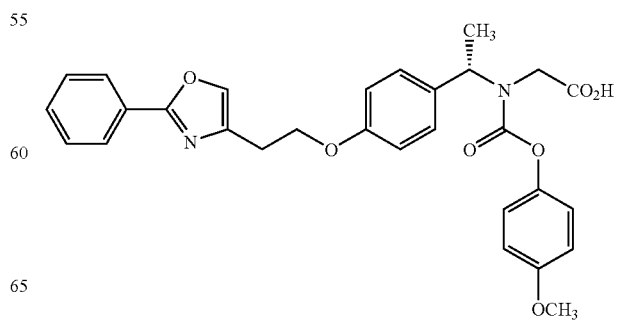

A.

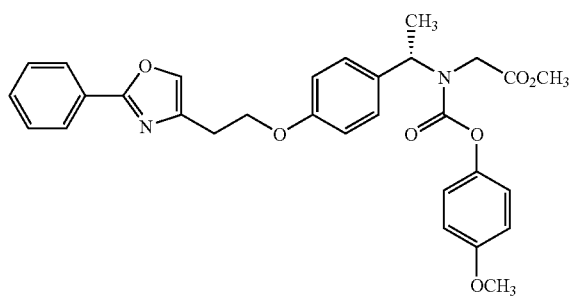

Example 84 Part C (20 mg; 0.106 mmol) compound was reacted with Example 13 Part G compound (35 mg; 0.098 mmol)

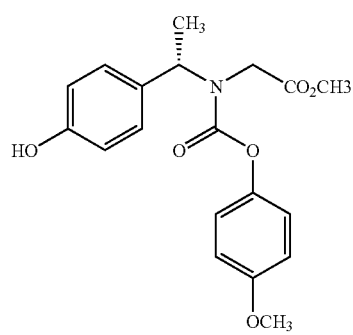

in the same way as described in Example 84 Part E to give a 2:1 mixture of Part A compound and Example 13 Part G compound (30 mg, 57%).
[M+H]$^+$=531.26

B.

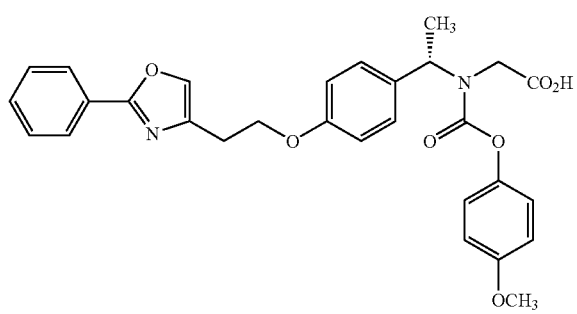

The title compound was obtained by the hydrolysis of the mixture obtained in part A (30 mg) (as described in Example 84 Part F) to provde part B. compound (13 mg, 43%).
[M+H]$^+$=517.20

EXAMPLE 86

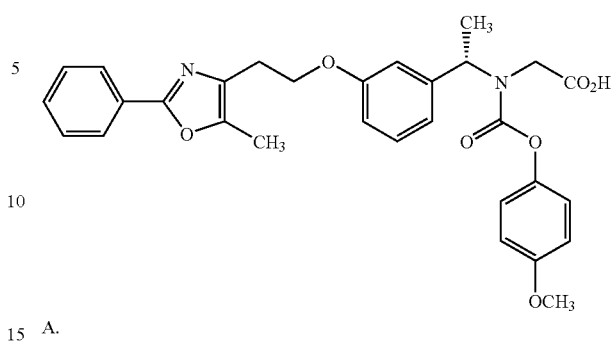

A.

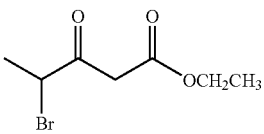

To a 0° C. solution of ethyl propionylacetate (10.0 g, 69.4 mmol) in CHCl$_3$ (60 mL) was added dropwise a solution of Br$_2$ (3.6 mL; 69.4 mmol) in CHCl$_3$ (20 mL) and the resulting mixture was stirred at 0° C. for 0.5 h. The reaction was allowed to warm to RT and stirred at RT for 0.5 h. Air was then bubbled into the mixture for 1 h. Volatiles were then removed in vacuo to yield an oily residue to provide crude Part A compound (15.3 g, >95% yield) as an oil which was used in the next reaction without further purification.

B.

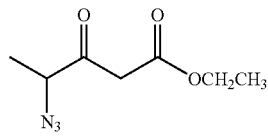

A mixture of Part A compound (400 mg; 1.79 mmol) and sodium azide (136 mg; 2.09 mmol) in acetone (6 mL) and H$_2$O (1 mL) was stirred at RT for 1 h, then at 50° C. for 1 h. Analytical HPLC indicated that the starting material had been consumed at this point. The acetone was removed in vacuo and the aqueous phase was extracted with CH$_2$Cl$_2$. The combined organic extracts were dried (MgSO$_4$) and concentrated in vacuo; the residue was chromatographed (SiO$_2$; continuous gradient from 100% hex to 1:1 hex:EtOAc) to give Part B compound (280 mg; 85%) as a pale yellow oil.

C.

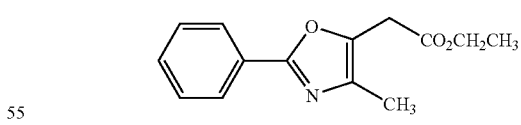

A mixture of Part B compound (100 mg; 0.54 mmol) and resin-bound Ph$_3$P (540 mg of 3 mmol/g resin; 1.62 mmol) in dioxane (4 mL) was shaken for 10 min at RT. Benzoyl chloride (84 mg; 0.60 mmol) was then added and the reaction was heated at 75° C. for 2 h, then cooled to RT and filtered. The filtrate was concentrated in vacuo and the residue was chromatographed (SiO$_2$; continuous gradient from 100% hex to 1:1 hex:EtOAc; the compound was pre-loaded onto the column with Celite®) to give Part C compound (280 mg; 85%) as a pale yellow oil.

D.

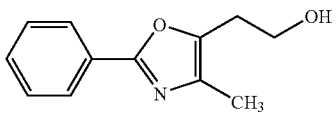

A solution of LiAlH$_4$ in THF (1 mL of a 1 M solution; 1 mmol) was added dropwise to Part C compound (75 mg; 0.30 mol) at 0° C. The reaction was warmed to RT and stirred overnight at RT, then was cooled to 0° C. and quenched cautiously with H$_2$O. Aqueous 3 N NaOH was added and the mixture was concentrated in vacuo. The residue was partitioned between CH$_2$Cl$_2$ and H$_2$O. The aqueous phase was extracted with CH$_2$Cl$_2$; the combined organic extracts were dried (Na$_2$SO$_4$) and concentrated in vacuo. The residue was chromatographed (SiO$_2$; continuous gradient from 100% hex to 100% EtOAc; compound preloaded onto column with CH$_2$Cl$_2$) to provide Part D compound (55 mg; 89%) as a colorless oil.

E.

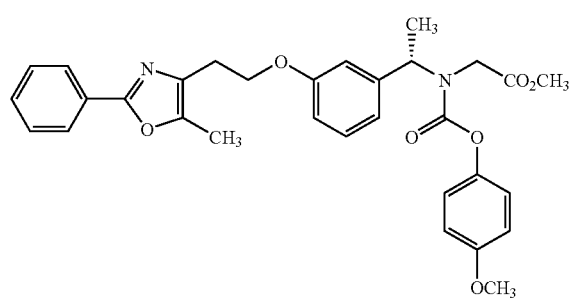

A mixture of Part D compound (20 mg; 0.100 mmol), Example 84 Part D compound (35 mg; 0.098 mmol)

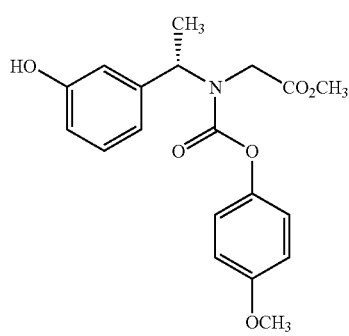

and cyanomethylene tributylphosphorane (70 µL; 0.29 mmol) in toluene (500 µL) at 70° C. was shaken overnight, then was concentrated in vacuo. The residue was chromatographed (SiO$_2$; continuous gradient from 100% hex to 2:3 hex:EtOAc) to give a 4:1 mixture of Part E compound and Example 84 Part D compound (32 mg; 55%) as a yellow oil.

[M+H]$^+$=545.26

F.

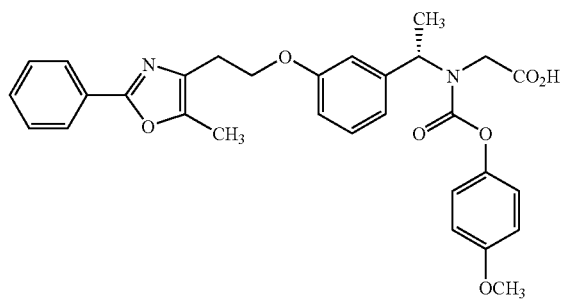

The mixture obtained in Part E (32 mg; 0.053 mmol) in a 1:1:1 mixture of 2N solution of LiOH.H$_2$O, MeOH and THF (1.5 mL) was stirred at RT for 2 h, then was concentrated in vacuo. The resulting aqueous solution was acidified to pH ~3 with 1N aqueous HCl and extracted with DCM (3×1 mL). The combined organic extracts were concentrated in vacuo and purified by preparative HPLC (as for the purification of Example 26) to give the title compound (22 mg; 68%) as a solid.

[M+H]$^+$=531.20

EXAMPLE 87

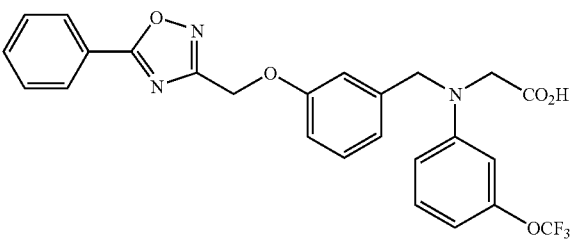

A.

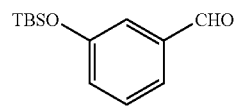

To a solution of 3-hydroxybenzaldehyde (2 g; 16.3 mmol) in DMF (20 mL) was added t-butyldimethylsilyl chloride (2.9 g; 19.6 mmol) and imidazole (1.33 g; 19.6 mmol) at RT. The solution was stirred for 2 h at RT, then was partitioned between CH$_2$Cl$_2$ (40 mL) and aqueous 1 N NaOH. The organic layer was dried (MgSO$_4$) and concentrated in vacuo. The residue was chromatographed (SiO$_2$; 9:1 hexane:EtOAc) to give Part A compound (2.3 g; 59%) as an oil.

B.

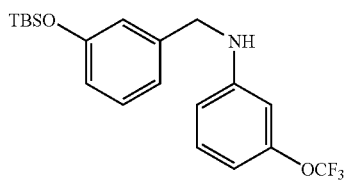

To a solution of Part A compound (2.3 g; 9.7 mmol) in CH$_2$Cl$_2$ (20 mL) was added 3-trifluoromethoxy-aniline (1.88 g; 10.7 mmol), NaBH(OAc)$_3$ (2.4 g; 11.8 mmol) and glacial HOAc (2 mL) at RT. The solution was stirred for 3 h, then was partitioned between CH$_2$Cl$_2$ (20 mL) and saturated aqueous NaHCO$_3$. The organic layer was dried (MgSO$_4$) and concen-

C.

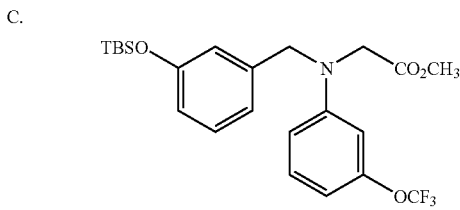

A mixture of crude Part B compound, methyl bromoacetate (4.0 g; 26 mmol) and $K_2CO_3$ (1.6 g; 11.8 mmol) in MeCN (20 mL) was stirred for 18 h at 90° C., then was cooled to RT and concentrated in vacuo. The residue was partitioned between EtOAc and brine. The organic layer was dried ($MgSO_4$) and concentrated in vacuo to give crude Part C compound as a yellow residue, which was used in the next step without further purification.

D.

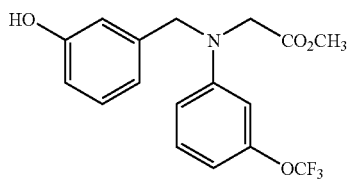

A solution of crude Part C compound in THF (10 mL) and tetrabutylammonium fluoride (15 mL of a 1 M solution in THF; 15 mmol) was stirred at RT for 1 h and concentrated in vacuo. The residue was chromatographed ($SiO_2$; 4:1 hexane:EtOAc) to give Part D compound (1.2 g; 35%) as an oil.

E.

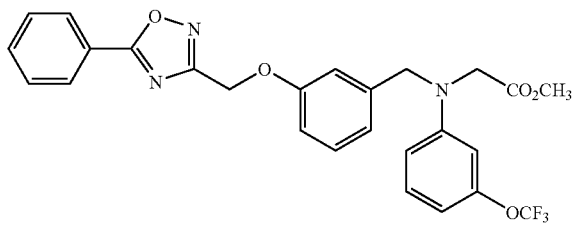

A mixture of Part D compound (20 mg; 0.05 mmol), Example 12 Part C compound (21 mg; 0.11 mmol)

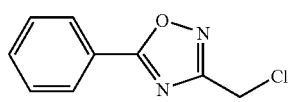

and $K_2CO_3$ (15 mg; 0.11 mmol) in MeCN (5 mL) was stirred for 12 h at 80° C., then was cooled to RT and concentrated in vacuo to give the crude Part E compound, which was used in the next step without further purification.

F.

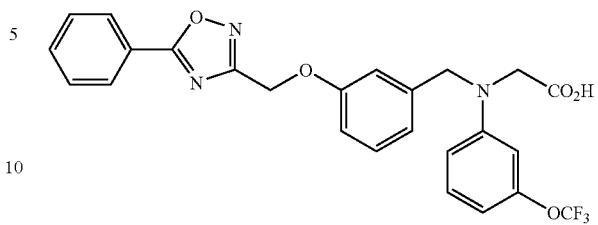

A solution of crude Part E compound in MeOH (2 mL) and 1 N aqueous KOH (1 mL); the solution was stirred for 2 h at RT, then was neutralized with 1N aqueous HCl and concentrated in vacuo. The residue was purified by HPLC (YMC reverse-phase ODS 20×100 mm column; flow rate=20 mL/min; 10 min continuous gradient from 30:70 B:A to 100% B+5 min hold-time at 100% B, where solvent A=90:10:0.1 $H_2O$:MeOH:TFA and solvent B=90:10:0.1 MeOH:$H_2O$:TFA) to give the title Compound (4 mg; 14%) as a solid. $[M+H]^+=500.4$

EXAMPLE 88

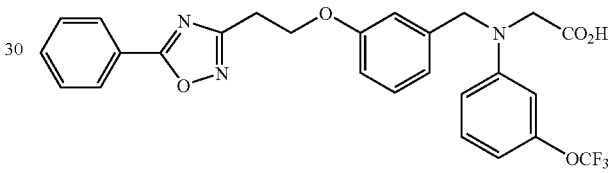

A.

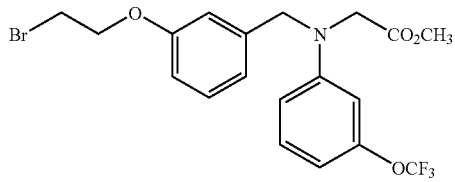

A mixture of Example 87 Part D compound (0.1 g; 0.28 mmol), 1,2-dibromoethane (5 mL; 12.2 mmol) and $K_2CO_3$ (0.38 g; 0.28 mmol) n MeCN (20 mL) was stirred for 20 h at 90° C., then was cooled to RT and concentrated in vacuo. The residue was partitioned between EtOAc and brine. The organic layer was dried ($MgSO_4$) and concentrated in vacuo to give crude Part A compound as a yellow oil, which was used in the next step without further purification.

B.

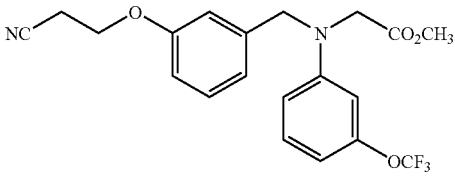

A solution of crude Part A compound and tetrabutylammonium nitrile (75 mg; 0.28 mmol) in $CH_2Cl_2$ (10 mL) was stirred at RT for 18 h and concentrated in vacuo. The residue was chromatographed ($SiO_2$; 9:1 hexane:EtOAc) to give Part B compound (70 mg; 61%) as an oil.

C.

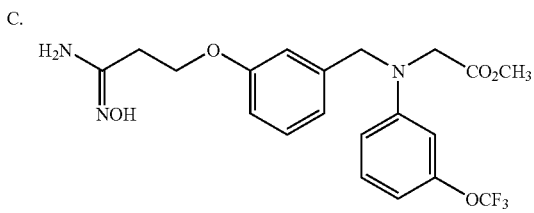

To a solution of Part B Compound (55 mg; 0.13 mmol) in MeOH (2 mL) was added hydroxylamine (17 mg of a 50% solution in water; 0.53 mmol) at RT. The solution was stirred for 18 h at RT and concentrated in vacuo. The residue partitioned between EtOAc and brine. The organic layer was dried (MgSO$_4$) and concentrated in vacuo to give crude Part C compound as a yellow oil, which was used in the next step without further purification.

D.

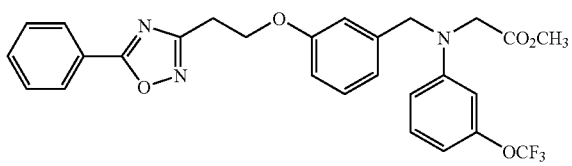

To a solution of crude Part C compound in CH$_2$Cl$_2$ (2 mL) was added benzoyl chloride (18 mg; 0.13 mmol) and Et$_3$N (10 µL). The solution was stirred for 2 h at RT and then concentrated in vacuo. The residue was dissolved in pyridine (5 mL) and stirred for 2 h at 80° C., then was cooled to RT and concentrated in vacuo to give crude Part D compound, which was used in the next step without further purification.

E.

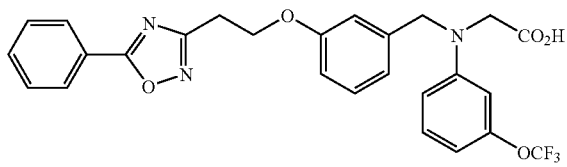

A solution of crude Part D compound in MeOH (2 mL) and aqueous 1 N KOH (1 mL) was stirred for 2 h at RT and then was neutralized with aqueous 1 N HCl and concentrated in vacuo. The residue was purified by HPLC (YMC reverse-phase ODS 20×100 mm column; flow rate=20 mL/min; 10 min continuous gradient from 30:70 B:A to 100% B+5 min hold-time at 100% B, where solvent A=90:10:0.1 H$_2$O: MeOH:TFA and solvent B=90:10:0.1 MeOH:H$_2$O:TFA) to give the title Compound (5 mg; 7%)

[M+H]$^+$=514.5

What is claimed is:

1. A compound which has the structure

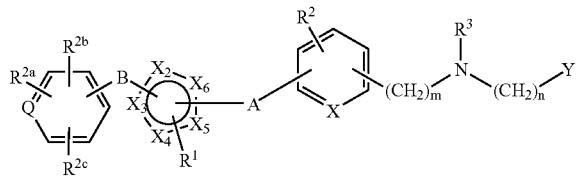

wherein m is 0, 1 or 2; n is 0, 1 or 2;

Q is C;

A is (CH$_2$)$_x$ where x is 1 to 5 or A is (CH$_2$)$_x^1$ where x$^1$ is 1 to 5 with an alkenyl bond or an alkynyl bond embedded anywhere in the chain, or A is —(CH$_2$)$_x^2$—O—(CH$_2$)$_x^3$—where x$^2$ is 0 to 5 and x$^3$ is 0 to 5, provided that at least one of x$^2$ and x$^3$ is other than 0;

B is a bond or is (CH$_2$)$_x^4$ where x$^4$ is 1 to 5;

X is CH;

X$_2$ is N;

X$_3$ is C;

X$_4$ is N;

X$_5$ is C;

X$_6$ is C;

R$^1$ is H or alkyl;

R$^2$ is H, alkyl, alkoxy, halogen, amino or substituted amino or cyano;

R$^{2a}$, R$^{2b}$ and R$^{2c}$ may be the same or different and are selected from H, alkyl, alkoxy, halogen, amino or substituted amino or cyano;

R$^3$ is selected from H, alkyl, arylalkyl, aryloxycarbonyl, alkyloxycarbonyl, alkynyloxycarbonyl, alkenyloxycarbonyl, arylcarbonyl, alkylcarbonyl, aryl, heteroaryl, cycloheteroalkyl, heteroarylcarbonyl, heteroaryl-heteroarylalkyl, alkylcarbonylamino, arylcarbonylamino, heteroarylcarbonylamino, alkoxycarbonylamino, aryloxycarbonylamino, heteroaryloxycarbonylamino, heteroaryl-heteroarylcarbonyl, alkylsulfonyl, alkenylsulfonyl, heteroaryloxycarbonyl, cycloheteroalkyloxycarbonyl, heteroarylalkyl, aminocarbonyl, substituted aminocarbonyl, alkylaminocarbonyl, arylaminocarbonyl, heteroarylalkenyl, cycloheteroalkyl-heteroarylalkyl; hydroxyalkyl, alkoxy, alkoxyaryloxycarbonyl, arylalkyloxycarbonyl, alkylaryloxycarbonyl, arylheteroarylalkyl, arylalkylarylalkyl, aryloxyarylalkyl, haloalkoxyaryloxycarbonyl, alkoxycarbonylaryloxycarbonyl, aryloxyaryloxycarbonyl, arylsulfinylarylcarbonyl, arylthioarylcarbonyl, alkoxycarbonylaryloxycarbonyl, arylalkenyloxycarbonyl, heteroaryloxyarylalkyl, aryloxyarylcarbonyl, aryloxyarylalkyloxycarbonyl, arylalkenyloxycarbonyl, arylalkylcarbonyl, aryloxyalkyloxycarbonyl, arylalkylsulfonyl, arylthiocarbonyl, arylalkenylsulfonyl, heteroarylsulfonyl, arylsulfonyl, alkoxyarylalkyl, heteroarylalkoxycarbonyl, arylheteroarylalkyl, alkoxyarylcarbonyl, aryloxyheteroarylalkyl, heteroarylalkyloxyarylalkyl, arylarylalkyl, arylalkenylarylalkyl, arylalkoxyarylalkyl, arylcarbonylarylalkyl, alkylaryloxyarylalkyl, arylalkoxycarbonylheteroarylalkyl, heteroarylarylalkyl, arylcarbonylheteroarylalkyl, heteroaryloxyarylalkyl, arylalkenylheteroarylalkyl, arylaminoarylalkyl, aminocarbonylarylalkyl;

Y is CO$_2$R$^4$ where R$^4$ is H or alkyl, or Y is a C-linked 1-tetrazole, a phosphonic acid of the structure P(O)(OR$^{4a}$)R$^5$ where R$^{4a}$ is H, R$^5$ is alkyl or aryl, or a phosphonic acid of the structure P(O)(OR$^{4a}$)$_2$;

(CH$_2$)$_x^4$, (CH$_2$)$_m$, and (CH$_2$)$_n$ may be optionally substituted with 1, 2 or 3 substituents elected from the group consisting of alkyl, alkenyl, halogen, cyano, hydroxy, alkoxy, amino, thioalkyl, keto, C$_3$-C$_6$ cycloalkyl, alkylcarbonylamino, and alkylcarbonyloxy; or the alkyl substituent is an alkylene moiety of 1 to 4 carbons which may be attached to any of the (CH$_2$)$_x^4$, (CH$_2$)$_m$, and (CH$_2$)$_n$ groups to form a cycloalkyl therewith;

wherein the term "heteroaryl" as used herein by itself or as part of another group refers to a 5- or 6-membered aromatic ring which includes 1, 2, 3 or 4 heteroatoms selected from the group consisting of N, O and S and such rings fused to an aryl, cycloalkyl, heteroaryl or cycloheteroalkyl ring;

and the term "cycloheteroalkyl" by itself or as part of another group refers to a 5-, 6- or 7-membered saturated or partially unsaturated ring containing 1 or 2 hetero atoms which is selected from the group consisting of N, O and S and such rings fused to a cycloalkyl, aryl, heteroaryl or cycloheteroalkyl ring, and all stereoisomers thereof, and pharmaceutically acceptable salts thereof.

2. The compound as defined in claim 1 wherein A is —$(CH_2)_x^2$—O—.

3. The compound as defined in claim 1 wherein B is a bond.

4. The compound as defined in claim 1 wherein

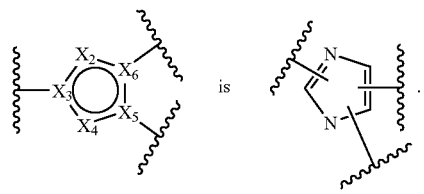

5. The compound as defined in claim 1 wherein $R^3$ is arylalkyloxycarbonyl, arylheteroarylalkyl, aryloxyarylalkyl, arylalkyl, aryloxycarbonyl, haloaryl-oxycarbonyl, alkoxyaryloxycarbonyl, alkylaryloxycarbonyl, aryloxyaryloxycarbonyl, heteroaryloxyarylalkyl, heteroaryloxycarbonyl, aryloxyarylcarbonyl, arylalkenyloxycarbonyl, cycloalkylaryloxycarbonyl, arylalkylarylcarbonyl, heteroaryl-heteroarylalkyl, cycloalkyloxyaryloxycarbonyl, heteroaryl-heteroarylcarbonyl, arylalkylsulfonyl, arylalkenylsulfonyl, alkoxyarylalkyl, arylthiocarbonyl, cycloheteroalkylalkyloxycarbonyl, cycloheteroalkyloxycarbonyl, or polyhaloalkylaryloxycarbonyl, which may be optionally substituted.

6. The compound as defined in claim 1 which has the structure

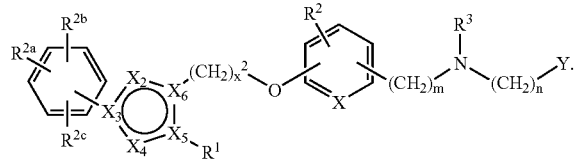

7. The compound as defined in claim 1 which has the structure

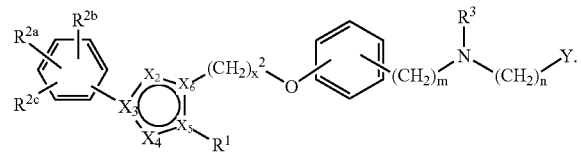

8. The compound as defined in claim 7 wherein $R^{2a}$, $R^{2b}$ and $R^{2c}$ are each H; $R^1$ is alkyl, $x^2$ is 1 to 3; m is 0 or $(CH_2)_m$ is $CH_2$ or CHOH or CH-alkyl, $(CH_2)_n$ is a bond or $CH_2$ and $R^3$ is alkoxyaryloxycarbonyl.

9. The compound as defined in claim 8 wherein $R^1$ is $CH_3$ and $R^3$ is methyloxyphenyloxycarbonyl.

10. The compound as defined in claim 1 wherein

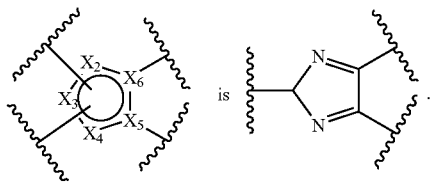

11. A pharmaceutical composition comprising a compound as defined in claim 1 and a pharmaceutically acceptable carrier therefor.

12. A method for treating diabetes or Type 2 diabetes, which comprises administering to a patient in need of treatment a therapeutically effective amount of a compound as defined in claim 1.

13. The compound as defined in claim 1 having the structure

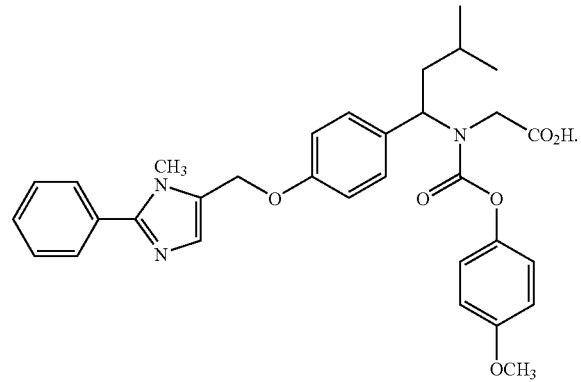

* * * * *

UNITED STATES PATENT AND TRADEMARK OFFICE
CERTIFICATE OF CORRECTION

PATENT NO.         : 7,507,757 B2
APPLICATION NO.    : 11/016183
DATED              : March 24, 2009
INVENTOR(S)        : Peter T. W. Cheng et al.

Page 1 of 1

It is certified that error appears in the above-identified patent and that said Letters Patent is hereby corrected as shown below:

In the Claims:

Claim 1:
    Column 108, line 35, delete "-heteroarylalkyl".
    Column 108, line 57, change "phosphonic" to -- phosphinic --.

Claim 10:
    Column 110, lines 20 to 27, change

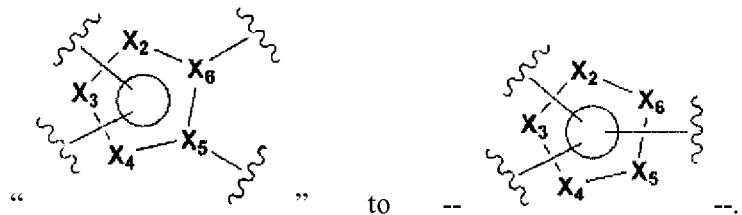

" " to -- --.

Claim 11:
    Column 110, line 31, change "therefor" to -- thereof --.

Signed and Sealed this
Eighteenth Day of January, 2011

David J. Kappos
*Director of the United States Patent and Trademark Office*